US011136356B2

(12) United States Patent
Kwong et al.

(10) Patent No.: US 11,136,356 B2
(45) Date of Patent: Oct. 5, 2021

(54) RECOMBINANT HIV-1 ENVELOPE PROTEINS AND THEIR USE

(71) Applicant: The United States of America, as represented by the Secretary, Department of Health and Human Services, Bethesda, MD (US)

(72) Inventors: Peter Kwong, Washington, DC (US); John Mascola, Rockville, MD (US); Gwo-Yu Chuang, Rockville, MD (US); Hui Geng, Rockville, MD (US); Yongping Yang, Potomac, MD (US); Cheng Cheng, Bethesda, MD (US); Jeffrey Boyington, Clarksburg, MD (US); Yen-Ting Lai, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/756,777

(22) PCT Filed: Oct. 16, 2018

(86) PCT No.: PCT/US2018/056135

§ 371 (c)(1),
(2) Date: Apr. 16, 2020

(87) PCT Pub. No.: WO2019/079337

PCT Pub. Date: Apr. 25, 2019

(65) Prior Publication Data

US 2021/0188921 A1 Jun. 24, 2021

Related U.S. Application Data

(60) Provisional application No. 62/572,973, filed on Oct. 16, 2017.

(51) Int. Cl.

| | |
|---|---|
| ***C07K 14/005*** | (2006.01) |
| ***A61K 39/00*** | (2006.01) |
| ***A61K 39/12*** | (2006.01) |
| ***A61K 39/21*** | (2006.01) |
| ***C12N 7/00*** | (2006.01) |
| ***C07K 14/16*** | (2006.01) |
| ***A61K 39/39*** | (2006.01) |

(52) U.S. Cl.

CPC ............ *C07K 14/162* (2013.01); *A61K 39/12* (2013.01); *A61K 39/39* (2013.01); *A61K 2039/64* (2013.01)

(58) Field of Classification Search

CPC .................. C07K 14/005; A61K 39/12; C12N 2740/16122; C12N 2740/16134; C12N 7/00

See application file for complete search history.

(56) References Cited

U.S. PATENT DOCUMENTS

| | | | |
|---|---|---|---|
| 6,689,879 | B2 | 2/2004 | Barnett et al. |
| 9,738,688 | B2 | 8/2017 | Caulfield et al. |
| 2014/0212458 | A1 | 7/2014 | Caulfield et al. |

FOREIGN PATENT DOCUMENTS

| | | | |
|---|---|---|---|
| EP | 2873423 | A2 | 5/2015 |
| WO | WO 2013/189901 | A1 | 12/2013 |
| WO | WO 2014/022475 | A2 | 2/2014 |
| WO | WO 2016/037154 | A1 | 3/2016 |

OTHER PUBLICATIONS

Chuang et al., "Structure-Based Design of a Soluble Prefusion-Closed HIV-1 Env Trimer with Reduced CD4 Affinity and Improved Immunogenicity", Journal of Virology, 2017, 91 (10):1-18.*

Acharya et al., "Structural Definition of an Antibody-Dependent Cellular Cytotoxicity Response Implicated in Reduced Risk for HIV-1 Infection," *J Virol*. 88.21: 12895-12906, Nov. 2014.

Barouch et al., "A Human T-Cell Leukemia Virus Type 1 Regulatory Element Enhances the Immunogenicity of Human Immunodeficiency Virus Type 1 DNA Vaccines in Mice and Nonhuman Primates," *J. Virol*. 79.14: 8828-8834, Jul. 2005.

Calarese et al., "Antibody Domain Exchange is an Immunological Solution to Carbohydrate Cluster Recognition," *Science* 300.5628: 2065-2071, Jun. 2003.

Chen et al., "Structural Basis of Immune Evasion at the Site of CD4 Attachment on HIV-1 gp120," *Science* 326.5956: 1123-1127, Nov. 2009.

Cheng et al., "Immunogenicity of a Prefusion HIV-1 Envelope Trimer in Complex with a Quaternary-Structure-Specific Antibody," *J Virol*. 90.6: 2740-2755, Dec. 2015.

Chow et al., "Conserved Structures Exposed in HIV-1 Envelope Glycoproteins Stabilized by Flexible Linkers as Potent Entry Inhibitors and Potential Immunogens," Biochemistry 41.22: 7176-7182, Jun. 2002.

Chuang et al., Structure-Based Design of a Soluble Prefusion-Closed HIV-1 Env Trimer with Reduced CD4 Affinity and Improved Immunogenicity, *J Virol*. 91.10: e00268-16, May 2017.

de Taeye et al. "Immunogenicity of Stabilized HIV-1 Envelope Trimers with Reduced Exposure of Non-Neutralizing Epitopes," *Cell* 163.7: 1702-1715, Dec. 2015.

Doria-Rose et al., "Developmental Pathway for Potent V1V2-Directed HIV-Neutralizing Antibodies," *Nature* 509.7498: 55-62, May 2014.

Doria-Rose et al., "New Member of the V1V2-Directed CAP256-VRC26 Lineage That Shows Increased Breadth and Exceptional Potency," *J Virol*. 90.1:76-91, Oct. 2015.

(Continued)

*Primary Examiner* — Barry A Chestnut

(74) *Attorney, Agent, or Firm* — Klarquist Sparkman, LLP

(57) ABSTRACT

Immunogens comprising a recombinant HIV-1 Env ectodomain trimer stabilized in a prefusion closed conformation and methods of their use and production are disclosed. In several embodiments, the immunogen can be used to elicit an immune response to HIV-1 in a subject.

32 Claims, 14 Drawing Sheets

Specification includes a Sequence Listing.

(56) References Cited

OTHER PUBLICATIONS

Dreyfus et al., "Highly Conserved Protective Epitopes on Influenza B Viruses," *Science* 337.6100: 1343-1348, Sep. 2012.
Falkowska et al., "Broadly Neutralizing HIV Antibodies Define a Glycan-Dependent Epitope on the Pre-Fusion Conformation of gp41 Protein on Cleaved Envelope Trimers," *Immunity* 40.5: 657-668, May 2014.
Georgiev et al., "Delineating Antibody Recognition in Polyclonal Sera from Patterns of HIV-1 Isolate Neutralization," *Science* 340. 6133: 751-756, May 2013.
Georgiev et al., "Single-Chain Soluble BG505.SOSIP gp140 Trimers as Structural and Antigenic Mimics of Mature Closed HIV-1 Env," *J Virol.* 89.10: 5318-5329, May 2015.
Gorny et al., "Cross-Clade Neutralizing Activity of Human Anti-V3 Monoclonal Antibodies Derived from the Cells of Individuals Infected with Non-B Clades of Human Immunodeficiency Virus Type 1," *J Virol.* 80.14: 6865-6872, Jul. 2006.
Gorny et al., "Human Anti-V3 HIV-1 Monoclonal Antibodies Encoded by the VH5-51/VL Lambda Genes Define a Conserved Antigenic Structure," *PLoS One* 6.12: e27780, Dec. 2011.
Guenaga et al., "Structure-Guided Redesign Increases the Propensity of HIV Env to Generate Highly Stable Soluble Trimers," *J Virol.* 90.6: 2806-2817, Mar. 2016.
Guenaga et al., "Glycine Substitution at Helix-to-Coil Transitions Facilitates the Structural Determination of a Stabilized Subtype C HIV Envelope Glycoprotein," *Immunity* 46.5: 792-803, May 2017.
Huang et al., "Broad and Potent HIV-1 Neutralization by a Human Antibody that Binds the gp41-gp120 Interface," *Nature* 515.7525: 138-142, Nov. 2014.
International Search Report and Written Opinion for PCT/US2015/048729, dated Nov. 9, 2015 (14 pages).
Jiang et al., "Conserved Structural Elements in the V3 Crown of HIV-1 gp120," *Nat Struct Mol Biol.* 17.8: 955-961, Aug. 2010.
Joyce et al., "Soluble Prefusion Closed DS-SOSIP.664-Env Trimers of Diverse HIV-1 Strains," *Cell Reports* 21.10: 2992-3002, Dec. 2017.
Julien et al., "Crystal Structure of a Soluble Cleaved HIV-1 Envelope Trimer," *Science* 342.6165: 1477-1483, Dec. 2013.
Kanekiyo et al., "Self-Assembling Influenza Nanoparticle Vaccines Elicit Broadly Neutralizing H1N1 Antibodies," Nature 499.7456: 102-106, 2013.
Kassa et al., "Stabilizing Exposure of Conserved Epitopes by Structure Guided Insertion of Disulfide Bond in HIV-1 Envelope Glycoprotein," *PLoS One* 8.10: e76139, Oct. 2013.
Killikelly et al., "Thermodynamic Signatures of the Antigen Binding Site of mAb 447-52D Targeting the Third Variable Region of HIV-1 gp120," *Biochemistry* 52.36: 6249-6257, Sep. 2013.
Kong et al., "Uncleaved Prefusion-Optimized gp140 Trimers Derived from Analysis of HIV-1 Envelope Metastability," *Nat Commun.* 7: 12040, Jun. 2016.
Kwon et al., "Crystal Structure, Conformational Fixation and Entry-Related Interactions of Mature Ligand-Free HIV-1 Env," *Nat Struct Mol Biol.* 22.7: 522-531, Jul. 2015.
Kwong et al., "Structure of an HIV gp120 Envelope Glycoprotein in Complex with the CD4 Receptor and a Neutralizing Human Antibody," *Nature* 393.6686: 648-659, Jun. 1998.
Lyumkis et al., "Cryo-EM Structure of a Fully Glycosylated Soluble Cleaved HIV-1 Envelope Trimer," *Science* 342.6165: 1484-1490, Dec. 2013.
McLellan et al., "Structure of RSV Fusion Glycoprotein Trimer Bound to a Prefusion-Specific Neutralizing Antibody," *Science* 340.6136: 1113-1117, May 2013.
Pancera et al., "Structure and Immune Recognition of Trimeric Pre-Fusion HIV-1 Env," *Nature* 514.7523: 455-461, Oct. 2014.
Pugach et al., "A Native-Like SOSIP.664 Trimer Based on an HIV-1 Subtype B Env Gene," *J Virol.* 89.6: 3380-3395, Mar. 2015.
Rini et al., "Crystal Structure of a Human Immunodeficiency Virus Type 1 Neutralizing Antibody, 50.1, in Complex with its V3 Loop Peptide Antigen," *Proc Natl Acad Sci USA* 90.13: 6325-6329, Jul. 1993.
Rutten et al., "A Universal Approach to Optimize the Folding and Stability of Prefusion-Closed HIV-1 Envelope Trimers," *Cell Rep.* 23.2: 584-595, Apr. 2018.
Sanders et al., "A Next-Generation Cleaved, Soluble HIV-1 Env Trimer, BG505 SOSIP.664 gp140, Expresses Multiple Epitopes for Broadly Neutralizing but not Non-Neutralizing Antibodies," *PLoS Pathog.* 9.9: e1003618, Sep. 2013.
Scheid et al., "Broad Diversity of Neutralizing Antibodies Isolated from Memory B Cells in HIV-Infected Individuals," Nature 458. 7238: 636-640, Apr. 2009.
Sharma et al., "Cleavage-Independent HIV-1 Env Trimers Engineered as Soluble Native Spike Mimetics for Vaccine Design," *Cell Rep.* 11.4: 539-550, Apr. 2015.
Sliepen et al. "Presenting Native-Like HIV-1 Envelope Trimers on Ferritin Nanoparticles Improves their Immunogenicity," *Retrovirology* 12: 82, Sep. 2015.
Stanfield et al., "Crystal Structures of Human Immunodeficiency Virus Type 1 (HIV-1) Neutralizing Antibody 2219 in Complex with Three Different V3 Peptides Reveal a New Binding Mode for HIV-1 Cross-Reactivity," *J Virol.* 80.12: 6093-6105, Jun. 2006.
Steichen et al., "HIV Vaccine Design to Target Germline Precursors of Glycan-Dependent Broadly Neutralizing Antibodies," *Immunity* 45.3: 483-496, Sep. 2016.
Thali et al., "Characterization of Conserved Human Immunodeficiency Virus Type 1 gp120 Neutralization Epitopes Exposed upon gp120-CD4 Binding," *J Virol.* 67.7: 3978-3988, Jul. 1993.
Walker et al., "Broad Neutralization Coverage of HIV by Multiple Highly Potent Antibodies," *Nature* 477.7365: 466-470, Sep. 2011.
Wu et al., "Rational Design of Envelope Identifies Broadly Neutralizing Human Monoclonal Antibodies to HIV-1," *Science* 329. 5993: 856-861, Aug. 2010.
Zhou et al., "Structural Definition of a Conserved Neutralization Epitope on HIV-1 gp120," *Nature* 445.7129: 732-737, Feb. 2007.
Zhou et al., "Structural Repertoire of HIV-1-Neutralizing Antibodies Targeting the CD4 Supersite in 14 Donors," *Cell* 161.6: 1280-1292, Jun. 2015.

* cited by examiner

| Trimers | Protein yield (mg/liter) | |
|---|---|---|
| | SEC | V3-negative selection |
| DS-SOSIP.A329P | 1.4 | 0.9 |
| DS-SOSIP.2mut | 1.7 | 1.2 |
| DS-SOSIP.3mut | 1.9 | 1.3 |
| DS-SOSIP.5mut | 1.6 | 1.1 |
| DS-SOSIP.4mut | 1.6 | 1.1 |
| DS-SOSIP | 1.7 | 1.3 |
| SOSIP.664 | 3.4 | 2.2 |

FIG. 5B

| Trimers | $K_d$ (nM) | $k_a$ ($M^{-1}s^{-1}$) | $k_d$ ($s^{-1}$) |
|---|---|---|---|
| DS-SOSIP.A329P | 11.4 (0.02) | 1.05 (0.02) X $10^5$ | 1.2 (0.01) X $10^{-3}$ |
| DS-SOSIP.2mut | 379 (0.11) | 3.08 (0.07) X $10^4$ | 1.17 (0.02) X $10^{-2}$ |
| DS-SOSIP.3mut | 357 (0.05) | 3.22 (0.04) X $10^4$ | 1.15 (0.01) X $10^{-2}$ |
| DS-SOSIP.5mut | 400 (0.14) | 3.54 (0.12) X $10^4$ | 1.42 (0.02) X $10^{-2}$ |
| DS-SOSIP.4mut | 363 (0.1) | 3.3 (0.09) X $10^4$ | 1.2 (0.01) X $10^{-2}$ |
| DS-SOSIP | 11.3 (0.02) | 9.82 (0.14) X $10^4$ | 1.11 (0.01) X $10^{-3}$ |
| SOSIP.664 | 1.08 (0.01) | 1.03 (0.01) X $10^5$ | 1.12 (0.01) X $10^{-4}$ |

| | Trimers | $T_m$ (°C) | $\Delta T_{1/2}$(°C) | ΔH (kcal/M) |
|---|---|---|---|---|
| c | DS-SOSIP.A329P | 74.1 | 5.85 | 1140 |
| d | DS-SOSIP.2mut | 76.8 | 4.18 | 1110 |
| e | DS-SOSIP.3mut | 78.3 | 4.18 | 1150 |
| g | DS-SOSIP.5mut | 78.1 | 4.18 | 1130 |
| f | DS-SOSIP.4mut | 75.8 | 4.59 | 1190 |
| b | DS-SOSIP | 72.2 | 6.26 | 1210 |
| a | SOSIP.664 | 66.6 | 4.17 | 933 |

Characterization of Cap256-RnS-3mut-2G-FP8v2

Protein Yield 2D classes

Characterization of ConC_Base0-3mut-2G-FP8v2

Thermostability

| Trimers | $T_m$ (°C) | $\Delta T_{1/2}$(°C) | ΔH (kcal/M) |
|---|---|---|---|
| Cap256-RnS-3mut-2G | 77.04 | 5.85 | 959 |
| Cap256-RnS-3mut-2G_FP8v2 | 76.63 | 5.85 | 709 |

| Trimers | $T_m$ (°C) | $\Delta T_{1/2}$(°C) | ΔH (kcal/M) |
|---|---|---|---|
| Jansen-7mut | 73.29 | 7.1 | 1140 |
| ConC-Base0-2G_FP8v2 | 74.13 | 6.26 | 1140 |

RECOMBINANT HIV-1 ENVELOPE PROTEINS AND THEIR USE

CROSS REFERENCE TO RELATED APPLICATIONS

This is the U.S. National Stage of International Application No. PCT/US2018/056135, filed Oct. 16, 2018, which was published in English under PCT Article 21(2), which in turn claims the benefit of U.S. Provisional Application No. 62/572,973, filed Oct. 16, 2017. The provisional application is incorporated herein by reference in its entirety.

FIELD

This disclosure relates to recombinant Human immunodeficiency virus type 1 (HIV-1) Envelope (Env) ectodomain trimers for treatment and inhibition of HIV-1 infection and disease.

BACKGROUND

Millions of people are infected with HIV-1 worldwide, and 2.5 to 3 million new infections have been estimated to occur yearly. Although effective antiretroviral therapies are available, over a million succumb to AIDS every year, especially in sub-Saharan Africa, underscoring the need to develop measures to prevent the spread of this disease.

An enveloped virus, HIV-1 hides from humoral recognition behind a wide array of protective mechanisms. The major envelope protein of HIV-1 is a glycoprotein of approximately 160 kD (gp160). During infection, proteases of the host cell cleave gp160 into gp120 and gp41. Gp41 is an integral membrane protein, while gp120 protrudes from the mature virus. Together gp120 and gp41 make up the HIV-1 Env spike, which is a target for neutralizing antibodies.

It is believed that immunization with an effective immunogen based on the HIV-1 Env glycoprotein can elicit a neutralizing response, which may be protective against HIV-1 infection. However, despite extensive effort, a need remains for agents capable of such action.

SUMMARY

This disclosure provides novel recombinant HIV-1 Env ectodomain trimers (such as soluble HIV-1 Env ectodomain trimers as well as membrane-anchored HIV-1 Env ectodomain trimers including a full-length gp41 protein) that include one or more amino acid substitutions that "lock" the recombinant HIV-1 Env trimer in a prefusion closed conformation with a reduced binding affinity for CD4 relative to non-modified trimers, but that retain binding affinity for broadly neutralizing HIV-1 antibodies. The disclosed recombinant HIV-1 Env ectodomain trimers can be used to elicit a neutralizing immune response to HIV-1 in a subject.

In some embodiments, the recombinant HIV-1 Env ectodomain trimer is stabilized in the prefusion closed conformation by amino acid substitutions in protomers of the trimer, wherein the amino acid substitutions comprise cysteine substitutions at HIV-1 Env positions 501 and 605 that form a non-natural intra-protomer disulfide bond, a proline substitution at HIV-1 Env position 559, as well as the "3mut" substitutions disclosed herein: a methionine substitution at HIV-1 Env position 302, a leucine substitution at HIV-1 Env position 320; and a proline substitution at HIV-1 Env positon 329. The positions of the substitutions are relative to the HXB2 numbering system. In some embodiments, the protomers of the trimer comprise cysteine substitutions at HIV-1 Env positions 201 and 433 that form a non-natural intra-protomer disulfide bond. In some embodiments, the amino acid substitutions comprise I201C and A433C, A501C and T605C, I559P, N302M, T320L, and A329P substitutions. In some embodiments, the protomers of the HIV-1 Env ectodomain trimer further comprise modification of the gp120/gp41 furin cleavage site, for example by substituting the four residues of the canonical furin cleave site for five or six arginine residues. In some embodiments, the recombinant HIV-1 Env ectodomain trimer is soluble and the protomers of the HIV-1 Env ectodomain trimer comprise a C-terminal truncation at position 664.

Nucleic acid molecules encoding the disclosed recombinant HIV-1 Env ectodomain trimers are also provided. In some embodiments, the nucleic acid molecule can encode a precursor protein of a gp120-gp41 protomer of a disclosed recombinant HIV-1 Env trimer. Expression vectors (such as an inactivated or attenuated viral vector) including the nucleic acid molecules are also provided.

Immunogenic compositions including one or more of the disclosed recombinant HIV-1 Env ectodomain trimers are also provided. The composition may be contained in a unit dosage form. The composition can further include an adjuvant.

Methods of eliciting an immune response to HIV-1 envelope protein in a subject are disclosed, as are methods of treating, inhibiting or preventing an HIV-1 infection in a subject. In such methods a subject, such as a human subject, is administered an effective amount of a disclosed recombinant HIV-1 Env ectodomain trimer to elicit the immune response. The subject can be, for example, a human subject at risk of or having an HIV-1 infection.

The foregoing and other features and advantages of this disclosure will become more apparent from the following detailed description of several embodiments which proceeds with reference to the accompanying figures.

BRIEF DESCRIPTION OF THE FIGURES

(FIG. 1A) Phi-Psi angle of residue 329 in the prefusion-closed conformation of DS-SOSIP.4mut (PDB:5UTY). (FIG. 1B) Phi-Psi angle of residue 329 in the CD4-bound conformation of SOSIP.664 (PDB:5VN3). (FIG. 1C) Ramachandran plot of allowable proline phi-psi angles, with phi-psi angles of A329 from 5UTY and 5VN3 labeled. (FIG. 1D) Close-up view of the 3mut region with the two residues from 4mut that were mutated back to wild type amino acid types in DS-SOSIP.3mut, L154 and N300, shown in dark grey.

(FIG. 2A) purification flow-chart. The purification protocol involved sequential steps of a VRC01 affinity column, gel filtration chromatography (SEC), a 447-52D mAb negative selection affinity column, and a V3 mAb negative selection affinity column. (FIG. 2B) Size-exclusion chromatography (SEC) profiles of stabilized DS-SOSIP variants prior to V3-negative selection. (FIG. 2C) SDS-PAGE of stabilized DS-SOSIP variants post to V3-negative selection. (FIG. 2D) Expression yield of stabilized DS-SOSIP variants after SEC or SEC with V3-negative selection.

(FIG. 3A) Antigenicity of stabilized DS-SOSIP prior to V3-negative selection or after V3-negative selection, assessed with broadly neutralizing antibodies (VRC01, PGT145), weakly or non-neutralizing antibodies (F105, 447-52D, 3074), and a control antibody (CR9114, a flu antibody with no recognition of HIV-1 Env). (FIG. 3B) Antigenicity of stabilized DS-SOSIP variants after V3-negative selection assessed on a panel of CD4-induced antibodies (17b and 48d, with and without soluble CD4), CD4-binding site antibodies (VRC01, VRC13 and b12), V2-apex-directed antibodies (PGT145, CAP256-VRC26.25), glycan-V3 antibodies (PGT121, PGT128 and 2G12), weakly neutralizing V3-directed antibodies (447-52D, 3074 and 2557, with and without soluble CD4), gp41-gp120 interface antibodies (PGT151, 35022 and 8ANC195) and fusion peptide antibody (VRC34.01).

FIGS. 5A and 5B. Binding of soluble CD4 to stabilized HIV-1 Env trimers as measured by SPR with single-cycle kinetics. (FIG. 5A) SPR curves. For BG505 SOSIP.664, DS-SOSIP and DS-SOSIP.A329P the concentrations of CD4 injected were (nM): 180, 90, 45, 22.5, 11.25. For other DS-SOSIP mutants, the concentrations of CD4 injected were (nM): 1000, 500, 250, 125, 62.5. (FIG. 5B) $K_d$, $k_a$, and $k_d$ values. Values in parentheses report standard errors from fitting data to a 1:1 Langmuir binding model.

SEQUENCES

Figure 1A:
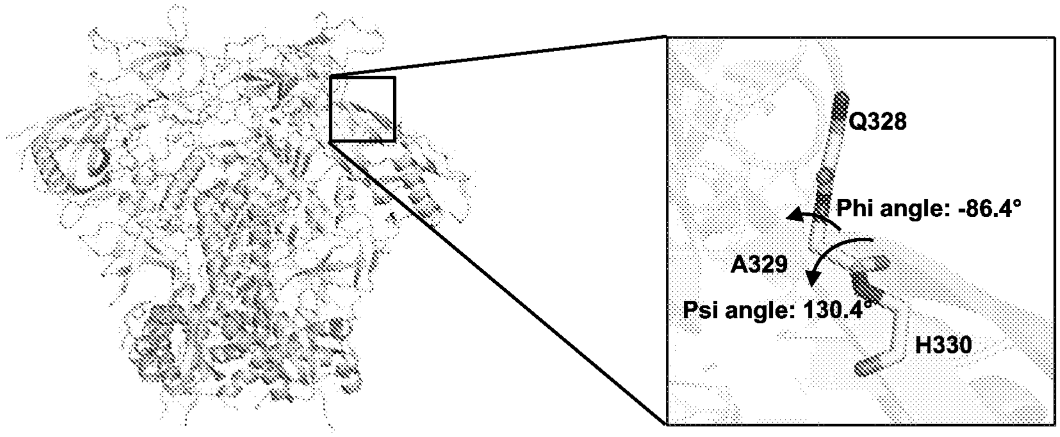
FIGS. 1A-1D. Design of DS-SOSIP.3mut.
Figure 1B:
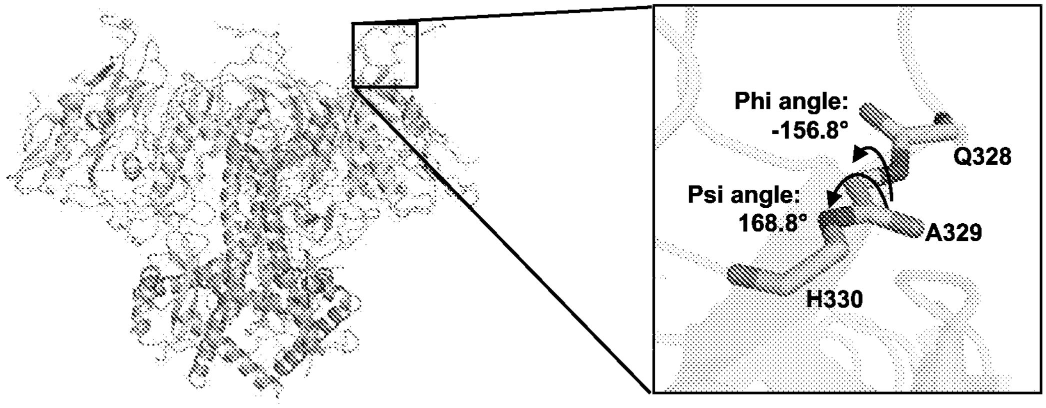
Figure 1C:
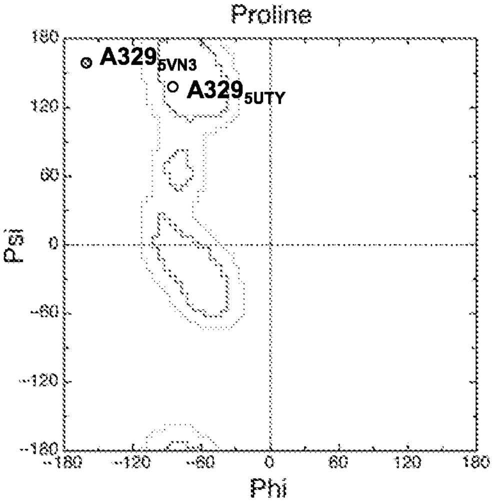
Figure 1D:
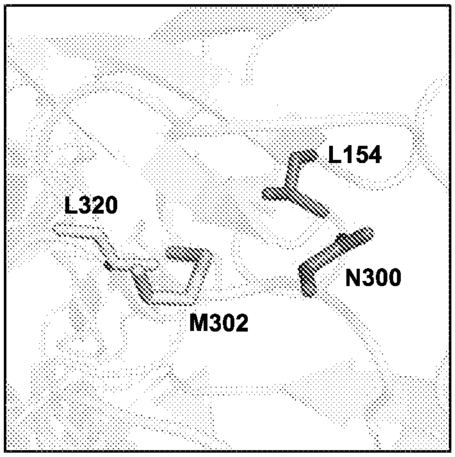

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~136 kb), which was created on Apr. 10, 2020, which is incorporated by reference herein.

DETAILED DESCRIPTION

One approach to elicit broadly neutralizing antibodies against HIV-1 is to stabilize the structurally flexible HIV-1 (Env) trimer in a conformation that displays predominantly broadly neutralizing epitopes, and few to no non-neutralizing epitopes. The prefusion-closed conformation of HIV-1 Env has been identified as one such preferred conformation, and a current leading vaccine candidate is the "BG505.DS-SOSIP.6R.664" ("DS-SOSIP") variant Env ectodomain trimer, which includes two disulfides and an Ile to Pro mutation of strain BG505. This disclosure provides HIV-1 Env ectodomain trimers with additional mutations that further stabilize the Env trimer in the vaccine-preferred prefusion-closed conformation. The disclosed HIV-1 Env ectodomain trimers, such as BG505.DS-SOSIP.3mut.6R.664 (DS-SOSIP.3mut"), provide improved in thermostability and antigenicity relative to prior HIV-1 Env trimers and have utility as HIV-1 immunogens, or in other antigen-specific contexts, such as with B-cell probes. As discussed below, DS-SOSIP.3mut contains three additional mutations relative to DS-SOSIP: a methionine substitution at HIV-1 Env position 302 (N302M), a leucine substitution at HIV-1 Env position 320 (T320L), and a proline substitution at HIV-1 Env positon 329 (A329P). These mutations can be incorporated into other forms of HIV-1 Env (e.g., strains other than BG505, or HIV-1 Env trimers other than those truncated at position 664) to provide improved immunogenic and antigenic characteristics.

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particularly suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

447-52D: A monoclonal antibody that specifically binds to the V3 loop of HIV-1 Env. The person of ordinary skill in the art is familiar with monoclonal antibody 447-52D and with methods of producing this antibody (see, for example, Stanfield et al., Structure, 12, 193-204, which is incorporated by reference herein). The amino acid sequences of the heavy and light variable regions of the 447-52D antibody are known and have been deposited in the Protein Data Bank as Nos. 1Q1J_H (447-52D $V_H$) and 1Q1J_L (447-52D $V_L$), each of which is incorporated by reference herein as present in the database on Oct. 1, 2017).

Adjuvant: A component of an immunogenic composition used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, ASO1, MF59, and ALFQ adjuvants. Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed immunogens.

Administration: The introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid. In some examples, an amino acid in a polypeptide is substituted with an amino acid from a homologous polypeptide, for example, an amino acid in a recombinant Clade A HIV-1 Env polypeptide can be substituted with the corresponding amino acid from a Clade B HIV-1 Env polypeptide.

Antibody: An immunoglobulin, antigen-binding fragment, or derivative thereof, that specifically binds and recognizes an analyte (antigen), such as HIV-1 Env. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$Ed., Springer Press, 2010). Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The framework region of an antibody, that is the combined framework regions of the constituent light and heavy chains, serves to position and align the CDRs in three-dimensional space. The CDRs are primarily responsible for binding to an epitope of an antigen.

Carrier: An immunogenic molecule to which an antigen (such as an HIV-1 Env ectodomain trimer) can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

CD4: Cluster of differentiation factor 4 polypeptide; a T-cell surface protein that mediates interaction with the MHC class II molecule. CD4 also serves as the primary receptor site for HIV-1 on T-cells during HIV-1 infection. CD4 is known to bind to gp120 from HIV-1. The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell* 42:93, 1985).

Conservative variants: "Conservative" amino acid substitutions are those substitutions that do not substantially affect or decrease a function of a protein, such as the ability of the protein to elicit an immune response when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

Non-conservative substitutions are those that reduce an activity or function of the recombinant Env protein, such as the ability to elicit an immune response when administered to a subject. For instance, if an amino acid residue is essential for a function of the protein, even an otherwise conservative substitution may disrupt that activity. Thus, a conservative substitution does not alter the basic function of a protein of interest.

Control: A reference standard. In some embodiments, the control is a negative control sample obtained from a healthy patient. In other embodiments, the control is a positive control sample obtained from a patient diagnosed with HIV-1 infection. In still other embodiments, the control is a historical control or standard reference value or range of values (such as a previously tested control sample, such as a group of HIV-1 patients with known prognosis or outcome, or group of samples that represent baseline or normal values).

A difference between a test sample and a control can be an increase or conversely a decrease. The difference can be a qualitative difference or a quantitative difference, for example, a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Covalent bond: An interatomic bond between two atoms, characterized by the sharing of one or more pairs of electrons by the atoms. The terms "covalently bound" or "covalently linked" refer to making two separate molecules into one contiguous molecule. The terms include reference to joining an antigen (such as an HIV-1 Env ectodomain trimer) either directly or indirectly to a carrier molecule, for example indirectly with an intervening linker molecule, such as a peptide or non-peptide linker.

Degenerate variant: In the context of the present disclosure, a "degenerate variant" refers to a polynucleotide encoding a polypeptide (such as a disclosed immunogen) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detecting: To identify the existence, presence, or fact of something. General methods of detecting may be supplemented with the protocols and reagents disclosed herein. For example, included herein are methods of detecting the level of a protein in a sample or a subject.

Effective amount: An amount of agent, such as an immunogen, that is sufficient to elicit a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to elicit an immune response that inhibits or prevents HIV-1 infection. The HIV-1 infected cells do not need to be completely eliminated or prevented for the composition to be effective. For example, administration of an effective amount of the immunogen can elicit an immune response that decreases the number of HIV-1 infected cells (or prevents the infection of cells) by a desired amount, for example, by at least 50%, at least 60%, at least 70%, at least 80%, at least 90%, at least 95%, at least 98%, or even at least 100% (elimination or prevention of detectable HIV-1 infected cells), as compared to the number of HIV-1 infected cells in the absence of the immunization.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as μL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Non-limiting examples of expression vectors include cosmids, plasmids (e.g., naked or contained in liposomes) and viruses (e.g., lentiviruses, retroviruses, adenoviruses, and adeno-associated viruses) that incorporate the recombinant polynucleotide.

F105: A monoclonal antibody that specifically binds to a conformational epitope on HIV-1 Env that is not present on the prefusion closed conformation. The F105 antibody does not specifically bind to HIV-1 Env in its prefusion closed conformation. The person of ordinary skill in the art is familiar with monoclonal antibody F105 and with methods of producing this antibody (see, for example, Posner et al. *J Acquired Immune Defic Syndr* 6:7-14, 1993; which is incorporated by reference herein). The amino acid sequences of the heavy and light variable regions of the F105 antibody are known and have been deposited in the Protein Data Bank (PDB) as No. 1U6A_H (F105 $V_H$) and 1U6A-L (F105 $V_L$), each of which is incorporated by reference herein as present in the database on Oct. 1, 2017).

Heterologous: A heterologous polypeptide or polynucleotide refers to a polypeptide or polynucleotide derived from a different source or species.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus Type 1 (HIV-1): A retrovirus that causes immunosuppression in humans (HIV-1 disease), and leads to a disease complex known as the acquired immunodeficiency syndrome (AIDS). "HIV-1 disease" refers to a well-recognized constellation of signs and symptoms (including the development of opportunistic infections) in persons who are infected by an HIV-1 virus, as determined by antibody or western blot studies. Laboratory findings associated with this disease include a progressive decline in T cells. Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

HIV-1 envelope protein (Env): The HIV-1 Env protein is initially synthesized as a precursor protein of 845-870 amino acids in size. Individual precursor polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120-gp41 protomers within the homotrimer. The ectodomain (that is, the extracellular portion) of the HIV-1 Env trimer undergoes several structural rearrangements from a prefusion closed conformation that evades antibody recognition, through intermediate conformations that bind to receptors CD4 and co-receptor (either CCR5 or CXCR4), to a postfusion conformation. The HIV-1 Env ectodomain comprises the gp120 protein (approximately HIV-1 Env positions 31-511) and the gp41 ectodomain (approximately HIV-1 Env positions 512-664). An HIV-1 Env ectodomain trimer comprises a protein complex of three HIV-1 Env ectodomains. As used herein "HIV-1 Env ectodomain trimer" includes both soluble trimers (that is, trimers without gp41 transmembrane domain or cytoplasmic tail) and membrane anchored trimers (for example, trimers including a full-length gp41).

Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). The mature gp120 wild-type polypeptide is heavily N-glycosylated, giving rise to an apparent molecular weight of 120 kD. Native gp120 includes five conserved regions (C1-C5) and five regions of high variability (V1-V5).

Mature gp41 includes approximately HIV-1 Env residues 512-860, and includes cytosolic-, transmembrane-, and ectodomains. The gp41 ectodomain (including approximately HIV-1 Env residues 512-644) can interact with gp120 to form an HIV-1 Env protomer that trimerizes to form the HIV-1 Env trimer.

The prefusion closed conformation of the HIV-1 Env ectodomain trimer is a structural conformation adopted by HIV-1 Env ectodomain trimer after cellular processing to a mature prefusion state with distinct gp120 and gp41 polypeptide chains, and before specific binding to the CD4 receptor. The three-dimensional structure of an exemplary HIV-1 Env ectodomain trimer in the prefusion closed conformation is known (see, e.g., Pancera et al., Nature, 514: 455-461, 2014). In the prefusion closed conformation, the HIV-1 Env ectodomain trimer includes a V1V2 domain "cap" at its membrane distal apex, with the V1V2 domain of each Env protomer in the trimer coming together at the membrane distal apex. At the membrane proximal aspect, the prefusion closed conformation of the HIV-1 Env ectodomain trimer includes distinct a6 and a7 helices. CD4 binding causes changes in the conformation of the HIV-1 Env ectodomain trimer, including disruption of the V1V1 domain cap, which "opens" as each V1V2 domain moves outward from the longitudinal axis of the Env trimer, and formation of the HR1 helix, which includes both the a6 and a7 helices (which are no longer distinct). These conformational changes bring the N-terminus of the fusion peptide within close proximity of the target cell membrane, and expose "CD4-induced" epitopes (such as the 17b epitope) that are present in the CD4-bound open conformation, but not the prefusion closed conformation, of the HIV-1 Env ectodomain trimer.

A standardized numbering scheme for HIV-1 Env proteins (the HXB2 numbering scheme) is set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex., which is incorporated by reference herein in its entirety. For reference, the amino acid sequence of HIV-1 Env of HXB2 is set forth as SEQ ID NO: 1 (GENBANK® GI:1906382, incorporated by reference herein).

```
HXB2 (Clade B, SEQ ID NO: 1):
MRVKEKYQHLWRWGWRWGTMLLGMLMICSATEKLWVTVYYGVPVWKEATT

TLFCASDAKAYDTEVHNVWATHACVPTDPNPQEVVLVNVTENFNMWKNDM

VEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSV

ITQACPKVSFEPIPIHYCAPAGFAILKCNNKTFNGTGPCTNVSTVQCTHG

IRPVVSTQLLLNGSLAEEEVVIRSVNFTDNAKTIIVQLNTSVEINCTRPN

NNTRKRIRIQRGPGRAFVTIGKIGNMRQAHCNISRAKWNNTLKQIASKLR

EQFGNNKTIIFKQSSGGDPEIVTHSFNCGGEFFYCNSTQLFNSTWFNSTW

STEGSNNTEGSDTITLPCRIKQIINMWQKVGKAMYAPPISGQIRCSSNIT

GLLLTRDGGNSNNESEIFRPGGGDMRDNWRSELYKYKVVKIEPLGVAPTK

AKRRVVQREKRAVGIGALFLGFLGAAGSTMGAASMTLTVQARQLLSGIVQ

QQNNLLRAIEAQQHLLQLTVWGIKQLQARILAVERYLKDQQLLGIWGCSG

KLICTTAVPWNASWSNKSLEQIWNHTTWMEWDREINNYTSLIHSLIEESQ

NQQEKNEQELLELDKWASLWNWFNITNWLWYIKLFIMIVGGLVGLRIVFA

VLSIVNRVRQGYSPLSFQTHLPTPRGPDRPEGIEEEGGERDRDRSIRLVN

GSLALIWDDLRSLCLFSYHRLRDLLLIVTRIVELLGRRGWEALKYWWNLL

QYWSQELKNSAVSLLNATAIAVAEGTDRVIEVVQGACRAIRHIPRRIRQG

LERILL
```

HIV-1 Env ectodomain trimer stabilized in a prefusion closed conformation: A HIV-1 Env ectodomain trimer having one or more amino acid substitutions, deletions, or insertions compared to a native HIV-1 Env sequence that provide for increased retention of the prefusion closed conformation upon CD4 binding compared to a corresponding native HIV-1 Env sequence. In some embodiments, the HIV-1 Env ectodomain trimer can include one or more cysteine substitutions that allow formation of a non-natural disulfide bond that stabilizes the HIV-1 Env ectodomain trimer in its prefusion closed conformation.

An HIV-1 Env ectodomain trimer stabilized in the prefusion closed conformation has at least 90% (such as at least 95% or at least 99%) reduced transition to the CD4-bound open conformation upon CD4 binding compared to a corresponding native HIV-1 Env sequence. The "stabilization" of the prefusion closed conformation by the one or more amino acid substitutions, deletions, or insertions can be, for example, energetic stabilization (for example, reducing the energy of the prefusion closed conformation relative to the CD4-bound open conformation) and/or kinetic stabilization (for example, reducing the rate of transition from the prefusion closed conformation to the prefusion closed conformation). Additionally, stabilization of the HIV-1 Env ectodomain trimer in the prefusion closed conformation can include an increase in resistance to denaturation compared to a corresponding native HIV-1 Env sequence.

Methods of determining if a HIV-1 Env ectodomain trimer is in the prefusion closed conformation are provided herein, and include (but are not limited to) negative stain electron microscopy and antibody binding assays using a prefusion closed conformation specific antibody, such as VRC26 or PGT145. Methods of determining if a HIV-1 Env ectodomain trimer is in the CD4-bound open conformation are also provided herein, and include (but are not limited to) negative stain electron microscopy and antibody binding assays using a CD4-bound open conformation specific antibody, such as 17b, which binds to a CD4-induced epitope. Transition from the prefusion closed conformation upon CD4 binding can be assayed, for example, by incubating a HIV-1 Env ectodomain trimer of interest that is in the prefusion closed conformation with a molar excess of CD4, and determining if the HIV-1 Env ectodomain trimer retains the prefusion closed conformation (or transitions to the CD4-bound open conformation) by negative stain electron microscopy analysis, or antigenic analysis.

HIV-1 gp140: A recombinant HIV Env polypeptide including gp120 and the gp41 ectodomain, but not the gp41 transmembrane or cytosolic domains. HIV-1 gp140 polypeptides can trimerize to form a soluble HIV-1 Env ectodomain trimer.

HIV-1 gp145: A recombinant HIV Env polypeptide including gp120, the gp41 ectodomain, and the gp41 transmembrane domain. HIV-1 gp145 polypeptides can trimerize to form a membrane-anchored HIV-1 Env ectodomain trimers.

HIV-1 gp160: A recombinant HIV Env polypeptide including gp120 and the entire gp41 protein (ectodomain, transmembrane domain, and cytosolic tail).

HIV-1 neutralizing antibody: An antibody that reduces the infectious titer of HIV-1 by binding to HIV-1 Env protein and inhibiting HIV-1 function. In some embodiments, neutralizing antibodies to HIV-1 can inhibit the infectivity of multiple strains of HIV-1, Tier-2 strain from multiple clades of HIV-1. In some embodiments, a disclosed immunogen can be administered to a subject to elicit an immune response that includes production of antibodies that specifically bind to the HIV-1 Env trimer and neutralize Tier-2 strains of HIV-1 from multiple HIV-1 clades.

Immunogenic conjugate: A composition composed of at least two heterologous molecules (such as an HIV-1 Env trimer and a carrier, such as a protein carrier) linked together that stimulates or elicits an immune response to a molecule in the conjugate in a vertebrate. In some embodiments where the conjugate include a viral antigen, the immune response is protective in that it enables the vertebrate animal to better resist infection from the virus from which the antigen is derived.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to treatment of a subject with a "prime" immunogen to induce an immune response that is subsequently "boosted" with a boost immunogen. Together, the prime and boost immunizations produce the desired immune response in the subject. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A protein or a portion thereof that is capable of inducing an immune response in a mammal, such as a mammal infected or at risk of infection with a pathogen.

Immunogenic composition: A composition comprising a disclosed immunogen, or a nucleic acid molecule or vector encoding a disclosed immunogen, that elicits a measurable CTL response against the immunogen, or elicits a measurable B cell response (such as production of antibodies) against the immunogen, when administered to a subject. It further refers to isolated nucleic acids encoding an immunogen, such as a nucleic acid that can be used to express the immunogen (and thus be used to elicit an immune response against this immunogen). For in vivo use, the immunogenic composition will typically include the protein or nucleic acid molecule in a pharmaceutically acceptable carrier and may also include other agents, such as an adjuvant.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker". In several embodiments, linked components are associated in a chemical or physical manner so that the components are not freely dispersible from one another, at least until contacting a cell, such as an immune cell.

Linker: One or more molecules or groups of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

PGT121, PGT122, and PGT123: A family of neutralizing monoclonal antibodies that specifically bind to the V1/V2 and V3 regions of HIV-1 Env and can inhibit HIV-1 infection of target cells. The person of ordinary skill in the art is familiar with the PGT121, PGT122, and PGT123 mAbs and with methods of producing them (see, for example, Walker et al., Nature, 477:466-470, 2011, and Int. Pub. No. WO 2012/030904, each of which is incorporated by reference herein). The amino acid sequences of the heavy and light variable regions of the PGT121, PGT122, and PGT123 antibodies are known and have been deposited in GenBank as Nos. AEN14390.1 (PGT121 $V_H$), AEN14407.1 (PGT121 $V_L$), JN201895.1 (PGT122 $V_H$), JN201912.1 (PGT122 $V_L$), JN201896.1 (PGT123 $V_H$), and JN201913.1 (PGT123 $V_L$), each of which is incorporated by reference herein as present in the database on Oct. 1, 2017) PGT141, PGT142, PGT143, and PGT145: A family of broadly neutralizing monoclonal antibodies that specifically bind to the V1/V2 domain of the HIV-1 Env ectodomain trimer in its prefusion closed conformation, and which can inhibit HIV-1 infection of target cells. The person of ordinary skill in the art is familiar with the PGT141, PGT142, PGT143, and PGT145 mAbs and with methods of producing them (see, for example, Walker et al., Nature, 477:466-470, 2011, and Int. Pub. No. WO2012/030904, each of which is incorporated by reference herein). The amino acid sequences of the heavy and light variable regions of the PGT141, PGT142, PGT143, PGT144, and PGT145 mAbs are known and have been deposited in GenBank as Nos. JN201906.1 (PGT141 $V_H$), JN201923.1 (PGT141 $V_L$), JN201907.1 (PGT142 $V_H$), JN201924.1 (PGT142 $V_L$), JN201908.1 (PGT143 $V_H$), JN201925.1 (PGT143 $V_L$), JN201909.1 (PGT144 $V_H$), JN201926.1 (PGT144 $V_L$), JN201910.1 (PGT145 $V_H$), and JN201927.1 (PGT145 $V_L$), each of which is incorporated by reference herein as present in the database on Oct. 1, 2017).

PGT151: A broadly neutralizing monoclonal antibody that specifically bind to the gp120/gp41 interface of HIV-1 Env in its prefusion mature (cleaved) conformation, and which can inhibit HIV-1 infection of target cells. The person of ordinary skill in the art is familiar with the PGT151 antibody and with methods of producing this antibody (see, for example, Blattner et al., Immunity, 40, 669-680, 2014, and Falkowska et al., Immunity, 40, 657-668, 2014, each of which is incorporated by reference herein). The amino acid sequences of the heavy and light variable regions of the PGT151 mAb are known and have been deposited in GenBank as Nos. KJ700282.1 (PGT151 $V_H$) and KJ700290.1 (PGT151 $V_L$), each of which is incorporated by reference herein as present in the database on Oct. 1, 2017).

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In particular embodiments, suitable for administration to a subject the carrier may be sterile, and/or suspended or otherwise contained in a unit dosage form containing one or more measured doses of the composition suitable to elicit the desired anti-HIV-1 immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost immunization: An immunotherapy including administration of multiple immunogens over a period of time to elicit the desired immune response.

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, *Y. Int. J. Mol. Sci.,* 12:5406-5421, 2011, incorporated by reference herein), encapsulin nanoparticles (see, e.g., Sutter et al., *Nature Struct. and Mol. Biol.,* 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a protomer of a disclosed recombinant HIV-1 Env ectodomain and self-assemble into a protein nanoparticle presenting trimers of the protomers on its surface, which can be administered to a subject to stimulate an immune response to the HIV-1 Env ectodomain trimer.

Recombinant: A recombinant nucleic acid is one that has a sequence that is not naturally occurring or has a sequence that is made by an artificial combination of two otherwise separated segments of sequence. This artificial combination can be accomplished, for example, the artificial manipulation of isolated segments of nucleic acids, for example, using genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-30 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). An exemplary signal peptide sequence is set forth as residues 1-28 of SEQ ID NO: 4.

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, gp120) and does not bind in a significant amount to other proteins or polysaccharides present in the sample or subject. Specific binding can be determined by standard methods. A first protein or antibody specifically binds to a target protein when the interaction has a $K_D$ of less than $10^{-7}$ Molar, such as less than $10^{-8}$ Molar, less than $10^{-9}$, or even less than $10^{-10}$ Molar.

Subject: Living multicellular vertebrate organisms, a category that includes human and non-human mammals. In an example, a subject is a human. In an additional example, a subject is selected that is in need of inhibiting of an HIV-1 infection. For example, the subject is either uninfected and at risk of HIV-1 infection or is infected in need of treatment.

Transmembrane domain: An amino acid sequence that inserts into a lipid bilayer, such as the lipid bilayer of a cell or virus or virus-like particle. A transmembrane domain can be used to anchor an antigen to a membrane.

Under conditions sufficient for: A phrase that is used to describe any environment that permits a desired activity.

Vaccine: A pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine reduces the severity of the symptoms associated with HIV-1 infection and/or decreases the viral load compared to a control. In another non-limiting example, a vaccine reduces HIV-1 infection compared to a control.

Vector: An entity containing a DNA or RNA molecule bearing a promoter(s) that is operationally linked to the coding sequence of an immunogenic protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses.

A non-limiting example of a DNA-based expression vector is pCDNA3.1, which can include includes a mammalian expression enhancer and promoter (such as a CMV promoter). Non-limiting examples of viral vectors include adeno-associated virus (AAV) vectors as well as Poxvirus vector (e.g., Vaccinia, MVA, avian Pox, or Adenovirus).

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. The presence of VLPs following recombinant expression of viral proteins can be detected using conventional techniques, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.,* 2011; Schneider-Ohrum and Ross, *Curr. Top. Microbiol. Immunol.,* 354: 53073, 2012).

VRC01: A broadly neutralizing monoclonal antibody that specifically binds to the CD4 binding site on HIV-1 Env and can inhibit HIV-1 infection of target cells. The person of ordinary skill in the art is familiar with the VRC01 mAb and with methods of its use and production (see, for example, Wu et al., Science, 329(5993):856-861, 2010, and PCT publication WO2012/154312, each of which is incorporated by reference herein). The amino acid sequences of the heavy and light variable regions of the VRC01 mAb are known and have been deposited in GenBank as Nos. ADF47181.1 (VRC01 $V_H$) and ADF47184.1 (VRC01 $V_L$), each of which is incorporated by reference herein).

II. Immunogens

Embodiments of immunogens comprising a recombinant HIV-1 Env ectodomain trimer that is stabilized in a prefusion closed conformation are provided below. The disclosed HIV-1 Env ectodomain trimer can be used as an immunogen in soluble or membrane-anchored forms, and also can be incorporated into a protein nanoparticle, conjugated to a carrier, and included in a viral-like particle (VLP). The immunogens can be used to generate a neutralizing immune response to HIV-1 in a subject, for example, to treat or prevent an HIV-1 infection in the subject.

Recombinant HIV-1 Env Ectodomain Trimers

Provided herein are recombinant HIV-1 Env ectodomain trimers comprising protomers (each comprising a gp120 protein and a gp41 ectodomain) that are modified from a native form (e.g., by introduction of one or more amino acid substitutions) to be stabilized in a prefusion closed conformation. The recombinant HIV-1 Env ectodomain trimers have reduced binding to CD4 compared to native HIV-1 Env ectodomain trimers, but retain binding affinity for broadly neutralizing antibodies, such as PG9, PG16, VRC26, PGT145, VRC01, VRC07, N6, 35022, 8ANC195, PGT151, and/or PGT121. Administration of an effective amount of a disclosed recombinant HIV-1 Env ectodomain trimer to a subject elicits a neutralizing immune response to HIV-1 in the subject.

The protomers of the disclosed recombinant HIV-1 Env ectodomain trimer includes several amino acid substitutions that stabilize the trimer in the prefusion closed conformation. These substitutions comprise (but are not limited to):

1) the "SOS" substitutions, which include cysteine substitutions at HIV-1 Env positions 501 and 605 (for example, by A501C and T605C substitutions) to form a non-natural intra-protomer disulfide bond,
2) the "IP" substitution, which is a proline substitution at HIV-1 Env position 559 (for example, by an I559P substitution);
3) the "DS" substitutions, which include cysteine substitutions at HIV-1 Env positions 201 and 433 (e.g., by introduction of I201C and A433C substitutions) to form a non-natural intra-protomer disulfide bond; and
4) a proline substitution at HIV-1 Env positon 329 (for example, by an A329P substitution).

The presence of the non-natural disulfide bonds between positions 501 and 605, and positions 201 and 433, and the proline substitutions at positions 329 and 559 contributes to the stabilization of the HIV-1 Env ectodomain in the prefusion closed conformation.

In some embodiments, the protomers of the disclosed recombinant HIV-1 Env ectodomain trimer additionally include a methionine substitution at HIV-1 Env position 302, and/or a leucine substitution at HIV-1 Env position 320. The presence of one or both of these amino acid substitutions contributes to the stabilization of the HIV-1 Env ectodomain in the prefusion closed conformation.

In an embodiment, the protomers of the disclosed recombinant HIV-1 Env ectodomain trimer comprise the "SOS" substitutions, the "IP" substitution, the "DS" substitutions, the proline substitution at HIV-1 Env positon 329, the methionine substitution at HIV-1 Env position 302, and the leucine substitution at HIV-1 Env position 320.

In some embodiments, the recombinant gp120 protein in any of the disclosed HIV-1 Env ectodomain trimers disclosed herein can further include an N-linked glycosylation site at HIV-1 Env position 332 (if not already present on the ectodomain). For example, by T332N substitution in the case of BG505-based immunogens. The presence of the glycosylation site at N332 allows for binding by 2G12 antibody.

In some embodiments, the recombinant gp120 protein in any of the disclosed HIV-1 Env ectodomain trimers disclosed herein can include a lysine residue at HIV-1 Env position 168 (if not already present on the ectodomain). For example, the lysine residue can be added by amino acid substitution (such as an E168K substitution in the case of the JR-FL based immunogens). The presence of the lysine residue at position 168 allows for binding of particular broadly neutralizing antibodies to the V1V2 loop of gp120.

Native HIV-1 Env sequences include a furin cleavage site between positions 508 and 512 (HXB2 numbering), that separates gp120 and gp41. Any of the disclosed recombinant HIV-1 Env ectodomains can further include an enhanced cleavage site between gp120 and gp41 proteins.

In some embodiments, the enhanced cleavage site can include substitution of any one of RRRRRR (SEQ ID NO: 8), GRRRRRR (SEQ ID NO: 27), GGSGRRRRRR (SEQ ID NO: 28), GRRRRRRRRR (SEQ ID NO: 29), or GNSTHKQLTHHMRRRRRR (SEQ ID NO: 30) for the amino acids of a gp120/gp41 furin cleavage site. In an example, the enhanced cleavage cite can include, for example, substitution of six arginine resides for the four residues of the native cleavage site (e.g., REKR (SEQ ID NO: 7) to RRRRRR (SEQ ID NO: 8). It will be understood that protease cleavage of the furin or enhanced cleavage site separating gp120 and gp41 can remove a few amino acids from either end of the cleavage site.

In some embodiments, any of the HIV-1 Env ectodomain trimers including the recombinant gp120 proteins disclosed herein can include mutations to add an N-linked glycan sequon at position 504, position 661, or positions 504 and 661, to increase glycosylation of the membrane proximal region of the ectodomain.

In additional embodiments, the recombinant HIV-1 Env ectodomain trimer can be further modified by removing N-linked glycosylation sites near the HIV-1 Env fusion peptide in the trimer (such as N88, N230, N241, and/or N611 glycosylation sites, HXB2 numbering). Selective deglycosylation of these N-linked glycosylation sites increases exposure of the HIV-1 Env fusion peptide to the immune system to promote a neutralizing immune response targeting the fusion peptide. The amino acid substitutions to remove the glycosylation site can include a substitution of the asparagine residue or the serine/threonine residue of the N-X-[S/T] consensus. Typical substitutions include an asparagine to glutamine substitution, a serine to cysteine or methionine substitution, or a threonine to cysteine or methionine substitution, although any substitution that removes the N-linked glycosylation site can be used if it does not disrupt the structure (for example, prefusion closed conformation) or function (for example, VRC34 binding) of the recombinant HIV-1 Env ectodomain trimer.

Any of the HIV-1 Env trimers disclosed herein can further comprise one or more amino acid substitutions to the fusion peptide sequence (e.g., HIV-1 Env residues 512-519) to change the sequence to that of the fusion peptide from a heterologous HIV-1 strain. For example, the native fusion peptide sequence of BG505 is AVGIGAVF (residues 482-489 of SEQ ID NO: 2); this sequence could be modified to match that of other HIV-1 strains. To generate a set of HIV-1 Env trimer with diverse fusion peptide sequences, the first eight amino acid residues of the BG505 fusion peptide can be mutated as needed to match the fusion peptide sequence of other HIV-1 strains of interest. In some embodiments, a "cocktail" of soluble HIV-1 Env trimers is provided that contain fusion peptide sequence representation many different HIV-1 strains.

The prefusion closed conformation of the HIV-1 Env trimer has been disclosed, for example, in Pancera et al., *Nature,* 514, 455-461, 2014 and PCT App. No. PCT/US2015/048729, each of which is incorporated by reference herein in its entirety. In some embodiments, the protomers of the HIV-1 Env ectodomain trimers disclosed herein can further include one of more modifications as disclosed in PCT App. No. PCT/US2015/048729 to stabilize the recombinant HIV-1 Env ectodomain trimer in the prefusion closed conformation. For example, the HIV-1 Env ectodomain trimer can include a prefusion closed conformation wherein the V1V2 domain of each Env ectodomain protomer in the trimer comes together at the membrane distal apex. At the membrane proximal aspect, the HIV-1 Env ectodomain trimer in the prefusion closed conformation includes distinct a6 and a7 helices; the a7 helix does not start until after residue 570. For example, in the prefusion closed conformation, the interprotomer distance between residues 200 and 313 can be less than 5 Angstroms.

HIV-1 can be classified into four groups: the "major" group M, the "outlier" group O, group N, and group P. Within group M, there are several genetically distinct clades (or subtypes) of HIV-1. The disclosed recombinant HIV-1 Env proteins can be derived from any type of HIV, such as groups M, N, O, or P, or clade, such as clade A, B, C, D, F, G, H, J, or K, and the like. HIV-1 Env proteins from the different HIV-1 clades, as well as nucleic acid sequences encoding such proteins and methods for the manipulation and insertion of such nucleic acid sequences into vectors, are known (see, e.g., HIV Sequence Compendium, Division of AIDS, National Institute of Allergy and Infectious Diseases (2013); HIV Sequence Database (hiv-web.lanl.gov/content/hiv-db/mainpage.html); see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). Exemplary native HIV-1 Env protein sequences are available in the HIV Sequence Database (hiv-web.lanl.gov/content/hiv-db/mainpage.html).

In some embodiments, any of the HIV-1 Env ectodomain trimers including the recombinant gp120 proteins disclosed herein can include an amino acid sequence of a native gp120 protein or HIV-1 Env protein, for example, from genetic subtype A-F as available in the HIV Sequence Database (hiv-web.lanl.gov/content/hiv-db/mainpage.html) or as set forth in Table 1, or an amino acid sequence at least 90% (such as at least 95%, at least 96%, at least 97%, at least 98% or at least 99%) identical thereto that has been modified by one or more amino acid substitutions and/or insertions as discussed herein, for example, to stabilize the recombinant gp120 protein or HIV-1 Env ectodomain trimer in the prefusion closed conformation.

In some examples, the protomers of the HIV-1 Env ectodomain trimer comprise the sequence of BG505.DS-SOSIP.6R.664 modified to include one or more additional amino acid substitutions including the A329P substitution to stabilize a HIV-1 Env ectodomain trimer including the protomers in the prefusion closed conformation. The BG505.DS-SOSIP.6R.664 sequence is set forth as:

```
BG505 DS-SOSIP.6R.664 (BG505.DS-SOSIP.6R.664.)
                                        (SEQ ID NO: 2)
AENLWVTVYYGVPVWKDAETTLFCASDAKAYETEKHNVWATHACVPTDPN

PQEIHLENVTEEFNMWKNNMVEQMHTDIISLWDQSLKPCVKLTPLCVTLQ

CTNVTNNITDDMRGELKNCSFNMTTELRDKKQKVYSLFYRLDVVQINENQ

GNRSNNSNKEYRLINCNTSACTQACPKVSFEPIPIHYCAPAGFAILKCKD

KKFNGTGPCPSVSTVQCTHGIKPVVSTQLLLNGSLAEEEVMIRSENITNN

AKNILVQFNTPVQINCTRPNNNTRKSIRIGPGQAFYATGDIIGDIRQAHC

NVSKATWNETLGKVVKQLRKHFGNNTIIRFANSSGGDLEVTTHSFNCGGE

FFYCNTSGLFNSTWISNTSVQGSNSTGSNDSITLPCRIKQIINMWQRIGQ

CMYAPPIQGVIRCVSNITGLILTRDGGSTNSTTETFRPGGGDMRDNWRSE

LYKYKVVKIEPLGVAPTRCKRRVVGRRRRRRAVGIGAVFLGFLGAAGSTM

GAASMTLTVQARNLLSGIVQQQSNLLRAPEAQQHLLKLTVWGIKQLQARV

LAVERYLRDQQLLGIWGCSGKLICCTNVPWNSSWSNRNLSEIWDNMTWLQ

WDKEISNYTQIIYGLLEESQNQQEKNEQDLLALD
```

The above BG505.DS-SOSIP.6R.664 sequence is truncated at position 664, and includes T332N and 6R substitutions. Membrane-bound forms of this sequence can be readily generated by attaching a transmembrane domain and cytosolic tail to C-terminal residue of the sequence.

In some embodiments, the protomers of the HIV-1 Env ectodomain trimer comprise an amino acid sequence set forth as:

```
BG505.DS-SOSIP.3mut.6R.664
                                        (SEQ ID NO: 3)
AENLWVTVYYGVPVWKDAETTLFCASDAKAYETEKHNVWATHACVPTDPN

PQEIHLENVTEEFNMWKNNMVEQMHTDIISLWDQSLKPCVKLTPLCVTLQ

CTNVTNNITDDMRGELKNCSFNMTTELRDKKQKVYSLFYRLDVVQINENQ

GNRSNNSNKEYRLINCNTSACTQACPKVSFEPIPIHYCAPAGFAILKCKD

KKFNGTGPCPSVSTVQCTHGIKPVVSTQLLLNGSLAEEEVMIRSENITNN

AKNILVQFNTPVQINCTRPNNMTRKSIRIGPGQAFYALGDIIGDIRQPHC

NVSKATWNETLGKVVKQLRKHFGNNTIIRFANSSGGDLEVTTHSFNCGGE

FFYCNTSGLFNSTWISNTSVQGSNSTGSNDSITLPCRIKQIINMWQRIGQ

CMYAPPIQGVIRCVSNITGLILTRDGGSTNSTTETFRPGGGDMRDNWRSE

LYKYKVVKIEPLGVAPTRCKRRVVGRRRRRRAVGIGAVFLGFLGAAGSTM

GAASMTLTVQARNLLSGIVQQQSNLLRAPEAQQHLLKLTVWGIKQLQARV
```

-continued

LAVERYLRDQQLLGIWGCSGKLICCTNVPWNSSWSNRNLSEIWDNMTWLQ

WDKEISNYTQIIYGLLEESQNQQEKNEQDLLALD

SEQ ID NO: 4 provides the amino acid sequence of BG505.DS-SOSIP.3mut.6R.664 with a signal peptide sequence (e.g., for cellular expression):

SRATMPMGSLQPLATLYLLGMLVASVLAAENLWVTVYYGVPVWKDAETTL

FCASDAKAYETEKHNVWATHACVPTDPNPQEIHLENVTEEFNMWKNNMVE

QMHTDIISLWDQSLKPCVKLTPLCVTLQCTNVTNNITDDMRGELKNCSFN

MTTELRDKKQKVYSLFYRLDVVQINENQGNRSNNSNKEYRLINCNTSACT

QACPKVSFEPIPIHYCAPAGFAILKCKDKKFNGTGPCPSVSTVQCTHGIK

PVVSTQLLLNGSLAEEEVMIRSENITNNAKNILVQFNTPVQINCTRPNNM

TRKSIRIGPGQAFYALGDIIGDIRQPHCNVSKATWNETLGKVVKQLRKHF

GNNTIIRFANSSGGDLEVTTHSFNCGGEFFYCNTSGLFNSTWISNTSVQG

SNSTGSNDSITLPCRIKQIINMWQRIGQCMYAPPIQGVIRCVSNITGLIL

TRDGGSTNSTTETFRPGGGDMRDNWRSELYKYKVVKIEPLGVAPTRCKRR

VVGRRRRRRAVGIGAVFLGFLGAAGSTMGAASMTLTVQARNLLSGIVQQQ

SNLLRAPEAQQHLLKLTVWGIKQLQARVLAVERYLRDQQLLGIWGCSGKL

ICCTNVPWNSSWSNRNLSEIWDNMTWLQWDKEISNYTQIIYGLLEESQNQ

QEKNEQDLLALD

In some embodiments, the protomers of the HIV-1 Env ectodomain trimer comprise an amino acid sequence set forth as:

CAP256-wk34c80-RnS-3mut-2G_FP8v2
(SEQ ID NO: 19)

GLWVTVYYGVPVWREAKTTLFCASDAKSYEKEVHNVWATHACVPTDPNPQ

ELVLENVTENFNMWKNDMVDQMHEDIISLWDQSLKPCVKLTPLCVTLNCS

DAKVNATYKGTREEIKNCSFNATTELRDKKRREYALFYRLDIVPLSGEGN

NNSEYRLINCNTSVITQICPKVTFDPIPIHYCAPAGYAILKCNNKTFNGT

GPCNNVSTVQCTHGIKPVVSTQLLLNGSLAEEEIIIRSENLTDNVKTIIV

HLNESVEITCTRPNNMTRKSVRIGPGQTFYALGDIIGDIRQPHCNISEIK

WEKTLQRVSEKLREHFNKTIIFNQSSGGDLEITTHSFNCGGEFFYCNTSD

LFFNKTFNETYSTGSNSTNSTITLPCRIKQIINMWQEVGRAMYAPPIAGN

ITCKSNITGLLLTRDGGGNNSTKETFRPGGGNMRDNWRSELYKYKVVEVK

PLGIAPTECNRTVVQRRRRRRAVGLGAVFLGFLGAAGSTMGAASNTLTVQ

ARQLLSGIVQQQSNLLRAPEAQQHMLQLGVWGFKQLQARVLAIERYLEVQ

QLLGMWGCSGKLICCTNVPWNSSWSNKTYNEIWDNMTWMQWDREIGNYTD

TIYKLLEVSQFQQEINEKDNLTLD

The above CAP256-wk34c80-RnS-3mut-2G_FP8v2 sequence is truncated at position 664, and includes the SOSIP, 3mut, and 6R substitutions (among others). Membrane-bound forms of this sequence can be readily generated by attaching a transmembrane domain and cytosolic tail to C-terminal residue of the sequence.

SEQ ID NO: 20 provides the amino acid sequence of CAP256-wk34c80-RnS-3mut-2G_FP8v2 with a signal peptide sequence (e.g., for cellular expression):

MDSKGSSQKGSRLLLLLVVSNLLLPQGVLAGLWVTVYYGVPVWREAKTTL

FCASDAKSYEKEVHNVWATHACVPTDPNPQELVLENVTENFNMWKNDMVD

QMHEDIISLWDQSLKPCVKLTPLCVTLNCSDAKVNATYKGTREEIKNCSF

NATTELRDKKRREYALFYRLDIVPLSGEGNNNSEYRLINCNTSVITQICP

KVTFDPIPIHYCAPAGYAILKCNNKTFNGTGPCNNVSTVQCTHGIKPVVS

TQLLLNGSLAEEEIIIRSENLTDNVKTIIVHLNESVEITCTRPNNMTRKS

VRIGPGQTFYALGDIIGDIRQPHCNISEIKWEKTLQRVSEKLREHFNKTI

IFNQSSGGDLEITTHSFNCGGEFFYCNTSDLFFNKTFNETYSTGSNSTNS

TITLPCRIKQIINMWQEVGRAMYAPPIAGNITCKSNITGLLLTRDGGGNN

STKETFRPGGGNMRDNWRSELYKYKVVEVKPLGIAPTECNRTVVQRRRRR

RAVGLGAVFLGFLGAAGSTMGAASNTLTVQARQLLSGIVQQQSNLLRAPE

AQQHMLQLGVWGFKQLQARVLAIERYLEVQQLLGMWGCSGKLICCTNVPW

NSSWSNKTYNEIWDNMTWMQWDREIGNYTDTIYKLLEVSQFQQEINEKDN

LTLD

In some embodiments, the protomers of the HIV-1 Env ectodomain trimer comprise an amino acid sequence set forth as:

ConC_Base0_3mut_2G_FP8v2
(SEQ ID NO: 21)

NLWVTVYYGVPVWKEAKTTLFCASDAKAYEKEVHNVWATHACVPTDPNPQ

EMVLENVTENFNMWKNDMVDQMHEDIISLWDQSLKPCVKLTPLCVTLNCT

NVNVTNTNNNNMKEEMKNCSFNTTTEIRDKKQKEYALFYRLDIVPLNENS

SEYRLINCNTSTITQICPKVSFDPIPIHYCAPAGYAILKCNNKTFNGTGP

CNNVSTVQCTHGIKPVVSTQLLLNGSLAEEEIIIRSENLTDNAKTIIVHL

NESVEINCTRPNNMTRKSIRIGPGQTFYALGDIIGDIRQPHCNISEAKWN

KTLQRVKKKLKEHFPNKTIKFAPSSGGDLEITTHSFNCRGEFFYCNTSKL

FNSTYNNTTSNSTITLPCRIKQIINMWQEVGRAMYAPPIAGNITCKSNIT

GLLLTRDGGNNNNNTETFRPGGGDMRDNWRSELYKYKVVEIKPLGIAPTK

CKRRVVERRRRRRAVGLGAVFLGFLGAAGSTMGAASNTLTVQARQLLSGI

VQQQSNLLRAPEAQQHMLQLGVWGFKQLQARVLAIERYLEVQQLLGIWGC

SGKLICCTAVPWNSSWSNKSQEDIWDNMTWMQWDREIGNYTDTIYRLLEE

SQFQQEINEKDLLALD

The above ConC_Base0_3mut_2G_FP8v2 sequence is truncated at position 664, and includes the SOSIP, 3mut, and 6R substitutions (among others). Membrane-bound forms of this sequence can be readily generated by attaching a transmembrane domain and cytosolic tail to C-terminal residue of the sequence.

SEQ ID NO: 22 provides the amino acid sequence of ConC_Base0_3mut_2G_FP8v2 with a signal peptide sequence (e.g., for cellular expression):

MDSKGSSQKGSRLLLLLVVSNLLLPQGVLANLWVTVYYGVPVWKEAKTTL
FCASDAKAYEKEVHNVWATHACVPTDPNPQEMVLENVTENFNMWKNDMVD
QMHEDIISLWDQSLKPCVKLTPLCVTLNCTNVNVTNTNNNNMKEEMKNCS
FNTTTEIRDKKQKEYALFYRLDIVPLNENSSEYRLINCNTSTITQICPKV
SFDPIPIHYCAPAGYAILKCNNKTFNGTGPCNNVSTVQCTHGIKPVVSTQ
LLLNGSLAEEEIIIRSENLTDNAKTIIVHLNESVEINCTRPNNMTRKSIR
IGPGQTFYALGDIIGDIRQPHCNISEAKWNKTLQRVKKKLKEHFPNKTIK
FAPSSGGDLEITTHSFNCRGEFFYCNTSKLFNSTYNNTTSNSTITLPCRI
KQIINMWQEVGRAMYAPPIAGNITCKSNITGLLLTRDGGNNNNNTETFRP
GGGDMRDNWRSELYKYKVVEIKPLGIAPTKCKRRVVERRRRRRAVGLGAV
FLGFLGAAGSTMGAASNTLTVQARQLLSGIVQQQSNLLRAPEAQQHMLQL
GVWGFKQLQARVLAIERYLEVQQLLGIWGCSGKLICCTAVPWNSSWSNKS
QEDIWDNMTWMQWDREIGNYTDTIYRLLEESQFQQEINEKDLLALD

The CAP256-wk34c80-RnS-3mut-2G_FP8v2 and ConC_Base0_3mut_2G_FP8v2 sequences do not include the "DS" substitutions. In some embodiments, the protomers of the HIV-1 Env ectodomain trimer comprise the CAP256-wk34c80-RnS-3mut-2G_FP8v2 and ConC_Base0_3mut_2G_FP8v2 amino acid sequence further modified to include the "DS" substitutions. For example, in some embodiments, the protomers of the HIV-1 Env ectodomain trimer comprise the amino acid sequence set forth as one of:

CAP256-wk34c80-RnS-3mut-2G_FP8v2-DS
(SEQ ID NO: 23)
GLWVTVYYGVPVWREAKTTLFCASDAKSYEKEVHNVWATHACVPTDPNPQ
ELVLENVTENFNMWKNDMVDQMHEDIISLWDQSLKPCVKLTPLCVTLNCS
DAKVNATYKGTREEIKNCSFNATTELRDKKRREYALFYRLDIVPLSGEGN
NNSEYRLINCNTSVCTQICPKVTFDPIPIHYCAPAGYAILKCNNKTFNGT
GPCNNVSTVQCTHGIKPVVSTQLLLNGSLAEEEIIIRSENLTDNVKTIIV
HLNESVEITCTRPNNMTRKSVRIGPGQTFYALGDIIGDIRQPHCNISEIK
WEKTLQRVSEKLREHFNKTIIFNQSSGGDLEITTHSFNCGGEFFYCNTSD
LFFNKTFNETYSTGSNSTNSTITLPCRIKQIINMWQEVGRCMYAPPIAGN
ITCKSNITGLLLTRDGGGNNSTKETFRPGGGNMRDNWRSELYKYKVVEVK
PLGIAPTECNRTVVQRRRRRRAVGLGAVFLGFLGAAGSTMGAASNTLTVQ
ARQLLSGIVQQQSNLLRAPEAQQHMLQLGVWGFKQLQARVLAIERYLEVQ
QLLGMWGCSGKLICCTNVPWNSSWSNKTYNEIWDNMTWMQWDREIGNYTD
TIYKLLEVSQFQQEINEKDNLTLD ConC_Base0_3mut_2G_FP8v2-DS
(SEQ ID NO: 24)
NLWVTVYYGVPVWKEAKTTLFCASDAKAYEKEVHNVWATHACVPTDPNPQ
EMVLENVTENFNMWKNDMVDQMHEDIISLWDQSLKPCVKLTPLCVTLNCT
NVNVTNTNNNNMKEEMKNCSFNTTTEIRDKKQKEYALFYRLDIVPLNENS
SEYRLINCNTSTCTQICPKVSFDPIPIHYCAPAGYAILKCNNKTFNGTGP
CNNVSTVQCTHGIKPVVSTQLLLNGSLAEEEIIIRSENLTDNAKTIIVHL -continued NESVEINCTRPNNMTRKSIRIGPGQTFYALGDIIGDIRQPHCNISEAKWN
KTLQRVKKKLKEHFPNKTIKFAPSSGGDLEITTHSFNCRGEFFYCNTSKL
FNSTYNNTTSNSTITLPCRIKQIINMWQEVGRCMYAPPIAGNITCKSNIT
GLLLTRDGGNNNNNTETFRPGGGDMRDNWRSELYKYKVVEIKPLGIAPTK
CKRRVVERRRRRRAVGLGAVFLGFLGAAGSTMGAASNTLTVQARQLLSGI
VQQQSNLLRAPEAQQHMLQLGVWGFKQLQARVLAIERYLEVQQLLGIWGC
SGKLICCTAVPWNSSWSNKSQEDIWDNMTWMQWDREIGNYTDTIYRLLEE
SQFQQEINEKDLLALD SEQ ID NO: 25 provides the amino acid sequence of CAP256-wk34c80-RnS-3mut-2G_FP8v2-DS with a signal peptide sequence (e.g., for cellular expression):

MDSKGSSQKGSRLLLLLVVSNLLLPQGVLAGLWVTVYYGVPVWREAKTTL
FCASDAKSYEKEVHNVWATHACVPTDPNPQELVLENVTENFNMWKNDMVD
QMHEDIISLWDQSLKPCVKLTPLCVTLNCSDAKVNATYKGTREEIKNCSF
NATTELRDKKRREYALFYRLDIVPLSGEGNNNSEYRLINCNTSVCTQICP
KVTFDPIPIHYCAPAGYAILKCNNKTFNGTGPCNNVSTVQCTHGIKPVVS
TQLLLNGSLAEEEIIIRSENLTDNVKTIIVHLNESVEITCTRPNNMTRKS
VRIGPGQTFYALGDIIGDIRQPHCNISEIKWEKTLQRVSEKLREHFNKTI
IFNQSSGGDLEITTHSFNCGGEFFYCNTSDLFFNKTFNETYSTGSNSTNS
TITLPCRIKQIINMWQEVGRCMYAPPIAGNITCKSNITGLLLTRDGGGNN
STKETFRPGGGNMRDNWRSELYKYKVVEVKPLGIAPTECNRTVVQRRRRR
RAVGLGAVFLGFLGAAGSTMGAASNTLTVQARQLLSGIVQQQSNLLRAPE
AQQHMLQLGVWGFKQLQARVLAIERYLEVQQLLGMWGCSGKLICCTNVPW
NSSWSNKTYNEIWDNMTWMQWDREIGNYTDTIYKLLEVSQFQQEINEKDN
LTLD

SEQ ID NO: 26 provides the amino acid sequence of ConC_Base0_3mut_2G_FP8v2-DS with a signal peptide sequence (e.g., for cellular expression):

MDSKGSSQKGSRLLLLLVVSNLLLPQGVLANLWVTVYYGVPVWKEAKTTL
FCASDAKAYEKEVHNVWATHACVPTDPNPQEMVLENVTENFNMWKNDMVD
QMHEDIISLWDQSLKPCVKLTPLCVTLNCTNVNVTNTNNNNMKEEMKNCS
FNTTTEIRDKKQKEYALFYRLDIVPLNENSSEYRLINCNTSTCTQICPKV
SFDPIPIHYCAPAGYAILKCNNKTFNGTGPCNNVSTVQCTHGIKPVVSTQ
LLLNGSLAEEEIIIRSENLTDNAKTIIVHLNESVEINCTRPNNMTRKSIR
IGPGQTFYALGDIIGDIRQPHCNISEAKWNKTLQRVKKKLKEHFPNKTIK
FAPSSGGDLEITTHSFNCRGEFFYCNTSKLFNSTYNNTTSNSTITLPCRI
KQIINMWQEVGRCMYAPPIAGNITCKSNITGLLLTRDGGNNNNNTETFRP
GGGDMRDNWRSELYKYKVVEIKPLGIAPTKCKRRVVERRRRRRAVGLGAV
FLGFLGAAGSTMGAASNTLTVQARQLLSGIVQQQSNLLRAPEAQQHMLQL
GVWGFKQLQARVLAIERYLEVQQLLGIWGCSGKLICCTAVPWNSSWSNKS
QEDIWDNMTWMQWDREIGNYTDTIYRLLEESQFQQEINEKDLLALD

In some examples, the protomers of the HIV-1 Env ectodomain trimer comprise the sequence of a BG505 chimera including the SOSIP, 6R, T332N, and DS modifications (CH505.DS-SOSIP) that is further modified to include one or more additional amino acid substitutions including the A329P substitution to stabilize a HIV-1 Env ectodomain trimer including the protomers in the prefusion closed conformation. The CH505.DS-SOSIP.6R.664 sequence is set forth as:

```
CH505.DS-SOSIP.6R.664
                                    (SEQ ID NO: 5)
AENLWVTVYYGVPVWKEAKTTLFCASDAKAYEKEVHNVWATHACVPTDPN

PQEMVLKNVTENFNMWKNDMVDQMHEDVISLWDQSLKPCVKLTPLCVTLN

CTNATASNSSIIEGMKNCSFNITTELRDKREKKNALFYKLDIVQLDGNSS

QYRLINCNTSVCTQACPKVSFDPIPIHYCAPAGYAILKCNNKTFTGTGPC

NNVSTVQCTHGIKPVVSTQLLLNGSLAEGEIIIRSENITNNVKTIIVHLN

ESVKIECTRPNNKTRTSIRIGPGQAFYATGQVIGDIREAYCNINESKWNE

TLQRVSKKLKEYFPHKNITFQPSSGGDLEITTHSFNCGGEFFYCNTSSLF

NRTYMANSTDMANSTETNSTRTITIHCRIKQIINMWQEVGRCMYAPPIAG

NITCISNITGLLLTRDGGKNNTETFRPGGGNMKDNWRSELYKYKVVKIEP

LGVAPTRCKRRVVGRRRRRRAVGIGAVFLGFLGAAGSTMGAASMTLTVQA

RNLLSGIVQQQSNLLRAPEAQQHLLKLTVWGIKQLQARVLAVERYLRDQQ

LLGIWGCSGKLICCTNVPWNSSWSNRNLSEIWDNMTWLQWDKEISNYTQI

IYGLLEESQNQQEKNEQDLLALD
```

In some embodiments, the protomers of the HIV-1 Env ectodomain trimer comprise an amino acid sequence set forth as:

```
CH505.DS-SOSIP.3mut.6R.664
                                    (SEQ ID NO: 6)
AENLWVTVYYGVPVWKEAKTTLFCASDAKAYEKEVHNVWATHACVPTDPN

PQEMVLKNVTENFNMWKNDMVDQMHEDVISLWDQSLKPCVKLTPLCVTLN

CTNATASNSSIIEGMKNCSFNITTELRDKREKKNALFYKLDIVQLDGNSS

QYRLINCNTSVCTQACPKVSFDPIPIHYCAPAGYAILKCNNKTFTGTGPC

NNVSTVQCTHGIKPVVSTQLLLNGSLAEGEIIIRSENITNNVKTIIVHLN

ESVKIECTRPNNMTRTSIRIGPGQAFYALGQVIGDIREPYCNINESKWNE

TLQRVSKKLKEYFPHKNITFQPSSGGDLEITTHSFNCGGEFFYCNTSSLF

NRTYMANSTDMANSTETNSTRTITIHCRIKQIINMWQEVGRCMYAPPIAG

NITCISNITGLLLTRDGGKNNTETFRPGGGNMKDNWRSELYKYKVVKIEP

LGVAPTRCKRRVVGRRRRRRAVGIGAVFLGFLGAAGSTMGAASMTLTVQA

RNLLSGIVQQQSNLLRAPEAQQHLLKLTVWGIKQLQARVLAVERYLRDQQ

LLGIWGCSGKLICCTNVPWNSSWSNRNLSEIWDNMTWLQWDKEISNYTQI

IYGLLEESQNQQEKNEQDLLALD
```

In some embodiments, the protomers of the HIV-1 Env ectodomain trimer comprise the sequence of a chimera of gp120 from the more cleavage prone HIV-1 strain 4-2.J41 with gp41 from BG505 and further include the SOSIP substitutions, the GRRRRRR (SEQ ID NO: 27) cleavage site modification, the DS modification (201-433 disulfide) and the 3mut substitutions to stabilize a HIV-1 Env ectodomain trimer including the protomers in the prefusion closed conformation. It is believed that HIV-1 Env trimers formed from such protomers have enhanced gp120/gp41 cleavage, particularly in the context of RNA immunization. For example, the protomers of the HIV-1 Env ectodomain trimer comprise the 4-2.J41-BGSP-jcb_01.3mut sequence set forth as:

```
4-2.J41-BGSP-jcb_01.3mut
                                    (SEQ ID NO: 31)
AVEKLWVTVYYGVPVWKDAKTTLFCASDAKAYDTEVHNVWATHACVPTDP

NPQEMLLDNVTENFNMWKNDMVDQMHEDVISLWDQSLKPCVKLTPLCVTL

ECTDSSNQTHYNESMQEIKNCTFNVTTEIRDRKQRVQALFYKLDIVSLEK

NSSTYRLINCNTSACTQACPKVTFDPIPIHYCTPAGYAILKCNNETFNGT

GPCRNVSTVQCTHGIKPVVSTQLLLNGSLAEKDIMIRSENLTDNAKTIIV

HLNQTVEIVCIRPNNMTRQSIRIGPGQVFYALGDIIGDIRQPYCTINTTA

WNETLQRVSKKLAEHFPNKTIRFAPSSGGDLEITTHSFNCRGEFFYCNTS

GLFNSTYMTNGTFTYKLNDTNITIPCRIKQIINMWQEVGRCMYAPPIAGN

ITCKSNITGMLLVRDGGKNENSTEETFRPGGGNMRDNWRSELYKYKVVEI

KPLGVAPTKCKRRVVGRRRRRRAVGIGAVFLGFLGAAGSTMGAASMTLTV

QARNLLSGIVQQQSNLLRAPEAQQHLLKLTVWGIKQLQARVLAVERYLRD

QQLLGIWGCSGKLICCTNVPWNSSWSNRNLSEIWDNMTWLQWDKEISNYT

QIIYGLLEESQNQQEKNEQDLLALD
```

In some embodiments, the protomers of the HIV-1 Env ectodomain trimer comprise the sequence of BG505 and including the SOSIP substitutions, the 6R cleavage site modification, the DS modification (201-433 disulfide) and the 3mut substitutions to stabilize a HIV-1 Env ectodomain trimer including the protomers in the prefusion closed conformation. It is believed that HIV-1 Env trimers formed from such protomers have enhanced gp120/gp41 cleavage, particularly in the context of RNA immunization. For example, the protomers of the HIV-1 Env ectodomain trimer comprise the BGSP-jcb_04.3mut sequence set forth as:

```
BGSP-jcb_04.3mut
                                    (SEQ ID NO: 32)
AENLWVTVYYGVPVWKDAETTLFCASDAKAYETEKHNVWATHACVPTDPN

PQEIHLENVTEEFNMWKNNMVEQMHTDIISLWDQSLKPCVKLTPLCVTLQ

CTNVTNNITDDMRGELKNCSFNMTTELRDKKQKVYSLFYRLDVVQINENQ

GNRSNNSNKEYRLINCNTSACTQACPKVSFEPIPIHYCAPAGFAILKCKD

KKFNGTGPCPSVSTVQCTHGIKPVVSTQLLLNGSLAEEEVMIRSENITNN

AKNILVQFNTPVQINCTRPNNMTRKSIRIGPGQAFYALGDIIGDIRQPHC

NVSKATWNETLGKVVKQLRKHFGNNTIIRFANSSGGDLEVTTHSFNCGGE

FFYCNTSGLFNSTWISNTSVQGSNSTGSNDSITLPCRIKQIINMWQRIGQ

CMYAPPIQGVIRCVSNITGLILTRDGGSTNSTTETFRPGGGDMRDNWRSE

LYKYKVVKIEPLGVAPTRCKRRVVGNSTHKQLTHHMRRRRRRAVGIGAVF

LGFLGAAGSTMGAASMTLTVQARNLLSGIVQQQSNLLRAPEAQQHLLKLT
```

-continued

VWGIKQLQARVLAVERYLRDQQLLGIWGCSGKLICCTNVPWNSSWSNRNL

SEIWDNMTWLQWDKEISNYTQIIYGLLEESQNQQEKNEQDLLALD

In some embodiments, the protomers of the HIV-1 Env ectodomain trimer comprise the sequence of a chimera of gp120 from the more cleavage prone HIV-1 strain 4-2.J41 with gp41 from BG505 and further include the SOSIP substitutions, the GRRRRRR (SEQ ID NO: 27) cleavage site modification, and the DS modification (201-433 disulfide) to stabilize a HIV-1 Env ectodomain trimer including the protomers in the prefusion closed conformation. It is believed that HIV-1 Env trimers formed from such protomers have enhanced gp120/gp41 cleavage, particularly in the context of RNA immunization. For example, the protomers of the HIV-1 Env ectodomain trimer comprise the 4-2.J41-BGSP-jcb_01.3mut sequence set forth as:

4-2.J41-BGSP-jcb_01

(SEQ ID NO: 33)

AVEKLWVTVYYGVPVWKDAKTTLFCASDAKAYDTEVHNVWATHACVPTD

PNPQEMLLDNVTENFNMWKNDMVDQMHEDVISLWDQSLKPCVKLTPLCV

TLECTDSSNQTHYNESMQEIKNCTFNVTTEIRDRKQRVQALFYKLDIVS

LEKNSSTYRLINCNTSACTQACPKVTFDPIPIHYCTPAGYAILKCNNET

FNGTGPCRNVSTVQCTHGIKPVVSTQLLLNGSLAEKDIMIRSENLTDNA

KTIIVHLNQTVEIVCIRPNNNTRQSIRIGPGQVFYATGDIIGDIRQAYC

TINTTAWNETLQRVSKKLAEHFPNKTIRFAPSSGGDLEITTHSFNCRGE

FFYCNTSGLFNSTYMTNGTFTYKLNDTNITIPCRIKQIINMWQEVGRCM

YAPPIAGNITCKSNITGMLLVRDGGKNENSTEETFRPGGGNMRDNWRSE

LYKYKVVEIKPLGVAPTKCKRRVVGRRRRRRAVGIGAVFLGFLGAAGST

MGAASMTLTVQARNLLSGIVQQQSNLLRAPEAQQHLLKLTVWGIKQLQA

RVLAVERYLRDQQLLGIWGCSGKLICCTNVPWNSSWSNRNLSEIWDNMT

WLQWDKEISNYTQIIYGLLEESQNQQEKNEQDLLALD

In some embodiments, the protomers of the HIV-1 Env ectodomain trimer comprise the sequence of BG505 and including the SOSIP substitutions, the 6R cleavage site modification, and the DS modification (201-433 disulfide) to stabilize a HIV-1 Env ectodomain trimer including the protomers in the prefusion closed conformation. It is believed that HIV-1 Env trimers formed from such protomers have enhanced gp120/gp41 cleavage, particularly in the context of RNA immunization. For example, the protomers of the HIV-1 Env ectodomain trimer comprise the BGSP-jcb_04.3mut sequence set forth as:

BGSP-jcb_04

(SEQ ID NO: 34)

AENLWVTVYYGVPVWKDAETTLFCASDAKAYETEKHNVWATHACVPTDPN

PQEIHLENVTEEFNMWKNNMVEQMHTDIISLWDQSLKPCVKLTPLCVTLQ

CTNVTNNITDDMRGELKNCSFNMTTELRDKKQKVYSLFYRLDVVQINENQ

GNRSNNSNKEYRLINCNTSACTQACPKVSFEPIPIHYCAPAGFAILKCKD

KKFNGTGPCPSVSTVQCTHGIKPVVSTQLLLNGSLAEEEVMIRSENITNN

-continued

AKNILVQFNTPVQINCTRPNNNTRKSIRIGPGQAFYATGDIIGDIRQAHC

NVSKATWNETLGKVVKQLRKHFGNNTIIRFANSSGGDLEVTTHSFNCGGE

FFYCNTSGLFNSTWISNTSVQGSNSTGSNDSITLPCRIKQIINMWQRIGQ

CMYAPPIQGVIRCVSNITGLILTRDGGSTNSTTETFRPGGGDMRDNWRSE

LYKYKVVKIEPLGVAPTRCKRRVVGNSTHKQLTHHMRRRRRRAVGIGAVF

LGFLGAAGSTMGAASMTLTVQARNLLSGIVQQQSNLLRAPEAQQHLLKLT

VWGIKQLQARVLAVERYLRDQQLLGIWGCSGKLICCTNVPWNSSWSNRNL

SEIWDNMTWLQWDKEISNYTQIIYGLLEESQNQQEKNEQDLLALD

SEQ ID NOs: 35-38 provide the amino acid sequences of 4-2.J41-BGSP-jcb_01.3mut, BGSP-jcb_04.3mut, 4-2.J41-BGSP-jcb_01, and BGSP-jcb_04 with a signal peptide sequence (e.g., for cellular expression):

4-2.J41-BGSP-jcb_01.3mut (SEQ ID NO: 35)

MDSKGSSQKGSRLLLLLVVSNLLLPQGVLAAVEKLWVTVYYGVPVWKDAK

TTLFCASDAKAYDTEVHNVWATHACVPTDPNPQEMLLDNVTENFNMWKND

MVDQMHEDVISLWDQSLKPCVKLTPLCVTLECTDSSNQTHYNESMQEIKN

CTFNVTTEIRDRKQRVQALFYKLDIVSLEKNSSTYRLINCNTSACTQACP

KVTFDPIPIHYCTPAGYAILKCNNETFNGTGPCRNVSTVQCTHGIKPVVS

TQLLLNGSLAEKDIMIRSENLTDNAKTIIVHLNQTVEIVCIRPNNMTRQS

IRIGPGQVFYALGDIIGDIRQPYCTINTTAWNETLQRVSKKLAEHFPNKT

IRFAPSSGGDLEITTHSFNCRGEFFYCNTSGLFNSTYMTNGTFTYKLNDT

NITIPCRIKQIINMWQEVGRCMYAPPIAGNITCKSNITGMLLVRDGGKNE

NSTEETFRPGGGNMRDNWRSELYKYKVVEIKPLGVAPTKCKRRVVGRRRR

RRAVGIGAVFLGFLGAAGSTMGAASMTLTVQARNLLSGIVQQQSNLLRAP

EAQQHLLKLTVWGIKQLQARVLAVERYLRDQQLLGIWGCSGKLICCTNVP

WNSSWSNRNLSEIWDNMTWLQWDKEISNYTQIIYGLLEESQNQQEKNEQD

LLALD

BGSP-jcb_04.3mut (SEQ ID NO: 36)

MDSKGSSQKGSRLLLLLVVSNLLLPQGVLAAENLWVTVYYGVPVWKDAET

TLFCASDAKAYETEKHNVWATHACVPTDPNPQEIHLENVTEEFNMWKNNM

VEQMHTDIISLWDQSLKPCVKLTPLCVTLQCTNVTNNITDDMRGELKNCS

FNMTTELRDKKQKVYSLFYRLDVVQINENQGNRSNNSNKEYRLINCNTSA

CTQACPKVSFEPIPIHYCAPAGFAILKCKDKKFNGTGPCPSVSTVQCTHG

IKPVVSTQLLLNGSLAEEEVMIRSENITNNAKNILVQFNTPVQINCTRPN

NMTRKSIRIGPGQAFYALGDIIGDIRQPHCNVSKATWNETLGKVVKQLRK

HFGNNTIIRFANSSGGDLEVTTHSFNCGGEFFYCNTSGLFNSTWISNTSV

QGSNSTGSNDSITLPCRIKQIINMWQRIGQCMYAPPIQGVIRCVSNITGL

ILTRDGGSTNSTTETFRPGGGDMRDNWRSELYKYKVVKIEPLGVAPTRCK

RRVVGNSTHKQLTHHMRRRRRRAVGIGAVFLGFLGAAGSTMGAASMTLTV

QARNLLSGIVQQQSNLLRAPEAQQHLLKLTVWGIKQLQARVLAVERYLRD

-continued

QQLLGIWGCSGKLICCTNVPWNSSWSNRNLSEIWDNMTWLQWDKEISNYT

QIIYGLLEESQNQQEKNEQDLLALD 4-2.J41-BGSP-jcb_01

(SEQ ID NO: 37)

MDSKGSSQKGSRLLLLLVVSNLLLPQGVLAAVEKLWVTVYYGVPVWKDAK

TTLFCASDAKAYDTEVHNVWATHACVPTDPNPQEMLLDNVTENFNMWKND

MVDQMHEDVISLWDQSLKPCVKLTPLCVTLECTDSSNQTHYNESMQEIKN

CTFNVTTEIRDRKQRVQALFYKLDIVSLEKNSSTYRLINCNTSACTQACP

KVTFDPIPIHYCTPAGYAILKCNNETFNGTGPCRNVSTVQCTHGIKPVVS

TQLLLNGSLAEKDIMIRSENLTDNAKTIIVHLNQTVEIVCIRPNNNTRQS

IRIGPGQVFYATGDIIGDIRQAYCTINTTAWNETLQRVSKKLAEHFPNKT

IRFAPSSGGDLEITTHSFNCRGEFFYCNTSGLFNSTYMTNGTFTYKLNDT

NITIPCRIKQIINMWQEVGRCMYAPPIAGNITCKSNITGMLLVRDGGKNE

NSTEETFRPGGGNMRDNWRSELYKYKVVEIKPLGVAPTKCKRRVVGRRRR

RRAVGIGAVFLGFLGAAGSTMGAASMTLTVQARNLLSGIVQQQSNLLRAP

EAQQHLLKLTVWGIKQLQARVLAVERYLRDQQLLGIWGCSGKLICCTNVP

WNSSWSNRNLSEIWDNMTWLQWDKEISNYTQIIYGLLEESQNQQEKNEQD

LLAL

BGSP-jcb_04

(SEQ ID NO: 38)

MDSKGSSQKGSRLLLLLVVSNLLLPQGVLAAENLWVTVYYGVPVWKDAET

TLFCASDAKAYETEKHNVWATHACVPTDPNPQEIHLENVTEEFNMWKNNM

VEQMHTDIISLWDQSLKPCVKLTPLCVTLQCTNVTNNITDDMRGELKNCS

FNMTTELRDKKQKVYSLFYRLDVVQINENQGNRSNNSNKEYRLINCNTSA

CTQACPKVSFEPIPIHYCAPAGFAILKCKDKKFNGTGPCPSVSTVQCTHG

IKPVVSTQLLLNGSLAEEEVMIRSENITNNAKNILVQFNTPVQINCTRPN

NNTRKSIRIGPGQAFYATGDIIGDIRQAHCNVSKATWNETLGKVVKQLRK

HFGNNTIIRFANSSGGDLEVTTHSFNCGGEFFYCNTSGLFNSTWISNTSV

QGSNSTGSNDSITLPCRIKQIINMWQRIGQCMYAPPIQGVIRCVSNITGL

ILTRDGGSTNSTTETFRPGGGDMRDNWRSELYKYKVVKIEPLGVAPTRCK

RRVVGNSTHKQLTHHMRRRRRRAVGIGAVFLGFLGAAGSTMGAASMTLTV

QARNLLSGIVQQQSNLLRAPEAQQHLLKLTVWGIKQLQARVLAVERYLRD

QQLLGIWGCSGKLICCTNVPWNSSWSNRNLSEIWDNMTWLQWDKEISNYT

QIIYGLLEESQNQQEKNEQDLLALD

In several embodiments, the N-terminal residue of the recombinant gp120 protein included in the protomers of the HIV-1 Env ectodomain trimer is one of HIV-1 Env positions 1-35, and the C-terminal residue of the recombinant gp120 protein is one of HIV-1 Env positions 503-511. In some embodiments, the N-terminal residue of the recombinant gp120 protein included in protomers of the HIV-1 Env ectodomain trimer is HIV-1 Env position 31 and the C-terminal residue of the recombinant gp120 protein is HIV-1 Env position 511 or position 507. In some embodiments, the recombinant gp120 protein included in protomers of the HIV-1 Env ectodomain trimer comprise or consist of HIV-1 Env positions 31-507 (HXB2 numbering).

In the protomers of the purified trimer, the recombinant gp120 protein typically does not include a signal peptide (for example, the recombinant gp120 protein typically does not include HIV-1 Env positions 1-30), as the signal peptide is proteolytically cleaved during cellular processing. Additionally, in several embodiments, the gp41 ectodomain included in the protomers of the trimer includes the extracellular portion of gp41 (e.g., positions 512-664). In embodiments including a soluble recombinant HIV-1 Env ectodomain trimer, the gp41 ectodomain is not linked to a transmembrane domain or other membrane anchor. However, in embodiments including a membrane anchored recombinant HIV-1 Env ectodomain trimer, the C-terminus of the gp41 ectodomain can be linked to a transmembrane domain (such as, but not limited to, an HIV-1 Env transmembrane domain).

In some embodiments, the N-terminal residue of the recombinant gp120 protein is HIV-1 Env position 31; the C-terminal residue of the recombinant gp120 protein is HIV-1 Env position 507 or 511; the N-terminal residue of the gp41 ectodomain is HIV-1 Env position 512; and the C-terminal residue of the gp41 ectodomain is HIV-1 Env position 664. In some embodiments, the N-terminal residue of the recombinant gp120 protein is HIV-1 Env position 31; the C-terminal residue of the recombinant gp120 protein is HIV-1 Env position 507; the N-terminal residue of the gp41 ectodomain is HIV-1 Env position 512; and the C-terminal residue of the gp41 ectodomain is HIV-1 Env position 664. In some embodiments, the C-terminal residue of the recombinant HIV-1 Env ectodomain is position 683 (the entire ectodomain, terminating just before the transmembrane domain).

Stabilization of the recombinant HIV-1 Env ectodomain trimer in the prefusion closed conformation reduces transition of the HIV-1 Env ectodomain to the CD4-bound open conformation. Thus, recombinant HIV-1 Env ectodomain trimers that are stabilized in this conformation can be specifically bound by an antibody that is specific for the prefusion closed conformation of HIV-1 Env (e.g., VRC26, PGT151, PGT122, or PGT145), but are not specifically bound by an antibody specific for the CD4-bound open conformation, of HIV-1 Env (e.g., 17b mAb in the presence of sCD4). Methods of determining if a recombinant HIV-1 Env ectodomain trimer includes a CD4-induced epitope are described, for example, in PCT App. No. PCT/US2015/048729. For example, the antibody binding assay can be conducted in the presence of a molar excess of soluble CD4 as described in Sanders et al. (*Plos Pathogens,* 9, e1003618, 2013).

In several embodiments, the recombinant HIV-1 Env ectodomain trimers can be specifically bound by an antibody that specifically binds to the V1V2 domain on a HIV-1 Env trimer, but not an Env monomer. Exemplary antibodies with such antigen binding characteristics include the PGT141, PGT142, PGT143, PGT144, PGT145, and VRC26 antibodies. Additional examples include the PG9, PG16, and CH01-CH04 antibodies. Accordingly, in some embodiments the recombinant HIV-1 Env ectodomain trimer specifically binds to an antibody (such as a PGT141, PGT142, PGT143, PGT144, PGT145, and VRC26 antibody) that specifically binds to the V1V2 domain of a HIV-1 Env in its trimeric, but not monomeric, form with a dissociation constant of less than $10^{-6}$ Molar, such as less than $10^{-7}$ Molar, less than $10^{-8}$ Molar, or less than $10^{-9}$ Molar. Specific binding can be determined by methods known in the art. The determination of specific binding may readily be made by using or adapting routine procedures, such as ELISA, immunocompetition, surface plasmon resonance, or other immunosorbant assays (described in many standard texts, including Greenfield, Antibodies, A Laboratory Manual, 2nd ed. Cold Spring Harbor Laboratory Press, New York (2014).

Several embodiments include a multimer of the recombinant HIV-1 Env ectodomain trimer, for example, a multimer including 2, 3, 4, 5, 6, 7, 8, 9, or 10, or more of the recombinant HIV-1 Env ectodomain trimers or immunogenic fragment thereof.

In view of the conservation and breadth of knowledge of HIV-1 Env sequences, corresponding HIV-1 Env amino acid positions between different HIV-1 Env strains and subtypes can be readily identified. The HXB2 numbering system has been developed to assist comparison between different HIV-1 amino acid and nucleic acid sequences (see, e.g., Korber et al., *Human Retroviruses and AIDS* 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex., which is incorporated by reference herein in its entirety). The numbering of amino acid substitutions disclosed herein is made according to the HXB2 numbering system, unless context indicates otherwise.

It is understood that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering techniques. Examples of such techniques are found in see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013, both of which are incorporated herein by reference in their entirety.

The protomers of the recombinant HIV-1 Env ectodomain trimer can include modifications of the native HIV-1 sequence, such as amino acid substitutions, deletions or insertions, glycosylation and/or covalent linkage to unrelated proteins (e.g., a protein tag), as long as the protomers can form the trimer.

In several embodiments, the recombinant HIV-1 Env ectodomain trimer is soluble in aqueous solution. In some embodiments, the recombinant HIV-1 Env ectodomain trimer dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in phosphate buffered saline (pH 7.4) at room temperature (e.g., 20-22 degrees Celsius) and remains dissolved for at least for at least 12 hours (such as at least 24 hours, at least 48 hours, at least one week, at least two weeks, or more time). In one embodiment, the phosphate buffered saline includes NaC (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM). Determining if a protein remains in solution over time can be accomplished using appropriate techniques. For example, the concentration of the protein dissolved in an aqueous solution can be tested over time using standard methods.

The recombinant HIV-1 Env ectodomain trimer can be derivatized or linked to another molecule (such as another peptide or protein). In general, the recombinant HIV-1 Env ectodomain trimer is derivatized such that the binding to broadly neutralizing antibodies to the trimer is not affected adversely by the derivatization or labeling. For example, the recombinant HIV-1 Env ectodomain trimer can be functionally linked (by chemical coupling, genetic fusion, noncovalent association or otherwise) to one or more other molecular entities, such as an antibody or protein or detection tag.

Single Chain HIV-1 Env Proteins

In some embodiments, the protomers of the HIV-1 Env ectodomain trimer are single chain HIV-1 Env ectodomains, which each include a single polypeptide chain including the gp120 polypeptide and the gp41 ectodomain. Native HIV-1 Env sequences include a furin cleavage site at position 511 (e.g., $REKR_{511}$, SEQ ID NO: 7), which is cleaved by a cellular protease to generate the gp120 and gp41 polypeptides. The single chain proteins do not include the furin cleavage site separating the gp120 and gp41 polypeptides; therefore, when produced in cells, the Env polypeptide is not cleaved into separate gp120 and gp41 polypeptides.

Single chain HIV-1 Env ectodomains can be generated by mutating the furin cleavage site to prevent cleave and formation of separate gp120 and gp41 polypeptide chains. In several embodiments, the gp120 and gp41 polypeptides in the single chain HIV-1 Env ectodomains are joined by a linker, such as a peptide linker. Examples of peptide linkers that can be used include glycine, serine, and glycine-serine linkers. In some embodiments, the peptide liker comprises a 10 amino acid glycine-serine peptide linker, such as a peptide linker comprising the amino acid sequence set forth as SEQ ID NO: 9 (GGSGGGGSGG). In some embodiments, the single chain HIV-1 Env ectodomains can include a heterologous peptide linker between one of HIV-1 Env residues 507 and 512, 503 and 519, 504 and 519, 503 and 522, or 504 and 522. In some embodiments, the HIV-1 Env ectodomain trimer including the recombinant gp120 protein as disclosed herein can include three single chain HIV-1 Env ectodomains each comprising a heterologous peptide linker (such as a 10 amino acid glycine serine linker) between HIV-1 Env residues 507 and 512.

Any of the stabilizing mutations (or combinations thereof) disclosed herein can be included in the single chain HIV-1 Env ectodomain as long as the single chain HIV-1 Env ectodomain retains the desired properties (e.g., the HIV-1 Env prefusion closed conformation).

HIV-1 Env Ectodomain Trimers Linked to a Transmembrane Domain

In some embodiments, the HIV-1 Env ectodomain trimer is membrane anchored, for example, the protomers in the trimer can each be linked to a transmembrane domain. Typically, the transmembrane domain is linked to the C-terminal residue the gp41 ectodomain in the protomers of the HIV-1 Env ectodomain trimer. One or more peptide linkers (such as a gly-ser linker, for example, a 10 amino acid glycine-serine peptide linker, such as a peptide linker comprising the amino acid sequence set forth as SEQ ID NO: 9 (GGSGGGGSGG) can be used to link the transmembrane domain and gp41 ectodomain. In some embodiments a native HIV-1 Env MPER sequence can be used to link the transmembrane domain and the gp41 protein.

Non-limiting examples of transmembrane domains for use with the disclosed embodiments include the BG505 ™ domain (KIFIMIVGGLIGLRIVFAVLSVIHRVR, SEQ ID NO: 10), the Influenza A Hemagglutinin™ domain (ILAIYSTVASSLVLLVSLGAISF, SEQ ID NO: 11), and the Influenza A Neuraminidase™ domain (IITIGSICMVVGIISLILQIGNIISIWVS, SEQ ID NO: 12).

HIV-1 Env Ectodomain Trimers Linked to a Trimerization Domain

In several embodiments, the HIV-1 Env ectodomain trimer can be linked to a trimerization domain, for example, the C-terminus of the gp41 ectodomains included in the protomers of the HIV-1 Env ectodomain trimer can be linked to the trimerization domain. The trimerization domain can promote trimerization of the three protomers of the recombinant HIV-1 Env protein. Non-limiting examples of exogenous multimerization domains that promote stable trimers of soluble recombinant proteins include: the GCN4 leucine zipper (Harbury et al. 1993 *Science* 262:1401-1407), the trimerization motif from the lung surfactant protein (Hoppe et al. 1994 *FEBS Lett* 344:191-195), collagen (McAlinden et al. 2003 *J Biol Chem* 278:42200-42207), and the phage T4 fibritin Foldon (Miroshnikov et al. 1998 *Protein Eng* 11:329-414), any of which can be linked to the recombinant HIV-1 Env ectodomain (e.g., by linkage to the C-terminus of the gp41 polypeptide to promote trimerization of the recombinant HIV-1 protein, as long as the recombinant HIV-1 Env ectodomain retains specific binding activity for a prefusion closed conformation specific antibody, prefusion-specific antibody (e.g., PGT122), and/or includes a HIV-1 Env prefusion closed conformation.

In some examples, the protomers in the recombinant HIV-1 Env ectodomain can be linked to a T4 fibritin Foldon domain, for example, the recombinant HIV-1 Env ectodomain can include a gp41 polypeptide with a Foldon domain linked to its C-terminus. In specific examples, the T4 fibritin Foldon domain can include the amino acid sequence GYIPEAPRDGQAYVRKDGEWVLLSTF (SEQ ID NO: 13), which adopts a β-propeller conformation, and can fold and trimerize in an autonomous way (Tao et al. 1997 *Structure* 5:789-798).

Typically, the heterologous trimerization domain is positioned C-terminal to the gp41 protein. Optionally, the heterologous trimerization is connected to the recombinant HIV-1 Env ectodomain via a linker, such as an amino acid linker. Exemplary linkers include Gly or Gly-Ser linkers, such as SEQ ID NO: 9 (GGSGGGGSGG). Some embodiments include a protease cleavage site for removing the trimerization domain from the HIV-1 polypeptide, such as, but not limited to, a thrombin site between the recombinant HIV-1 Env ectodomain and the trimerization domain.

Protein Nanoparticles

In some embodiments a self-assembled protein nanoparticle is provide that includes multiple copies of a disclosed HIV-1 Env ectodomain trimer (for example, BG505.DS-SOSIP.3mu.6R.664) displayed on the surface of the nanoparticle. Non-limiting examples of such nanoparticles include ferritin, encapsulin, Sulfur Oxygenase Reductase (SOR), and lumazine synthase nanoparticles, which are comprised of an assembly of monomeric subunits including ferritin, encapsulin proteins, SOR proteins, and lumazine synthase proteins, respectively (see, e.g., Lopez-Sagaseta et al., "Self-assembling protein nanoparticles in the design of vaccines," *Comp. and Struct. Biotechnol.*, 14, 58-68, 2016). To construct such protein nanoparticles the protomers of the HIV-1 Env ectodomain trimer can be linked (directly, or indirectly via a peptide linker) to the N- or C-terminus of a subunit of the protein nanoparticle (such as a ferritin protein, an encapsulin protein, a SOR protein, or a lumazine synthase protein) and expressed in cells under appropriate conditions. The resulting fusion proteins self-assemble into a multimeric nanoparticle with trimerized HIV-1 Env protomers and can be purified.

In some embodiments, the protomers of a disclosed HIV-1 Env ectodomain trimer (for example, BG505.DS-SOSIP.3mu.6R.664) can be linked to an *aquifex aeolicus* lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

(SEQ ID NO: 14)
MQIYEGKLTAEGLRFGIVASRFNHALVDRLVEGAIDAIVRHGGREEDITL

VRVPGSWEIPVAAGELARKEDIDAVIAIGVLIRGATPHFDYIASEVSKGL

ADLSLELRKPITFGVITADTLEQAIERAGTKHGNKGWEAALSAIEMANLF

KSLR

In some embodiments, the lumazine synthase subunit can contain one or more mutations to inhibit lumazine synthase activity, such as F22A, H88S, and/or R127A substitutions. Introduction of these mutations blocks lumazine synthase activity without reducing the multimerization of the lumazine synthase 60mer.

In some embodiments, the protomers of a disclosed HIV-1 Env ectodomain trimer (for example, BG505.DS-SOSIP.3mu.6R.664) can be linked to a lumazine synthase subunit including an amino acid sequence at least 80% (such as at least 85%, at least 90%, at least 95%, or at least 97%) identical to amino acid sequence set forth as SEQ ID NO: 14.

Following synthesis, the monomeric subunit proteins self-assemble into the globular lumazine synthase 60mer. In some embodiments, the lumazine synthase-HIV-1 Env protomer fusion can be co-expressed with a corresponding lumazine synthase subunit that lacks the HIV-1 Env protomer. Such co-expression protocols have been shown to increase formation of 60mer particles. Exemplary methods of constructing lumazine synthase protein nanoparticles that display a heterologous antigen are described, for example, in Jardine et al., *Science,* 340(6133): 711-716, 3013, and PCT Pub. WO2016/205704, each of which is incorporated by reference herein).

In some embodiments, protomers of a disclosed HIV-1 Env ectodomain trimer (for example, BG505.DS-SOSIP.3mu.6R.664) can be linked to a ferritin subunit to construct a ferritin nanoparticle. Exemplary description of ferritin nanoparticles that display a heterologous antigen and their use for immunization purposes (e.g., for immunization against influenza antigens) is provided in Kanekiyo et al., *Nature,* 499:102-106, 2013, which is incorporated by reference herein in its entirety. Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such ferritin subunit is represented by:

(SEQ ID NO: 15)
ESQVRQQFSKDIEKLLNEQVNKEMQSSNLYMSMSSWCYTHSLDGAGLFLF

DHAAEEYEHAKKLIIFLNENNVPVQLTSISAPEHKFEGLTQIFQKAYEHE

-continued

```
QHISESINNIVDHAIKSKDHATFNFLQWYVAEQHEEEVLFKDILDKIELI

GNENHGLYLADQYVKGIAKSRKS
```

In some embodiments, protomers of a disclosed HIV-1 Env ectodomain trimer (for example, BG505.DS-SOSIP.3mu.6R.664) can be linked to a ferritin subunit including an amino acid sequence at least 80% (such as at least 85%, at least 90%, at least 95%, or at least 97%) identical to amino acid sequence set forth as SEQ ID NO: 15.

Following synthesis, these monomeric subunit proteins self-assemble into the globular ferritin protein, which has 24 monomeric subunit proteins, and a capsid-like structure having 432 symmetry. Exemplary methods of constructing ferritin nanoparticles that display a heterologous antigen are described, for example, in Zhang, *Int. J. Mol. Sci.,* 12:5406-5421, 2011, which is incorporated herein by reference in its entirety.

In some embodiments, protomers of a disclosed HIV-1 Env ectodomain trimer can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as

```
                                          (SEQ ID NO: 16)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF
```

In some embodiments, protomers of a disclosed HIV-1 Env ectodomain trimer can be linked to an encapsulin subunit including an amino acid sequence at least 80% (such as at least 85%, at least 90%, at least 95%, or at least 97%) identical to amino acid sequence set forth as SEQ ID NO: 16.

Following synthesis, the monomeric subunits self-assemble into the globular encapsulin assembly including 60, or in some cases, 180 monomeric subunits. Methods of constructing encapsulin nanoparticles that display a heterologous antigen are known (see, for example, Sutter et al., *Nature Struct. and Mol. Biol.,* 15:939-947, 2008, which is incorporated by reference herein in its entirety). In specific examples, the encapsulin polypeptide is bacterial encapsulin, such as *Thermotoga* maritime or *Pyrococcus furiosus* or *Rhodococcus erythropolis* or *Myxococcus xanthus* encapsulin.

For production purposes, the protomers of a disclosed HIV-1 Env ectodomain trimer linked to the nanoparticle subunit can include an N-terminal signal peptide that is cleaved during cellular processing. The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography. The monomers of the protein nanoparticle can include various tags and sequences for production and purification of the epitope scaffold protein. Typically such protein tags are linked to the C-terminus of the monomer and are ultimately removed (for example by selective protease cleavage) from the monomer.

Carrier Molecules

In some embodiments, a disclosed HIV-1 Env ectodomain trimer can be linked to a carrier protein by a linker (such as a peptide linker) or can be directly linked to the carrier protein (for example, by conjugation, or synthesis as a fusion protein) too form an immunogenic conjugate.

Suitable linkers are well known to those of skill in the art and include, but are not limited to, straight or branched-chain carbon linkers, heterocyclic carbon linkers or peptide linkers. One skilled in the art will recognize, for an immunogenic conjugate from two or more constituents, each of the constituents will contain the necessary reactive groups. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Hydroxyl, carboxyl, amino and other functionalities, where not present may be introduced by known methods. Likewise, as those skilled in the art will recognize, a wide variety of linking groups may be employed. In some cases, the linking group can be designed to be either hydrophilic or hydrophobic in order to enhance the desired binding characteristics of the HIV-1 Env ectodomain trimer and the carrier. The covalent linkages should be stable relative to the solution conditions under which the conjugate is subjected.

In some embodiments, the linkers may be joined to the constituent amino acids through their side groups (such as through a disulfide linkage to cysteine) or to the alpha carbon amino and carboxyl groups of the terminal amino acids. In some embodiments, the HIV-1 Env ectodomain protomer, the linker, and the carrier can be encoded as a single fusion polypeptide such that the HIV-1 Env ectodomain protomer and the carrier are joined by peptide bonds.

The procedure for attaching a molecule to a polypeptide varies according to the chemical structure of the molecule. Polypeptides typically contain a variety of functional groups; for example, carboxylic acid (COOH), free amine (—$NH_2$) or sulfhydryl (—SH) groups, which are available for reaction with a suitable functional group on a polypeptide. Alternatively, the polypeptide is derivatized to expose or attach additional reactive functional groups. The derivatization may involve attachment of any of a number of linker molecules such as those available from Pierce Chemical Company, Rockford, Ill.

It can be advantageous to produce conjugates in which more than one HIV-1 Env ectodomain trimer is conjugated to a single carrier protein. In several embodiments, the conjugation of multiple HIV-1 Env ectodomain trimers to a single carrier protein is possible because the carrier protein has multiple lysine or cysteine side-chains that can serve as sites of attachment. The amount of HIV-1 Env ectodomain trimer reacted with the amount of carrier may vary depending upon the specific HIV-1 Env ectodomain trimer and the carrier protein. However, the respective amounts should be sufficient to introduce from 1-30 chains of HIV-1 Env ectodomain trimer onto the carrier protein. The resulting number of HIV-1 Env ectodomain trimer linked to a single carrier molecule may vary depending upon the specific HIV-1 Env ectodomain trimer and the carrier protein. In some embodiments, from 1 to 30, such as about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 HIV-1 Env ectodomain trimer can be linked to each carrier protein molecule. "About" in this context refers to plus or minus 5% when measuring an average number of HIV-1 Env ectodomain trimer per carrier molecule in the conjugate. Thus, in some embodiments, the average ratio of HIV-1 Env ectodomain trimer to carrier protein molecules is between about 1:1 and about 30:1, such as about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1, about 21:1, about 22:1, about 23:1, about 24:1, about 25:1, about 26:1, about 27:1, about 28:1, about 29:1, or about 30:1, for example, between about 1:1 and about 15:1, between about 5:1 and about 20:1, or between about 10:1 and about 30:1.

In some embodiments (such as when KLH is used as a carrier), from 1 to 1000, such as about 50, about 100, about 200, about 300, about 400, about 500, about 700, about 1000, about 9, about 10, about 11, about 12, about 13, about 14, about 15, about 16, about 17, about 18, or about 19 HIV-1 Env ectodomain trimer molecules can be linked to each carrier protein. "About" in this context refers to plus or minus 5% when measuring an average number of HIV-1 Env ectodomain trimer molecules per carrier molecule in the conjugate. Thus, in some embodiments, the average ratio of HIV-1 Env ectodomain trimer molecule to carrier protein is between about 1:1 and about 1000:1, such as between about 100:1 and about 500:1, between about 500:1 and about 10000:1, or between about 250:1 and about 750:1.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, recombinantly produced, semi-synthetic or synthetic materials containing one or more amino groups, such as those present in a lysine amino acid residue present in the carrier, to which a reactant moiety can be attached. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000). A carrier can be useful even if the antibody that it elicits is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322); *B. anthracis* LF (for example, as encoded by the complement of bases 149357 to 151786 of GENBANK Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065), such as tetanus toxin heavy chain C fragment; *P. aeruginosa* exotoxin/toxoid (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094) *C. difficile* toxin B or A, or analogs or mimetics of and combinations of two or more thereof. Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin (KLH), horseshoe crab hemocyanin, Concholepas Concholepas Hemocyanin (CCH), Ovalbumin (OVA), edestin, mammalian serum albumins (such as bovine serum albumin), and mammalian immunoglobulins. In some examples, the carrier is bovine serum albumin.

In some embodiments, the carrier is selected from one of: Keyhole Limpet Hemocyanin (KLH), tetanus toxoid, tetanus toxin heavy chain C fragment, diphtheria toxoid, diphtheria toxin variant CRM197, or H influenza protein D (HiD). CRM197 is a genetically detoxified form of diphtheria toxin; a single mutation at position 52, substituting glutamic acid for glycine, causes the ADP-ribosyltransferase activity of the native diphtheria toxin to be lost. For description of protein carriers for vaccines, see Pichichero, Protein carriers of conjugate vaccines: characteristics, development, and clinical trials, *Hum Vaccin Immunother.,* 9: 2505-2523, 2013, which is incorporated by reference herein in its entirety).

Following conjugation of the HIV-1 Env ectodomain trimer to the carrier protein, the conjugate can be purified by a variety of techniques well known to one of skill in the art. One goal of the purification step is to separate the unconjugated HIV-1 Env ectodomain trimer or carrier from the conjugate. The conjugates can be purified away from unconjugated HIV-1 Env ectodomain trimer or carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry, for example.

In several embodiments, the disclosed immunogenic conjugates can be formulated into immunogenic composition (such as vaccines), for example by the addition of a pharmaceutically acceptable carrier and/or adjuvant.

Virus-Like Particles

In some embodiments, a virus-like particle (VLP) is provided that includes a disclosed immunogen. VLPs lack the viral components that are required for virus replication and thus represent a highly attenuated, replication-incompetent form of a virus. However, the VLP can display a polypeptide (e.g., a disclosed recombinant HIV-1 Env ectodomain trimer) that is analogous to that expressed on infectious virus particles and should be equally capable of eliciting an immune response to HIV-1 when administered to a subject. Virus like particles and methods of their production are known and familiar to the person of ordinary skill in the art, and viral proteins from several viruses are known to form VLPs, including human papillomavirus, HIV (Kang et al., *Biol. Chem.* 380: 353-64 (1999)), Semliki-Forest virus (Notka et al., *Biol. Chem.* 380: 341-52 (1999)), human polyomavirus (Goldmann et al., *J. Virol.* 73: 4465-9 (1999)), rotavirus (Jiang et al., *Vaccine* 17: 1005-13 (1999)), parvovirus (Casal, Biotechnology and Applied Biochemistry, Vol 29, Part 2, pp 141-150 (1999)), canine parvovirus (Hurtado et al., *J. Virol.* 70: 5422-9 (1996)), hepatitis E virus (Li et al., *J. Virol.* 71: 7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

III. Polynucleotides and Expression

Polynucleotides encoding a disclosed immunogen are also provided. These polynucleotides include DNA, cDNA and RNA sequences which encode the antigen. One of skill in the art can readily use the genetic code to construct a variety of functionally equivalent nucleic acids, such as nucleic acids which differ in sequence but which encode the same protein sequence, or encode a conjugate or fusion protein including the nucleic acid sequence.

In some embodiments, the protomers of the HIV-1 Env ectodomain trimer are encoded by the nucleic acid sequence set forth as:

```
BG505.DS-SOSIP.3mut DNA
                                        (SEQ ID NO: 17)
GCCGAAAACCTGTGGGTCACCGTGTATTATGGAGTGCCCGTCTGGAAAGA

TGCTGAAACTACCCTGTTCTGTGCCTCTGATGCTAAGGCCTACGAGACCG

AAAAGCACAATGTCTGGGCTACTCATGCATGCGTGCCCACCGACCCAAAC

CCCCAGGAGATCCACCTGGAAAATGTGACCGAGGAATTCAACATGTGGAA

AAACAATATGGTGGAGCAGATGCATACAGACATCATTAGCCTGTGGGATC

AGTCCCTGAAGCCCTGCGTCAAACTGACTCCTCTGTGCGTGACCCTGCAG

TGTACCAATGTCACAAACAATATCACCGACGATATGAGGGGCGAGCTGAA

GAATTGTAGCTTCAACATGACCACAGAACTGAGAGACAAGAAACAGAAAG

TGTACTCCCTGTTTTATAGGCTGGATGTGGTCCAGATCAATGAGAACCAG

GGGAATCGGAGCAACAATTCCAACAAGGAATACAGACTGATCAATTGCAA

CACTTCCGCCTGTACCCAGGCTTGTCCTAAAGTGTCTTTTGAGCCTATCC

CAATTCATTATTGCGCCCCAGCTGGCTTCGCCATCCTGAAGTGTAAAGAT

AAGAAGTTCAACGGAACTGGCCCCTGCCCTTCCGTGTCTACAGTCCAGTG

TACTCACGGGATTAAGCCTGTGGTCTCTACACAGCTGCTGCTGAATGGAA

GTCTGGCTGAGGAAGAAGTGATGATCCGGAGCGAGAACATTACCAACAAT

GCCAAGAATATCCTGGTCCAGTTCAACACACCAGTGCAGATTAATTGCAC

AAGACCCAACAATATGACTCGAAAATCTATCCGGATTGGGCCAGGACAGG

CCTTTTACGCTCTGGGGGACATCATTGGAGATATCAGACAGCCTCACTGT

AATGTGAGTAAGGCAACCTGGAACGAGACACTGGGCAAGGTGGTCAAACA

GCTGAGGAAACATTTCGGGAATAACACCATCATTCGCTTTGCCAATAGCT

CCGGAGGGGACCTGGAGGTCACTACCCACTCCTTCAACTGCGGAGGCGAA

TTCTTTTACTGTAACACATCTGGCCTGTTTAATAGTACATGGATCTCTAA

CACTAGTGTGCAGGGCAGTAATTCAACTGGGTCAAACGATAGCATCACCC
```

-continued

```
TGCCATGCCGAATTAAGCAGATCATTAATATGTGGCAGCGGATCGGCCAG

TGCATGTATGCCCCCCCTATCCAGGGGGTCATTCGCTGCGTGAGCAATAT

CACCGGACTGATTCTGACACGAGACGGGGGCAGCACCAACTCTACAACTG

AAACATTCCGGCCCGGCGGGGGAGACATGAGAGATAACTGGAGGTCCGAG

CTGTACAAGTATAAAGTGGTCAAGATCGAACCTCTGGGAGTGGCACCAAC

CAGATGCAAGCGAAGAGTGGTCGGACGAAGGAGGAGGAGGCGAGCAGTCG

GAATTGGGGCCGTGTTCCTGGGATTTCTGGGCGCCGCTGGGAGTACAATG

GGAGCAGCCTCAATGACTCTGACCGTGCAGGCCAGGAATCTGCTGAGCGG

CATCGTCCAGCAGCAGTCCAACCTGCTGCGCGCTCCTGAAGCACAGCAGC

ACCTGCTGAAGCTGACCGTGTGGGGCATCAAACAGCTGCAGGCTAGGGTG

CTGGCAGTCGAGCGGTACCTGAGAGACCAGCAGCTGCTGGGAATCTGGGG

CTGCTCTGGGAAGCTGATTTGTTGCACAAATGTGCCTTGGAACTCTAGTT

GGTCAAATCGCAACCTGAGCGAGATCTGGGACAATATGACTTGGCTGCAG

TGGGATAAAGAAATTAGTAACTACACCCAGATCATCTACGGCCTGCTGGA

AGAGTCACAGAATCAGCAGGAGAAGAACGAACAGGACCTGCTGGCTCTGG

ATTG
```

SEQ ID NO: 18 provides a nucleic acid sequence encoding a protomer of BG505.DS-SOSIP.3mut with a signal peptide sequence:

```
TCTAGAGCCACCATGCCTATGGGGAGCCTGCAGCCTCTGGCAACCCTGTA

TCTGCTGGGAATGCTGGTCGCAAGTGTCCTGGCCGCCGAAAACCTGTGGG

TCACCGTGTATTATGGAGTGCCCGTCTGGAAAGATGCTGAAACTACCCTG

TTCTGTGCCTCTGATGCTAAGGCCTACGAGACCGAAAAGCACAATGTCTG

GGCTACTCATGCATGCGTGCCCACCGACCCAAACCCCCAGGAGATCCACC

TGGAAAATGTGACCGAGGAATTCAACATGTGGAAAAACAATATGGTGGAG

CAGATGCATACAGACATCATTAGCCTGTGGGATCAGTCCCTGAAGCCCTG

CGTCAAACTGACTCCTCTGTGCGTGACCCTGCAGTGTACCAATGTCACAA

ACAATATCACCGACGATATGAGGGGCGAGCTGAAGAATTGTAGCTTCAAC

ATGACCACAGAACTGAGAGACAAGAAACAGAAAGTGTACTCCCTGTTTTA

TAGGCTGGATGTGGTCCAGATCAATGAGAACCAGGGGAATCGGAGCAACA

ATTCCAACAAGGAATACAGACTGATCAATTGCAACACTTCCGCCTGTACC

CAGGCTTGTCCTAAAGTGTCTTTTGAGCCTATCCCAATTCATTATTGCGC

CCCAGCTGGCTTCGCCATCCTGAAGTGTAAAGATAAGAAGTTCAACGGAA

CTGGCCCCTGCCCTTCCGTGTCTACAGTCCAGTGTACTCACGGGATTAAG

CCTGTGGTCTCTACACAGCTGCTGCTGAATGGAAGTCTGGCTGAGGAAGA

AGTGATGATCCGGAGCGAGAACATTACCAACAATGCCAAGAATATCCTGG

TCCAGTTCAACACACCAGTGCAGATTAATTGCACAAGACCCAACAATATG

ACTCGAAAATCTATCCGGATTGGGCCAGGACAGGCCTTTTACGCTCTGGG

GGACATCATTGGAGATATCAGACAGCCTCACTGTAATGTGAGTAAGGCAA

CCTGGAACGAGACACTGGGCAAGGTGGTCAAACAGCTGAGGAAACATTTC
```

-continued

```
GGGAATAACACCATCATTCGCTTTGCCAATAGCTCCGGAGGGGACCTGGA
GGTCACTACCCACTCCTTCAACTGCGGAGGCGAATTCTTTTACTGTAACA
CATCTGGCCTGTTTAATAGTACATGGATCTCTAACACTAGTGTGCAGGGC
AGTAATTCAACTGGGTCAAACGATAGCATCACCCTGCCATGCCGAATTAA
GCAGATCATTAATATGTGGCAGCGGATCGGCCAGTGCATGTATGCCCCCC
CTATCCAGGGGGTCATTCGCTGCGTGAGCAATATCACCGGACTGATTCTG
ACACGAGACGGGGGCAGCACCAACTCTACAACTGAAACATTCCGGCCCGG
CGGGGGAGACATGAGAGATAACTGGAGGTCCGAGCTGTACAAGTATAAAG
TGGTCAAGATCGAACCTCTGGGAGTGGCACCAACCAGATGCAAGCGAAGA
GTGGTCGGACGAAGGAGGAGGAGGCGAGCAGTCGGAATTGGGGCCGTGTT
CCTGGGATTTCTGGGCGCCGCTGGGAGTACAATGGGAGCAGCCTCAATGA
CTCTGACCGTGCAGGCCAGGAATCTGCTGAGCGGCATCGTCCAGCAGCAG
TCCAACCTGCTGCGCGCTCCTGAAGCACAGCAGCACCTGCTGAAGCTGAC
CGTGTGGGGCATCAAACAGCTGCAGGCTAGGGTGCTGGCAGTCGAGCGGT
ACCTGAGAGACCAGCAGCTGCTGGGAATCTGGGGCTGCTCTGGGAAGCTG
ATTTGTTGCACAAATGTGCCTTGGAACTCTAGTTGGTCAAATCGCAACCT
GAGCGAGATCTGGGACAATATGACTTGGCTGCAGTGGGATAAAGAAATTA
GTAACTACACCCAGATCATCTACGGCCTGCTGGAAGAGTCACAGAATCAG
CAGGAGAAGAACGAACAGGACCTGCTGGCTCTGGATTG
```

In several embodiments, the nucleic acid molecule encodes a precursor of a protomer of a disclosed HIV-1 Env trimer, that, when expressed in cells under appropriate conditions, forms HIV-1 Env trimers and is processed into the mature form of the HIV-1 Env protein.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4th ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie A G, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed immunogen can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed immunogen can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the disclosed immunogen can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4th Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol*, 79, 8828-8834, 2005, which is incorporated by reference herein).

Modifications can be made to a nucleic acid encoding a disclosed immunogen without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

IV. Viral Vectors

A nucleic acid molecule encoding a disclosed immunogen can be included in a viral vector, for example, for expression of the immunogen in a host cell, or for immunization of a subject. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed antigens, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, Curr. Top. *Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3291-3297), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In several embodiments, the viral vector can include an adenoviral vector that expresses a disclosed immunogen. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/02231 1.

V. Immunogenic Compositions

Immunogenic compositions comprising a disclosed immunogen and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. Methods for preparing administrable compositions are described in more detail in such publications as *Remingtons Pharmaceutical Sciences*, $19^{th}$ Ed., Mack Publishing Company, Easton, Pa., 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The pharmaceutical composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the composition can be provided as a sterile composition. The pharmaceutical composition typically contains an effective amount of a disclosed immunogen and can be prepared by conventional techniques. Typically, the amount of immunogen in each dose of the immunogenic composition is selected as an amount which elicits an immune response without significant, adverse side effects. In some embodiments, the composition can be provided in unit dosage form for use to elicit an immune response in a subject, for example, to prevent HIV-1 infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VI. Methods of Inducing an Immune Response

The disclosed immunogens (e.g., a recombinant HIV-1 Env ectodomain trimer comprising the DS-SOSIP.3mut substitutions), polynucleotides and vectors encoding the disclosed immunogens, and compositions including same, can be used in methods of inducing an immune response to HIV-1 to prevent, inhibit, and/or treat an HIV-1 infection.

When inhibiting, treating, or preventing HIV-1 infection, the methods can be used either to avoid infection in an HIV-1 seronegative subject (e.g., by inducing an immune response that protects against HIV-1 infection), or to treat existing infection in an HIV-1 seropositive subject. The HIV-1 seropositive subject may or may not carry a diagnosis of AIDS. Hence in some embodiments the methods involve selecting a subject at risk for contracting HIV-1 infection, or a subject at risk of developing AIDS (such as a subject with HIV-1 infection), and administering a disclosed immunogen to the subject to elicit an immune response to HIV-1 in the subject.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize HIV-1 infection. These and other routine methods allow the clinician to select patients in need of therapy using the methods and pharmaceutical compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The disclosed immunogens can be used in coordinate (or prime-boost) immunization protocols or combinatorial formulations. In certain embodiments, novel combinatorial immunogenic compositions and coordinate immunization protocols employ separate immunogens or formulations, each directed toward eliciting an anti-HIV-1 immune response, such as an immune response to HIV-1 Env protein. Separate immunogenic compositions that elicit the anti-HIV-1 immune response can be combined in a polyvalent immunogenic composition administered to a subject in a single immunization step, or they can be administered separately (in monovalent immunogenic compositions) in a coordinate immunization protocol.

In one embodiment, a suitable immunization regimen includes at least two separate inoculations with one or more immunogenic compositions including a disclosed immunogen, with a second inoculation being administered more than about two, about three to eight, or about four, weeks following the first inoculation. A third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of HIV-1 infection or progression to AIDS, improvement in disease state (e.g., reduction in viral load), or reduction in transmission frequency to an uninfected partner. If such monitoring indicates that vaccination is sub-optimal, the subject can be boosted with an additional dose of immunogenic composition, and the vaccination parameters can be modified in a fashion expected to potentiate the immune response. Thus, for example, a dose of a disclosed immunogen can be increased or the route of administration can be changed.

It is contemplated that there can be several boosts, and that each boost can be a different immunogen. It is also contemplated in some examples that the boost may be the same immunogen as another boost, or the prime.

The prime and the boost can be administered as a single dose or multiple doses, for example, two doses, three doses, four doses, five doses, six doses or more can be administered to a subject over days, weeks or months. Multiple boosts can also be given, such one to five, or more. Different dosages can be used in a series of sequential inoculations. For example, a relatively large dose in a primary inoculation and then a boost with relatively smaller doses. The immune response against the selected antigenic surface can be elicited by one or more inoculations of a subject.

In several embodiments, a disclosed immunogen can be administered to the subject simultaneously with the administration of an adjuvant. In other embodiments, the immunogen can be administered to the subject after the administration of an adjuvant and within a sufficient amount of time to elicit the immune response.

Determination of effective dosages in this context is typically based on animal model studies followed up by human clinical trials and is guided by administration protocols that significantly reduce the occurrence or severity of targeted disease symptoms or conditions in the subject, or that elicit a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer an effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Dosage can be varied by the attending clinician to maintain a desired concentration at a target site (for example, systemic circulation). Higher or lower concentrations can be selected based on the mode of delivery, for example, trans-epidermal, rectal, oral, pulmonary, or intranasal delivery versus intravenous or subcutaneous delivery. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

A non-limiting range for an effective amount of the disclosed immunogen within the methods and immunogenic compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example, 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. In some embodiments, the dosage includes a set amount of a disclosed immunogen such as from about 1-300 μg, for example, a dosage of about 1, 2, 3, 4, 5, 6, 7, 8, 9, 10, 15, 20, 30, 40, 50, 60, 70, 80, 90, 100, 150, 200, 250, or about 300 μg.

The dosage and number of doses will depend on the setting, for example, in an adult or anyone primed by prior HIV-1 infection or immunization, a single dose may be a sufficient booster. In naïve subjects, in some examples, at least two doses would be given, for example, at least three doses. In some embodiments, an annual boost is given, for example, along with an annual influenza vaccination.

HIV-1 infection does not need to be completely inhibited for the methods to be effective. For example, elicitation of an immune response to HIV-1 with one or more of the disclosed immunogens can reduce or inhibit HIV-1 infection by a desired amount, for example, by at least 10%, at least 20%, at least 50%, at least 60%, at least 70%, at least 80%, at least 90%, at least 95%, at least 98%, or even at least 100% (elimination or prevention of detectable HIV-1 infected cells), as compared to HIV-1 infection in the absence of the therapeutic agent. In additional examples, HIV-1 replication can be reduced or inhibited by the disclosed methods. HIV-1 replication does not need to be completely eliminated for the method to be effective. For example, the immune response elicited using one or more of the disclosed immunogens can reduce HIV-1 replication by a desired amount, for example, by at least 10%, at least 20%, at least 50%, at least 60%, at least 70%, at least 80%, at least 90%, at least 95%, at least 98%, or even at least 100% (elimination or prevention of detectable HIV-1 replication), as compared to HIV-1 replication in the absence of the immune response.

To successfully reproduce itself, HIV-1 must convert its RNA genome to DNA, which is then imported into the host cell's nucleus and inserted into the host genome through the action of HIV-1 integrase. Because HIV-1's primary cellular target, CD4+ T-Cells, can function as the memory cells of the immune system, integrated HIV-1 can remain dormant for the duration of these cells' lifetime. Memory T-Cells may survive for many years and possibly for decades. This latent HIV-1 reservoir can be measured by co-culturing CD4+ T-Cells from infected patients with CD4+ T-Cells from uninfected donors and measuring HIV-1 protein or RNA (See, e.g., Archin et al., AIDS, 22:1131-1135, 2008). In some embodiments, the provided methods of treating or inhibiting HIV-1 infection include reduction or elimination of the latent reservoir of HIV-1 infected cells in a subject. For example, a reduction of at least 10%, at least 20%, at least 50%, at least 60%, at least 70%, at least 80%, at least 90%, at least 95%, at least 98%, or even at least 100% (elimination of detectable HIV-1) of the latent reservoir of HIV-1 infected cells in a subject, as compared to the latent reservoir of HIV-1 infected cells in a subject in the absence of the treatment with one or more of the provided immunogens.

Following immunization of a subject, serum can be collected from the subject at appropriate time points, frozen, and stored for neutralization testing. Methods to assay for neutralization activity, and include, but are not limited to, plaque reduction neutralization (PRNT) assays, microneutralization assays, flow cytometry based assays, single-cycle infection assays (e.g., as described in Martin et al. (2003) *Nature Biotechnology* 21:71-76), and pseudovirus neutralization assays (e.g., as described in Georgiev et al. (*Science,* 340, 751-756, 2013), Seaman et al. (*J. Virol.,* 84, 1439-1452, 2005), and Mascola et al. (*J. Virol.,* 79, 10103-10107, 2005), each of which is incorporated by reference herein in its entirety. In some embodiments, the serum neutralization activity can be assayed using a panel of HIV-1 pseudoviruses as described in Georgiev et al., *Science,* 340, 751-756, 2013 or Seaman et al. *J. Virol.,* 84, 1439-1452, 2005. Briefly, pseudovirus stocks are prepared by co-transfection of 293T cells with an HIV-1 Env-deficient backbone and an expression plasmid encoding the Env gene of interest. The serum to be assayed is diluted in Dulbecco's modified Eagle medium-10% FCS (Gibco) and mixed with pseudovirus. After 30 min, 10,000 TZM-bl cells are added, and the plates are incubated for 48 hours. Assays are developed with a luciferase assay system (Promega, Madison, Wis.), and the relative light units (RLU) are read on a luminometer (Perkin-Elmer, Waltham, Mass.). To account for background, a cutoff of $ID_{50}\geq40$ can be used as a criterion for the presence of serum neutralization activity against a given pseudovirus.

In some embodiments, administration of an effective amount of one or more of the disclosed immunogens to a subject (e.g., by a prime-boost administration of a DNA vector encoding a disclosed immunogen (prime) followed by a protein nanoparticle including a disclosed immunogen (boost)) elicits a neutralizing immune response in the subject, wherein serum from the subject neutralizes, with an $ID_{50}\geq40$, at least 10% (such as at least 15%, at least 20%, at least 30%, at least 40%, at least 50%, or at least 70%) of pseudoviruses is a panel of pseudoviruses including the HIV-1 Env proteins listed in Table S5 or Table S6 of Georgiev et al. (*Science,* 340, 751-756, 2013), or Table 1 of Seaman et al. (*J. Virol.,* 84, 1439-1452, 2005).

One approach to administration of nucleic acids is direct immunization with plasmid DNA, such as with a mammalian expression plasmid. Immunization by nucleic acid constructs is taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil ATM (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 g encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to elicit an immune response to HIV-1 gp120. In some embodiments, the nucleic acid molecule can be included on a plasmid vector for DNA immunization, such as the pVRC8400 vector (described in Barouch et al., *J. Virol,* 79, 8828-8834, 2005, which is incorporated by reference herein).

In another approach to using nucleic acids for immunization, a disclosed immunogen (such as a protomer of a HIV-1 Env ectodomain trimer) can be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a disclosed immunogen (such as a protomer of a HIV-1 Env ectodomain trimer) is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

EXAMPLES

The following examples are provided to illustrate particular features of certain embodiments, but the scope of the claims should not be limited to those features exemplified.

Example 1

Recombinant HIV-1 Env Ectodomain Trimers Stabilized in a Prefusion Closed Confirmation The HIV-1 Env trimer is a target for vaccine design as well as a conformational machine that facilitates virus entry by transitioning between prefusion-closed, CD4-bound, and co-receptor-bound conformations before rearranging into a postfusion state. Vaccine designers have sought to restrict the conformation of the HIV-1-Env trimer to its prefusion-closed state, as this state is recognized by most broadly neutralizing—but not by non-neutralizing-antibodies. A previously identified disulfide bond, I201C-A433C (DS) contributes to the stabilization of Env in the vaccine-desired prefusion-closed state. When the DS mutation was placed into the context of BG505 SOSIP.6R.664, a previously identified soluble Env-trimer mimic, the engineered "DS-SOSIP" (SEQ ID NO: 2) trimer showed reduced conformational triggering by CD4.

This example describes further stabilization of BG505.DS-SOSIP.6R.664 in the prevision closed conformation through a combination of structure-based design and antigenic assessment. From more than 100 designs, a new combination of stabilizing mutations was identified and introduced into BG505.DS-SOSIP.6R.664 to generate a construct termed BG505.DS-SOSIP.3mut.6R.664 or ("DS-SOSIP.3mut"). DS-SOSIP.3mut contains three additional mutations at the interface of potentially mobile domains of the prefusion-closed structure relative to DS-SOSIP: a methionine substitution at HIV-1 Env position 302 (N302M), a leucine substitution at HIV-1 Env position 320 (T320L), and a proline substitution at HIV-1 Env positon 329 (A329P). Notably, DS-SOSIP.3mut showed reduced recognition of CD4 and increased thermostability relative to DS-SOSIP, as well as another modified HIV-1 Env trimer with a different set of stabilizing mutations termed BG505.DS-SOSIP.4mut.6R.664 or "DS-SOSIP.4mut." DS-SOSIP.4mut contains L154M, N300M, N302M, and T320L relative to DS-SOSIP, and demonstrated superior antigenicity with increased binding to broadly neutralizing antibodies and decreased binding to antibodies that target CD4-induced epitopes relative to other prefusion stabilized HIV-1 Env designs. The improved antigenicity and thermostability of DS-SOSIP.3mut suggests utility as an immunogen and a serologic probe. Moreover, the specific 3mut alterations identified can be transferred to other HIV-1 Env trimers of interest to improve their properties.

Design and antigenic assessment. Mutations were introduced into DS-SOSIP that were predicted to form hydrophobic patches at the interfaces of the mobile apex region based on computational structural modeling, or to reduce conformational flexibility by introducing a proline residue. The antigenicity of several designs was assessed after transiently expressing each construct with 293T cells in a 96-well plate format and assessing the antigenicity of supernatants by ELISA. The sum of broadly neutralizing mAbs PGT145 and CAP256-VRC26.09 reactivity divided by the sum of weakly neutralizing antibody reactivity (for the V3-directed antibodies 447-52D and 3074 (Killikelly et al. 2013. *Biochemistry* 52:6249-6257; Gorny et al. 2006. *J Virol* 80:6865-6872) in the presence of CD4) was used to rank each design. Two designs, DS-SOSIP.4mut and DS-SOSIP.3mut, were further characterized. The mutations in the DS-SOSIP.4mut design (L154M/N300M/N302M/T320L) were predicted to form a hydrophobic patch at the interface between the $1^{st}$ and $2^{nd}$ variable (V1V2) regions and the $3^{rd}$ variable (V3) loop region interface. Additionally, the CD4-bound structure of Env was examined for regions that differed in conformation from the prefusion-closed conformation, and especially for residues where a proline substitution would be compatible with the prefusion closed conformation, and incompatible with the CD4-bound conformation. The strict +/− Phi angle required for prolines places strong constraints on conformation. One such residue was located at position 329, where substitution to proline was incompatible with the CD4-bound conformation, but compatible with the prefusion closed conformation. The A329P substitution is thus designed to make transitions to the CD4-bound conformation less accessible, and thereby stabilize the alternative prefusion closed conformation.

Figure 2A:
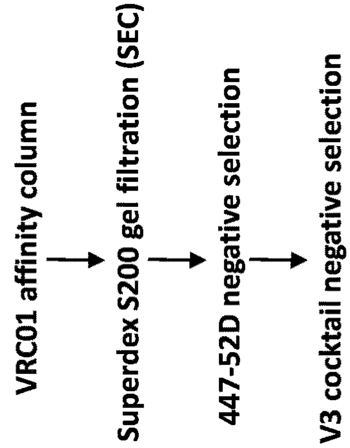
FIGS. 2A-2D. Properties of stabilized HIV-1 Env trimers.
Figure 2B:
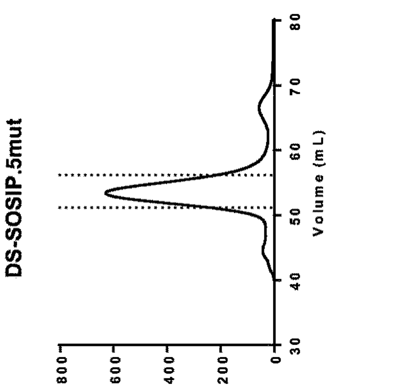
Figure 2B:
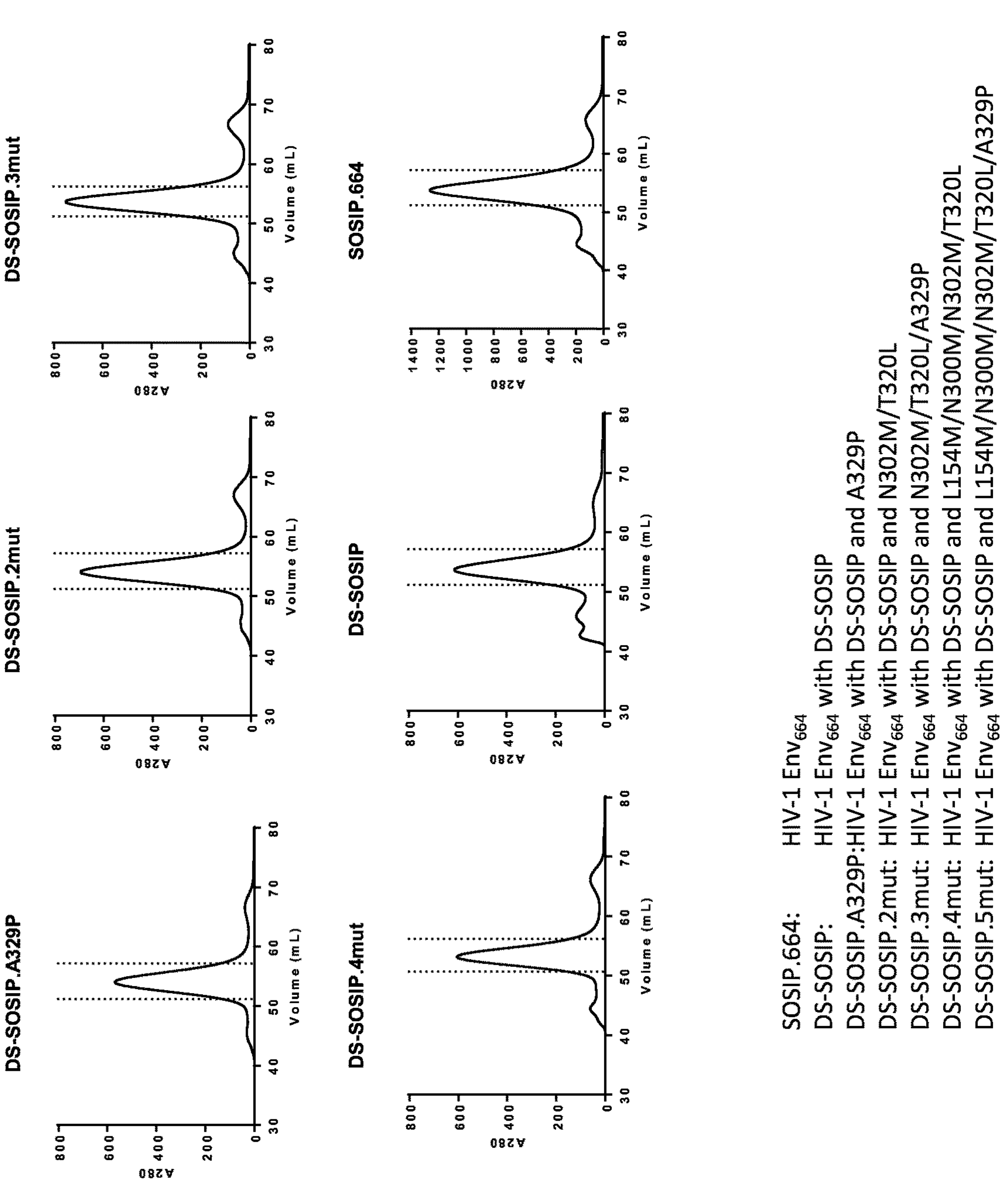
Figures 2C, 2D:
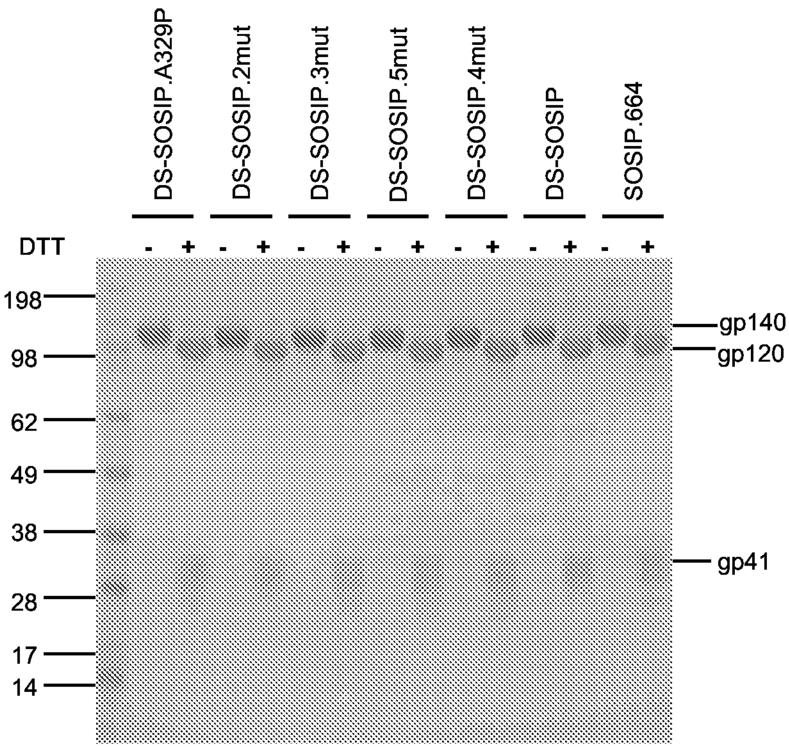

Expression and purification. DS-SOSIP.A329P, DS-SOSIP.2mut, DS-SOSIP.3mut, DS-SOSIP.4mut, DS-SOSIP.5mut, DS-SOSIP, and SOSIP.664 were expressed and purified. The purification protocol involved sequential steps of a VRC01 affinity column, gel filtration chromatography (SEC), a 447-52D mAb negative selection affinity column, and a V3 mAb cocktail negative selection affinity column (FIG. 2A). SEC profiles of these variants were similar to that of DS-SOSIP (FIG. 2B), and showed comparable expression yields to that of DS-SOSIP (FIG. 2D). SDS-PAGE analysis indicated each of these constructs to be fully cleaved and to run as separate gp120 and gp41 subunits under reducing conditions (FIG. 2C).

Figure 3A:
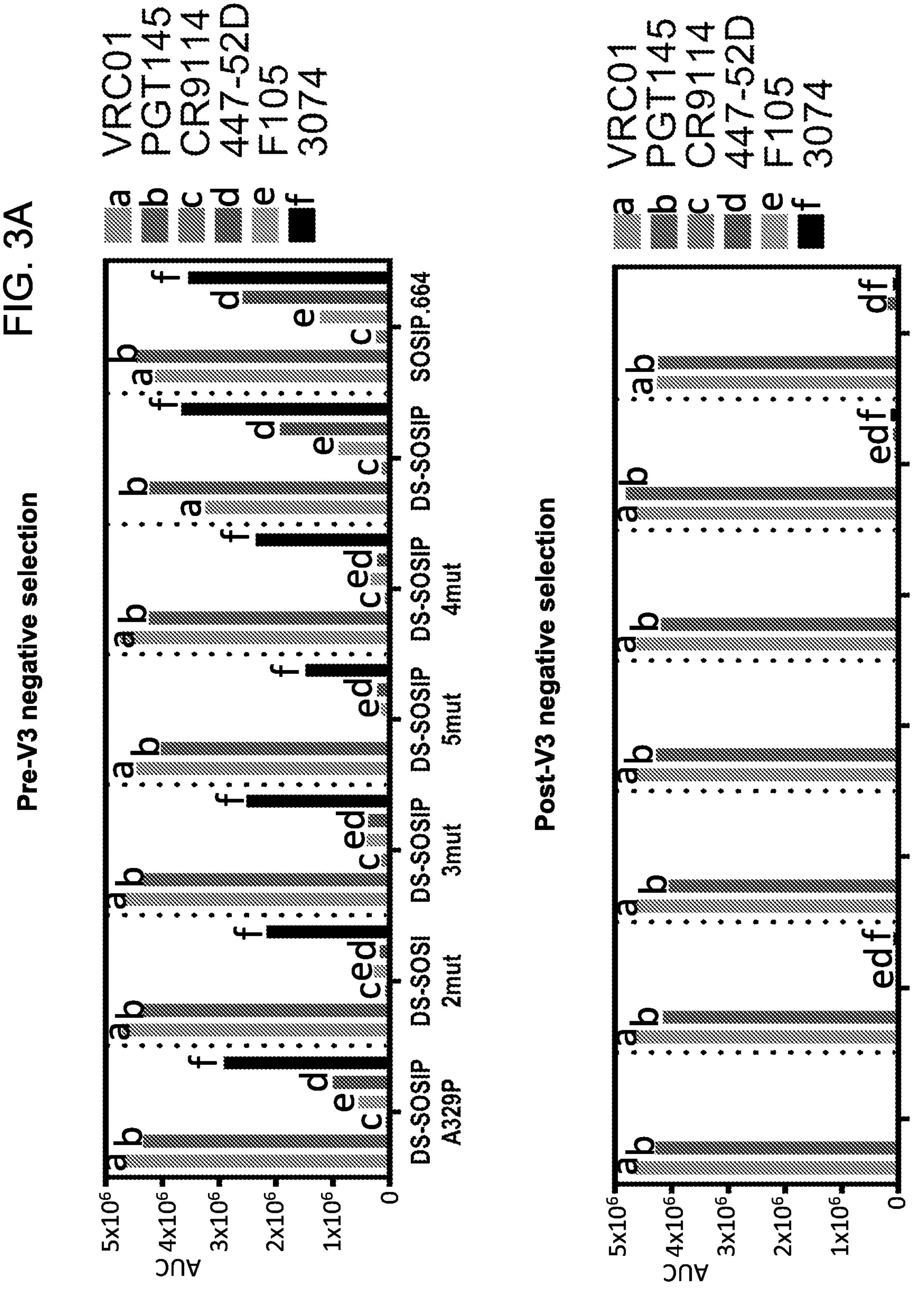
FIGS. 3A and 3B. Antigenicity of stabilized Env trimer as determined by Meso Scale Discovery (MSD).
Figure 3B:
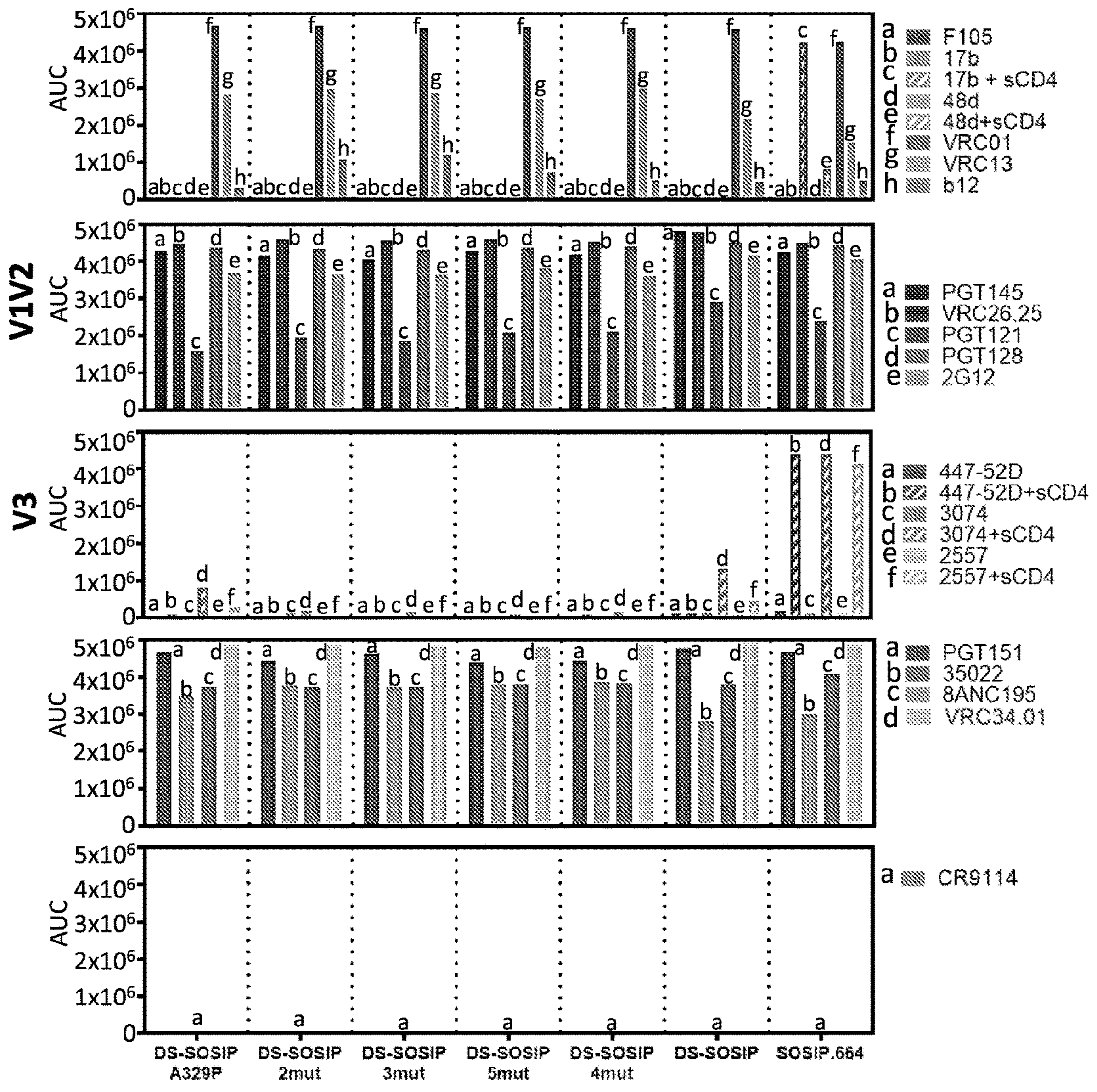

DS-SOSIP.3mut shows improved antigenicity for the prefusion closed state. To define antigenicity, binding of DS-SOSIP.A329P, DS-SOSIP.2mut, DS-SOSIP.3mut, DS-SOSIP.4mut, DS-SOSIP.5mut, DS-SOSIP, and SOSIP.664 to a panel of multiple HIV-1 antibodies was assessed by multi-array Meso Scale Discovery (MSD, FIG. 3). Pre- and Post V3 negative selection, antigenicity was assessed with broadly neutralizing antibodies (VRC01, PGT145), weakly or non-neutralizing antibodies (F105, 447-52D, 3074), and a control antibody (CR9114, a flu antibody with no recognition of HIV-1 Env) (FIG. 3A). Prior to negative selection with V3-directed antibodies, several of these constructs were observed to exhibit lower binding affinity toward V3-directed antibodies 447-52D and 3074 than DS-SOSIP, with DS-SOSIP.3mut providing the lowest binding affinity. After negative selection with V3-directed antibodies, several constructs displayed even lower V3-directed antibody binding, again with SOSIP.3mut providing the lowest binding affinity. Additionally, antigenicity of stabilized DS-SOSIP variants after V3-negative selection was assessed on a panel of CD4-induced antibodies (17b and 48d, with and without soluble CD4), CD4-binding site antibodies (VRC01, VRC13 and b12), V2-apex-directed antibodies (PGT145, CAP256-VRC26.25), glycan-V3 antibodies (PGT121, PGT128 and 2G12), weakly neutralizing V3-directed antibodies (447-52D, 3074 and 2557, with and without soluble CD4), gp41-gp120 interface antibodies (PGT151, 35022 and 8ANC195) and fusion peptide antibody (VRC34.01) FIG. 3B).

Figure 4:
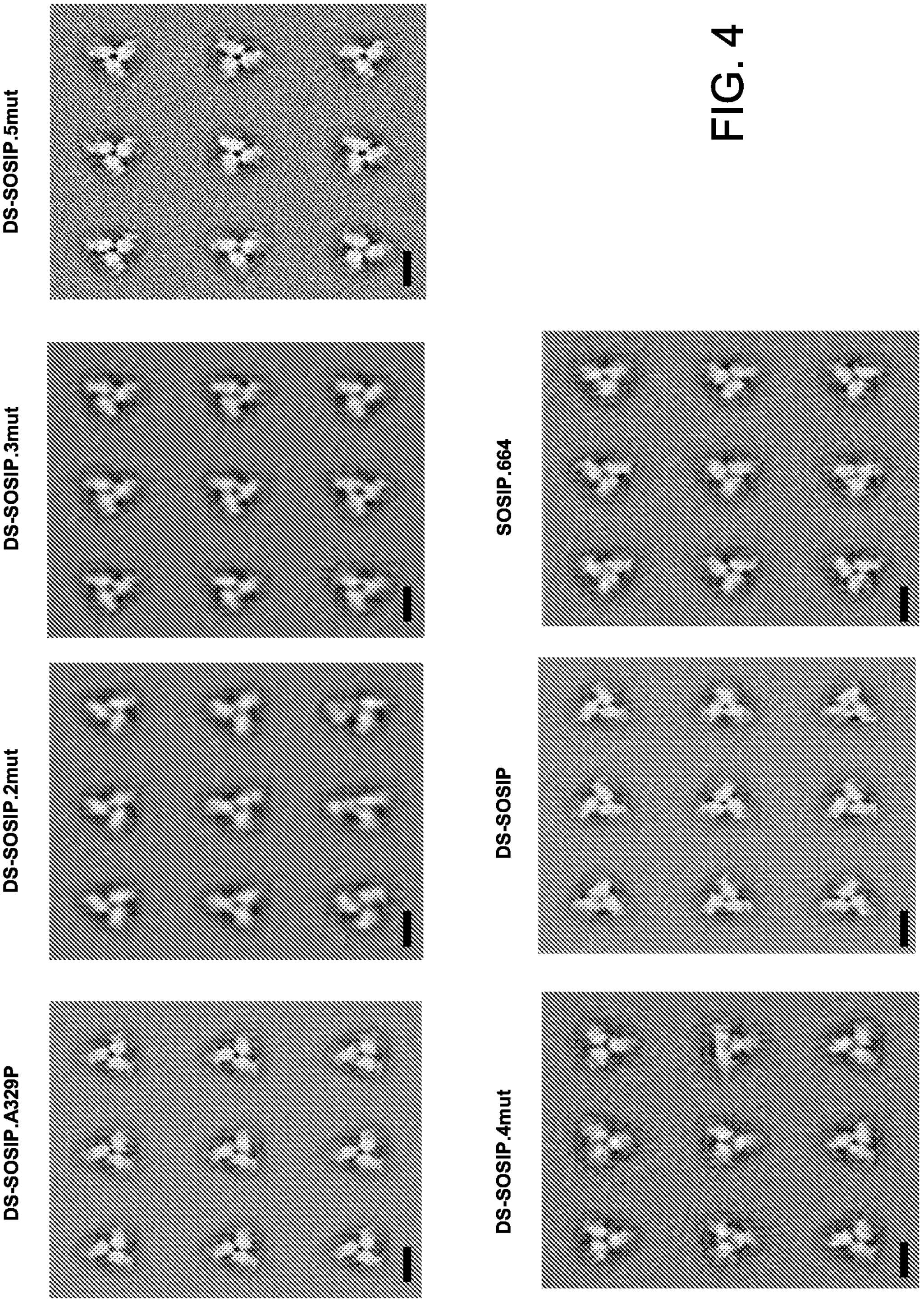
FIG. 4. Negative-stain electron microscopy of stabilized Env trimers. Reference-free classification and averaging produced symmetrical propeller-like classes typical of the prefusion-closed conformation of the HIV-1 envelope trimer, indicative of high homogeneity and correct folding/assembly of the proteins. Scale bars are 10 nm.

Negative Stain Electron Microscopy. To determine whether the introduction of the designed mutations altered structural conformation relative to DS-SOSIP, negative-stain electron microscopy (EM) was performed on the purified design variants (FIG. 4) after SEC and V3-negative selection. Similar to DS-SOSIP and SOSIP.664, DS-SOSIP.A329P, DS-SOSIP.2mut, DS-SOSIP.3mut, DS-SOSIP.4mut, and DS-SOSIP.5mut uniformly formed trimers in the prefusion closed conformation without monomers and aggregates. In particular, visual inspection of the 2D classes revealed compact propeller-like shapes typical of the closed prefusion conformation. There were no classes corresponding to the open conformation or nonnative trimers as defined by Pugach et al. (Pugach et al. 2015. *J Virol* 89:3380-3295).

Figure 5A:
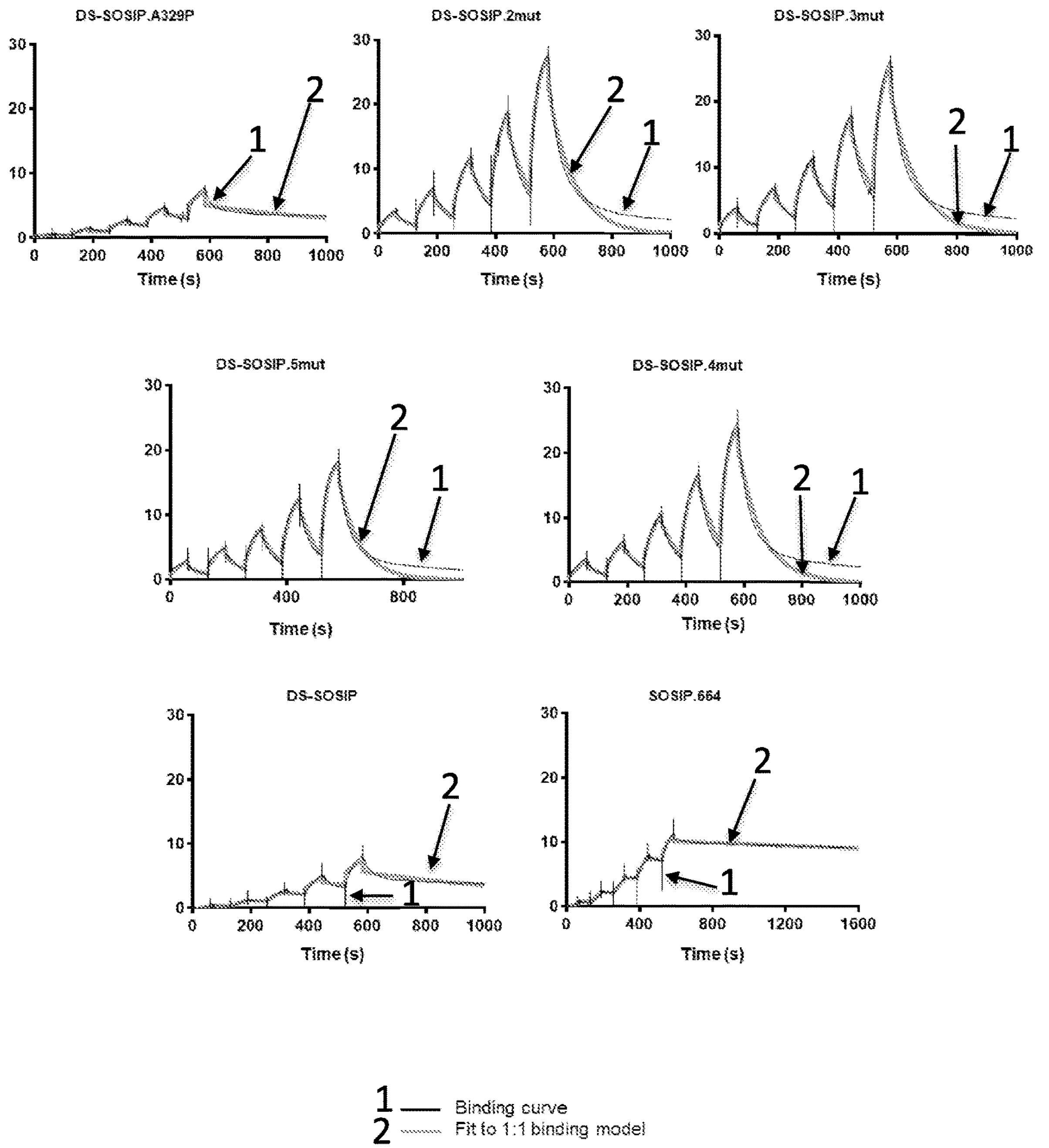

CD4 binding. To determine whether DS-SOSIP.3mut demonstrated a difference in CD4 binding relative to DS-SOSIP, the binding of sCD4 to DS-SOSIP.A329P, DS-SOSIP.2mut, DS-SOSIP.3mut, DS-SOSIP.4mut, DS-SOSIP.5mut, DS-SOSIP, and DS-SOSIP.664 was measured using surface plasmon resonance (SPR) (FIG. 5). DS-SOSIP.3mut showed substantially lower sCD4 binding affinity ($K_d$ reduced by ~30-40-fold) compared with DS-SOSIP ($K_d$=11 nM), which was already reduced substantially from that of SOSIP.664 ($K_d$=1.4 nM).

Figure 6:
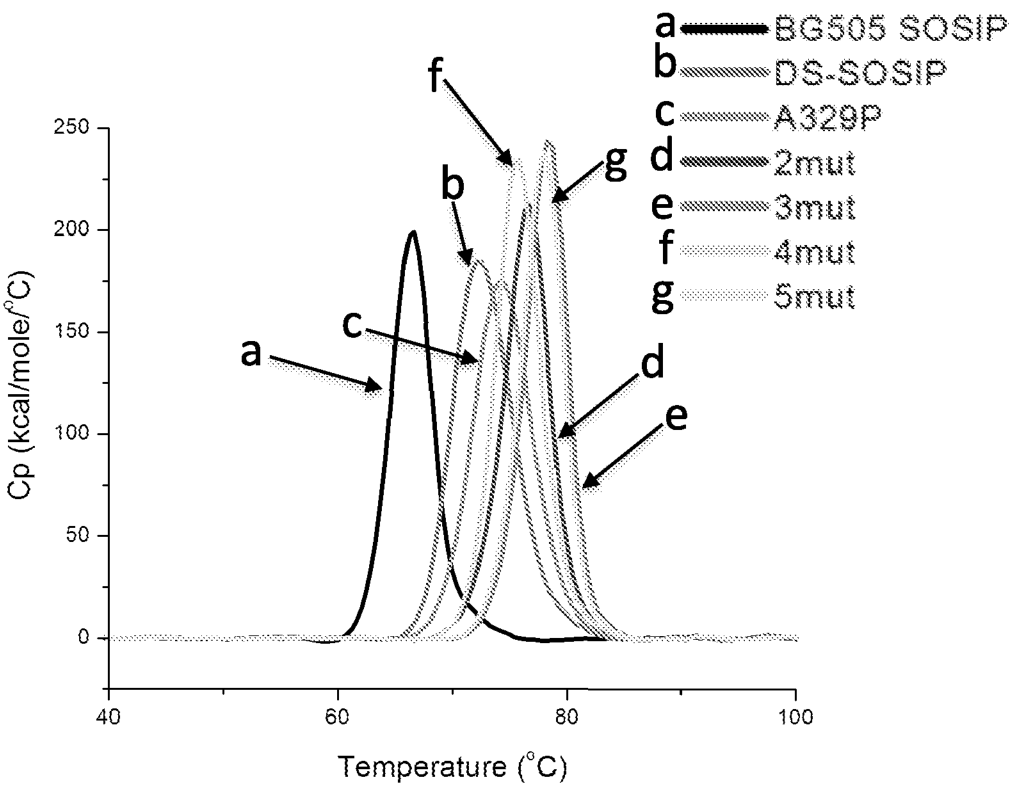
FIG. 6. Thermostability of stabilized HIV-1 Env trimers assessed by differential scanning calorimetry (DSC). Top: Raw data from DSC shown in solid lines. Bottom: $T_m$, $\Delta T_{1/2}$, and enthalpy of unfolding from DSC (ΔH).

Thermostability of DS-SOSIP.3mut. The thermostability of DS-SOSIP, SOSIP.664, DS-SOSIP.A329P, DS-SOSIP.2mut, DS-SOSIP.3mut, DS-SOSIP.4mut, and DS-SOSIP.5mut was assessed by differential scanning calorimetry (DSC) (FIG. 6). Of the variants tested, DS-SOSIP.3mut showed the greatest increase in melting temperature ($T_m$) relative to DS-SOSIP, with an approximately seven degree increase in $T_m$ (to 78.7° C.) relative to DS-SOSIP (72.0° C.).

Conclusion. In summary, this example describes development of the "3mut" set of mutations for stabilizing HIV-1 Env in its prefusion mature closed conformation. One example, DS-SOSIP.3mut, a, a BG505 SOSIP.6R.664 variant, is shown to be stabilized in the prefusion-closed conformation with improved antigenicity and thermostability relative to prior HIV-1 Env trimers. The DS-SOSIP.3mut trimer showed substantial reduction of weakly neutralizing antigenicity prior to V3-negative selection relative to DS-SOSIP and DS-SOSIP.4mut, indicating reduction of spontaneous V3 transition. The results suggest that this trimer may be suitable for genetic immunization, where the antigenic quality of the immunogen without purification may be relevant.

DS-SOSIP.3mut displayed affinity for CD4 of approximately 400 nM, yet retained binding affinity for broadly neutralizing antibodies that target the CD4 binding site, such as VRC01. While a number of other stabilized forms of Env have been reported (de Taeye et al. 2015. *Cell* 163:1702-1715; Cheng et al. 2015. *J Virol* 90:2740-2755; Steichen et al. 2016. *Immunity* 45:483-496; Sharma et al. 2015. *Cell Rep* 11:539-550; Georgiev et al. 2015. *J Virol* 89:5318-5329; Kong et al. 2016. *Nat Commun* 7:12040), none of these prior studies report low CD4 affinity while maintaining recognition of CD4-binding site antibodies. The stabilizing mutations of DS-SOSIP.3mut (N302M/T320L/A329P) can be added to HIV-1 Env immunogens to improve their various properties, for example, as provided herein as CAP256-wk34c80-RnS-3mut-2G_FP8v2 (SEQ ID NO: 19) and ConC_Base0_3mut_2G_FP8v2 (SEQ ID NO: 21). In addition, DS-SOSIP.3mut trimers have utility as serological probes to isolate antibodies that target the prefusion-closed conformation of Env.

Materials and Methods

Protein expression and purification. The various BG505 DS-SOSIP trimer mutants were produced in 293 FreeStyle cells, as described previously (Sanders et al. 2013. PLoS Pathog 9:e1003618). Briefly, 600 μg of BG505 DS-SOSIP trimer construct was co-transfected with 150 μg of furin plasmid DNA into 1 liter of cells. After 6 days, the transfected supernatants were harvested, filtered, and loaded over a VRC01-affinity column. After washing with phosphate-buffered saline (PBS), the bounded proteins were eluted with 3 M $MgCl_2$ and 30 mM Tris at a pH of 7.0. The eluate was concentrated to 2-3 ml using Amicon Ultracel-50K (Millipore) and applied to a Superdex200 16/600 gel filtration column (GE Healthcare) equilibrated in PBS. The peak corresponding to trimeric HIV-1 Env was identified, pooled and subjected to negative selection with 447-52D (PDB ID: 4M1D) (Killikelly et al. 2013. Biochemistry 52:6249-6257) and V3 cocktail columns to remove aberrant trimer species (Kwon et al. 2015. Nat Struct Mol Biol 22:522-531). The V3 cocktail column contains 6 V3-directed antibodies: 1006-15D, 2219, 2557, 2558, 3074, and 50.1 (PDB ID: 3MLW (Jiang et al. 2010. Nat Struct Mol Biol 17:955-961), 2B0S (Stanfield et al. 2006. J Virol 80:6093-6105), 3MLS (Jiang et al. 2010. Nat Struct Mol Biol 17:955-961), 3UJI (Gorny et al. 2011. PLoS One 6:e27780), 3MLX (Jiang et al. 2010. Nat Struct Mol Biol 17:955-961), and IGGI (Rini et al. 1993. *PNAS* 90:6325-6329)).

Antigenic analysis of DS-SOSIP variants by MSD-ECLIA. Standard 96-well bare multi-array Meso Scale Discovery (MSD) Plates (MSD, Cat #L15XA-3) were coated with a panel of HIV neutralizing (VRC01 (Wu et al. 2010. Science 329:856-861), b12 (Zhou et al. 2007. Nature 445: 732-737), VRC13 (Zhou et al. 2015. Cell 161:1280-1292), PGT121 (Walker et al. 2011. Nature 477:466-470), PGT128 (Walker et al. 2011. Nature 477:466-470), 2G12 (Calarese et al. 2003. Science 300:2065-2071), PGT145 (Walker et al. 2011. Nature 477:466-470), CAP256-VRC26.25 (Doria-Rose et al. 2015. J Virol 90:76-91), 35022 (Huang et al. 2014. Nature doi:10.1038/nature13601), and 8ANC195 (Scheid et al. 2009. Nature 458:636-640), PGT151 (Falkowska et al. 2014. Immunity 40:657-668)), non- or weakly neutralizing monoclonal (F105 (Chen et al. 2009. Science 326:1123-1127), 17b (Kwong et al. 1998. Nature 393:648-659) (+sCD4), 48D (Thali et al. 1993. J Virol 67:3978-3988) (+sCD4) and 447-52D (Killikelly et al. 2013. Biochemistry 52:6249-6257) (+sCD4), 3074 (Gorny et al. 2006. J Virol 80:6865-6872) (+sCD4), 2557 (Jiang et al. 2010. Nat Struct Mol Biol 17:955-961) (+sCD4)), and non-cognate antibodies (anti-influenza antibodies CR9114 (Dreyfus et al. 2012. Science 337:1343-1348) and anti-RSV antibodies, D25 (McLellan et al. 2013. Science 340:1113-1117)) in duplicate (30 μL/well) at a concentration of 4 μg/mL diluted in 1×PBS by incubating overnight at 4° C. The following day, the plates were washed (wash buffer: 0.05% Tween-20+1×PBS) and blocked with 150 μL of blocking buffer (5% [W/V] MSD Blocker A (MSD, Cat #R93BA-4)) by incubating for 1 hr on a vibrational shaker (Heidolph TITRAMAX 100; Cat #P/N: 544-11200-00) at 650 rpm. All incubations were performed at room temperature except the coating step. During the incubation, BG505 DS-SOSIP trimers were titrated in serial 2× dilutions starting at a concentration of 5 μg/mL of the trimer in the assay diluent (1% [W/V] MSD blocker A+0.05% Tween-20). For soluble CD4 (sCD4) induction, the trimer was combined with sCD4 at a constant molar concentration of 1 μM before being added to the MSD plate. After the incubation with blocking buffer was complete, the plates were washed, and the diluted trimer was transferred (25 μl/well) to the MSD plates and incubated for 2 hr on the vibrational shaker at 650 rpm. After the 2 hr incubation with trimer, the plates were washed again and 2G12 antibody labeled with MSD SULFOTAG (MSD; Cat #R91AO-1) at a conjugation ratio of 1:15 (2G12:SULFO-TAG) which was diluted in assay diluent at 2 ug/mL, added to the plates (25 μL/well), and incubated for 1 hr on the vibrational shaker at 650 rpm. The plates were washed and read using 1× read buffer (MSD Read Buffer T (4×); Cat #R92TC-1) on the MSD Sector Imager 2400.

Negative-stain electron microscopy. The samples were diluted to approximately 0.02 mg/ml, adsorbed to a freshly glow-discharged carbon-film grid for 15 s, and stained with 0.7% uranyl formate at a pH of 5. Images were collected semi-automatically using SerialEM on an FEI Tecnai T20 microscope operating at 200 kV and equipped with a 2k×2k Eagle CCD camera. The pixel size was 0.22 nm/px. Particles were selected using the swarm mode in e2boxer from the EMAN2 software package. Reference-free 2D class averages were obtained using EMAN2.

Surface plasmon resonance analysis. Binding affinities and kinetics of soluble CD4 (sCD4) to HIV-1 DS-SOSIP various trimers were assessed by single-cycle kinetics analysis using surface plasmon resonance on Biacore T-200 (GE Healthcare) at 25° C. with HBS-EP+ buffer (10 mM HEPES, pH 7.4, 150 mM NaCl, 3 mM EDTA and 0.05% surfactant P-20). Frist, 2G12 antibody was immobilized on flow cells of a CM5 chip at ~2000 response unit. Next, 200 nM of trimer was captured onto the sample flow cell at a flow rate of 5 μl/min for 120 s. Finally, sCD4 at five concentrations was injected incrementally in a single cycle, starting from the lowest concentration at a flow rate of 50 ul/min for 60 s, which was followed by a dissociation phase of 30 min. Blank sensorgrams were obtained by injection of the same volume of HBS-EP+ buffer in place of sCD4. Sensorgrams of the concentration series were corrected with corresponding blank curves and fitted globally with Biacore T200 evaluation software with a 1:1 Langnuir model of binding.

Differential scanning calorimetry. A high-precision differential scanning VP-DSC microcalorimeter (GE Healthcare/MicroCal) was employed to measure the heat capacity of the trimers. In brief, samples were diluted to 0.3 mg/ml with PBS. Thermal denaturation scans were performed from 30° C. to 110° C. at a rate of 1° C./min.

Example 2

Recombinant HIV-1 Env Ectodomain Trimers Stabilized in a Prefusion Closed Confirmation This example illustrates additional HIV-1 Env ectodomain trimers containing the 3mut substitutions for stabilization in the prefusion closed confirmation.

The 3mut substitutions were added to several different HIV-1 Env sequences, including the following, to generate prefusion closed HIV-1 Env trimers:

```
4-2.J41-BGSP-jcb_01.3mut
                                            (SEQ ID NO: 31)
MDSKGSSQKGSRLLLLLVVSNLLLPQGVLAAVEKLWVTVYYGVPVWKDAK

TTLFCASDAKAYDTEVHNVWATHACVPTDPNPQEMLLDNVTENFNMWKND

MVDQMHEDVISLWDQSLKPCVKLTPLCVTLECTDSSNQTHYNESMQEIKN

CTFNVTTEIRDRKQRVQALFYKLDIVSLEKNSSTYRLINCNTSACTQACP

KVTFDPIPIHYCTPAGYAILKCNNETFNGTGPCRNVSTVQCTHGIKPVVS

TQLLLNGSLAEKDIMIRSENLTDNAKTIIVHLNQTVEIVCIRPNNMTRQS

IRIGPGQVFYALGDIIGDIRQPYCTINTTAWNETLQRVSKKLAEHFPNKT

IRFAPSSGGDLEITTHSFNCRGEFFYCNTSGLFNSTYMTNGTFTYKLNDT

NITIPCRIKQIINMWQEVGRCMYAPPIAGNITCKSNITGMLLVRDGGKNE

NSTEETFRPGGGNMRDNWRSELYKYKVVEIKPLGVAPTKCKRRVVGRRRR

RRAVGIGAVFLGFLGAAGSTMGAASMTLTVQARNLLSGIVQQQSNLLRAP

EAQQHLLKLTVWGIKQLQARVLAVERYLRDQQLLGIWGCSGKLICCTNVP

WNSSWSNRNLSEIWDNMTWLQWDKEISNYTQIIYGLLEESQNQQEKNEQD

LLALD

BGSP-jcb_04.3mut
                                            (SEQ ID NO: 32)
MDSKGSSQKGSRLLLLLVVSNLLLPQGVLAAENLWVTVYYGVPVWKDAET

TLFCASDAKAYETEKHNVWATHACVPTDPNPQEIHLENVTEEFNMWKNNM

VEQMHTDIISLWDQSLKPCVKLTPLCVTLQCTNVTNNITDDMRGELKNCS

FNMTTELRDKKQKVYSLFYRLDVVQINENQGNRSNNSNKEYRLINCNTSA

CTQACPKVSFEPIPIHYCAPAGFAILKCKDKKFNGTGPCPSVSTVQCTHG

IKPVVSTQLLLNGSLAEEEVMIRSENITNNAKNILVQFNTPVQINCTRPN

NMTRKSIRIGPGQAFYALGDIIGDIRQPHCNVSKATWNETLGKVVKQLRK

HFGNNTIIRFANSSGGDLEVTTHSFNCGGEFFYCNTSGLFNSTWISNTSV

QGSNSTGSNDSITLPCRIKQIINMWQRIGQCMYAPPIQGVIRCVSNITGL

ILTRDGGSTNSTTETFRPGGGDMRDNWRSELYKYKVVKIEPLGVAPTRCK
```

-continued

```
RRVVGNSTHKQLTHHMRRRRRRAVGIGAVFLGFLGAAGSTMGAASMTLTV

QARNLLSGIVQQQSNLLRAPEAQQHLLKLTVWGIKQLQARVLAVERYLRD

QQLLGIWGCSGKLICCTNVPWNSSWSNRNLSEIWDNMTWLQWDKEISNYT

QIIYGLLEESQNQQEKNEQDLLALD

4-2.J41-BGSP-jcb_01.3mut
                                            (SEQ ID NO: 35)
MDSKGSSQKGSRLLLLLVVSNLLLPQGVLAAVEKLWVTVYYGVPVWKDAK

TTLFCASDAKAYDTEVHNVWATHACVPTDPNPQEMLLDNVTENFNMWKND

MVDQMHEDVISLWDQSLKPCVKLTPLCVTLECTDSSNQTHYNESMQEIKN

CTFNVTTEIRDRKQRVQALFYKLDIVSLEKNSSTYRLINCNTSACTQACP

KVTFDPIPIHYCTPAGYAILKCNNETFNGTGPCRNVSTVQCTHGIKPVVS

TQLLLNGSLAEKDIMIRSENLTDNAKTIIVHLNQTVEIVCIRPNNMTRQS

IRIGPGQVFYALGDIIGDIRQPYCTINTTAWNETLQRVSKKLAEHFPNKT

IRFAPSSGGDLEITTHSFNCRGEFFYCNTSGLFNSTYMTNGTFTYKLNDT

NITIPCRIKQIINMWQEVGRCMYAPPIAGNITCKSNITGMLLVRDGGKNE

NSTEETFRPGGGNMRDNWRSELYKYKVVEIKPLGVAPTKCKRRVVGRRRR

RRAVGIGAVFLGFLGAAGSTMGAASMTLTVQARNLLSGIVQQQSNLLRAP

EAQQHLLKLTVWGIKQLQARVLAVERYLRDQQLLGIWGCSGKLICCTNVP

WNSSWSNRNLSEIWDNMTWLQWDKEISNYTQIIYGLLEESQNQQEKNEQD

LLALD

BGSP-jcb_04.3mut
                                            (SEQ ID NO: 36)
MDSKGSSQKGSRLLLLLVVSNLLLPQGVLAAENLWVTVYYGVPVWKDAET

TLFCASDAKAYETEKHNVWATHACVPTDPNPQEIHLENVTEEFNMWKNNM

VEQMHTDIISLWDQSLKPCVKLTPLCVTLQCTNVTNNITDDMRGELKNCS

FNMTTELRDKKQKVYSLFYRLDVVQINENQGNRSNNSNKEYRLINCNTSA

CTQACPKVSFEPIPIHYCAPAGFAILKCKDKKFNGTGPCPSVSTVQCTHG

IKPVVSTQLLLNGSLAEEEVMIRSENITNNAKNILVQFNTPVQINCTRPN

NMTRKSIRIGPGQAFYALGDIIGDIRQPHCNVSKATWNETLGKVVKQLRK

HFGNNTIIRFANSSGGDLEVTTHSFNCGGEFFYCNTSGLFNSTWISNTSV

QGSNSTGSNDSITLPCRIKQIINMWQRIGQCMYAPPIQGVIRCVSNITGL

ILTRDGGSTNSTTETFRPGGGDMRDNWRSELYKYKVVKIEPLGVAPTRCK

RRVVGNSTHKQLTHHMRRRRRRAVGIGAVFLGFLGAAGSTMGAASMTLTV

QARNLLSGIVQQQSNLLRAPEAQQHLLKLTVWGIKQLQARVLAVERYLRD

QQLLGIWGCSGKLICCTNVPWNSSWSNRNLSEIWDNMTWLQWDKEISNYT

QIIYGLLEESQNQQEKNEQDLLALD
```

Figure 7:
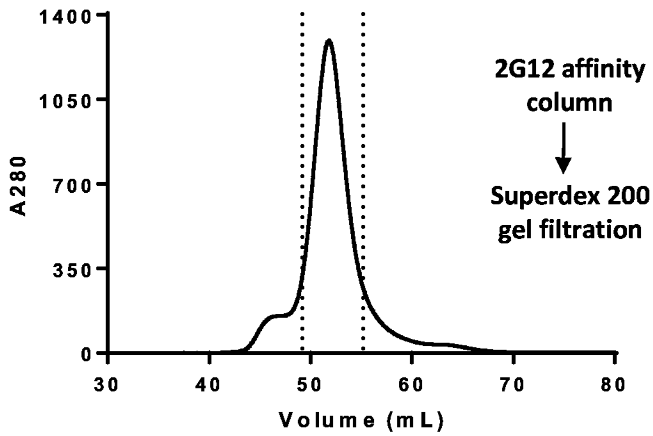
FIG. 7. Characterization of Cap256-RnS-3mut-2G-FP8v2. The Cap256-RnS-3mut-2G-FP8v2 trimer was expressed in cells and purified from the corresponding supernatant with a 2G12 affinity column followed by superdex 200 gel filtration. The elution profile is shown. Purified protein was separated by SDS-Page with and without reducing agent, and the resulting coomassie stained gel is shown. Protein yield was 5.8 mg/L. The purified protein was further analyzed by negative stain electron microscopy. 2D class averages confirmed that the purified trimer is in the prefusion closed conformation.
Figure 7:
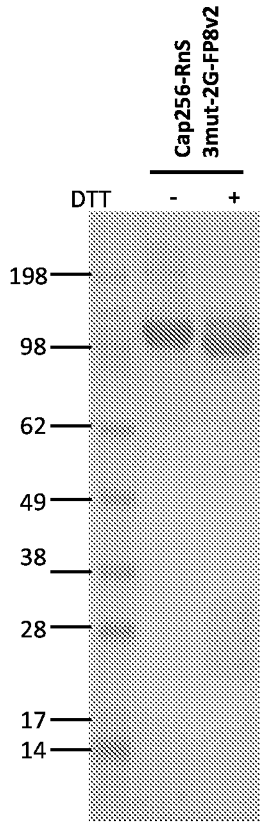
Figure 7:
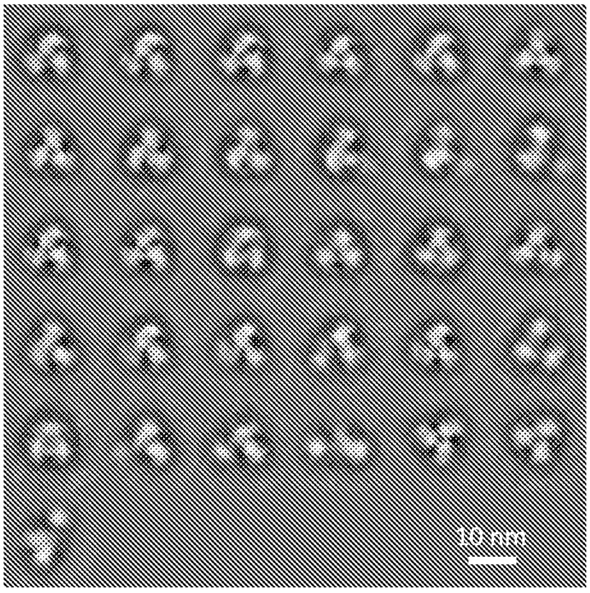
Figure 8:
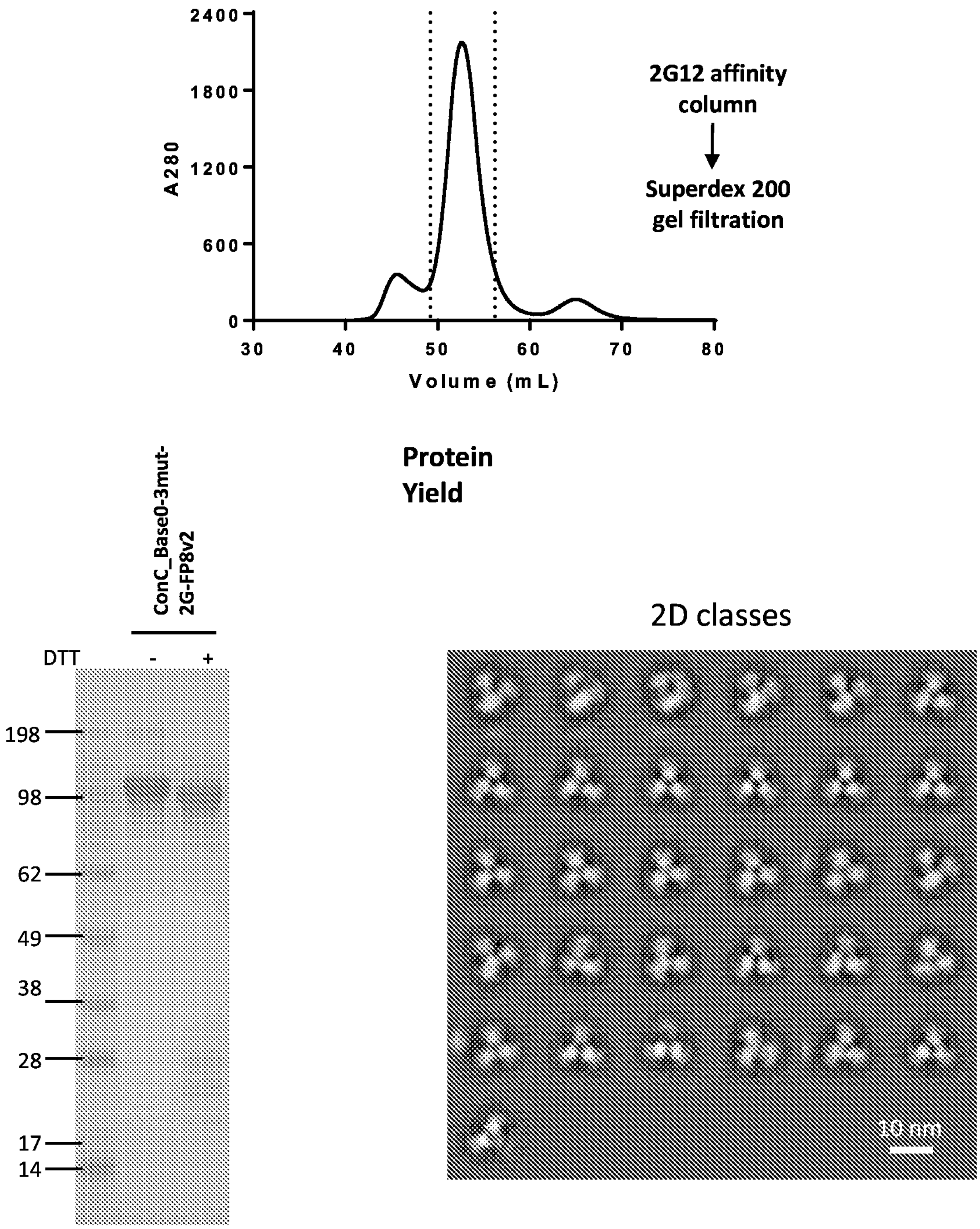
FIG. 8. Characterization of ConC_Base-3mut-2G-FP8v2. The ConC_Base-3mut-2G-FP8v2 trimer was expressed in cells and purified from the corresponding supernatant with a 2G12 affinity column followed by superdex 200 gel filtration. The elution profile is shown. Purified protein was separated by SDS-Page with and without reducing agent, and the resulting coomassie stained gel is shown. Protein yield was 10.2 mg/L. The purified protein was further analyzed by negative stain electron microscopy. 2D class averages confirmed that the purified trimer in the prefusion closed conformation.

The Cap256-RnS-3mut-2G-FP8v2 and ConC_Base0-3mut-2G-FP8v2 trimers were expressed in cells and purified from the corresponding supernatant with a 2G12 affinity column followed by superdex 200 gel filtration (FIGS. 7 and 8). Protein yield was 5.8 mg/L for Cap256-RnS-3mut-2G-FP8v2 and 10.2 mg/L for ConC_Base0-3mut-2G-FP8v2. The purified trimers were further analyzed by negative stain electron microscopy, and 2D class averages confirmed that the trimers are in the prefusion closed conformation.

Figure 9A:
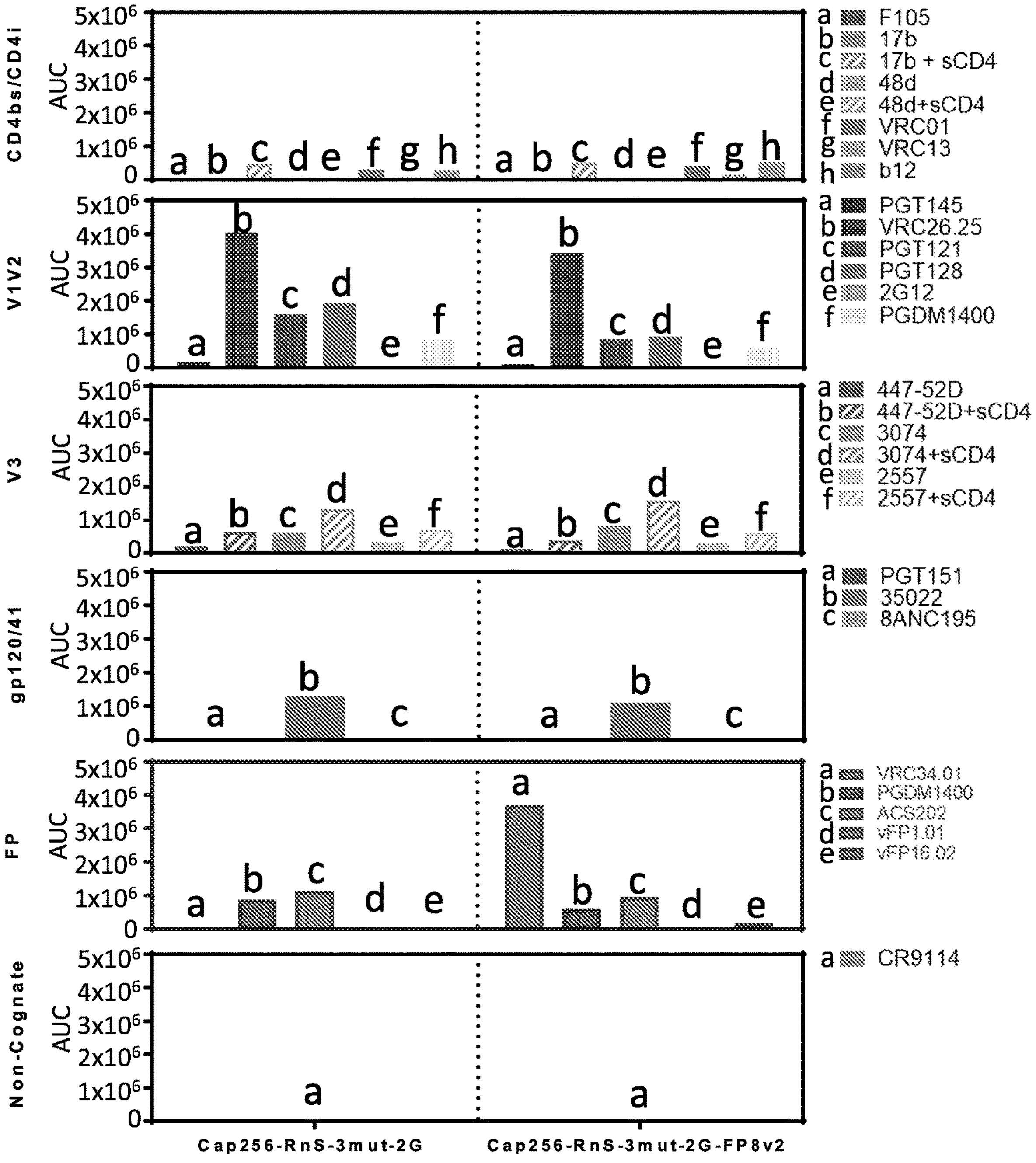
FIGS. 9A and 9B. Antigenicity of stabilized Env trimer as determined by Meso Scale Discovery (MSD). Antigenicity of (FIG. 9A) Cap256-RnS-3mut-2G and Cap256-RnS-3mut-2G-FP8v2, and (FIG. 9B) BG505.DS-SOSIP, Janssen-7mut, and ConC_Base0-3mut-2G-FP8v2, after V3-negative selection assessed on a panel of antibodies including CD4-induced antibodies (17b and 48d, with and without soluble CD4), CD4-binding site antibodies (VRC01, VRC13 and b12), V2-apex-directed antibodies (PGT145, CAP256-VRC26.25), glycan-V3 antibodies (PGT121, PGT128 and 2G12), weakly neutralizing V3-directed antibodies (447-52D, 3074 and 2557, with and without soluble CD4), gp41-gp120 interface antibodies (PGT151, 35022 and 8ANC195) and fusion peptide antibody (VRC34.01).
Figure 9B:
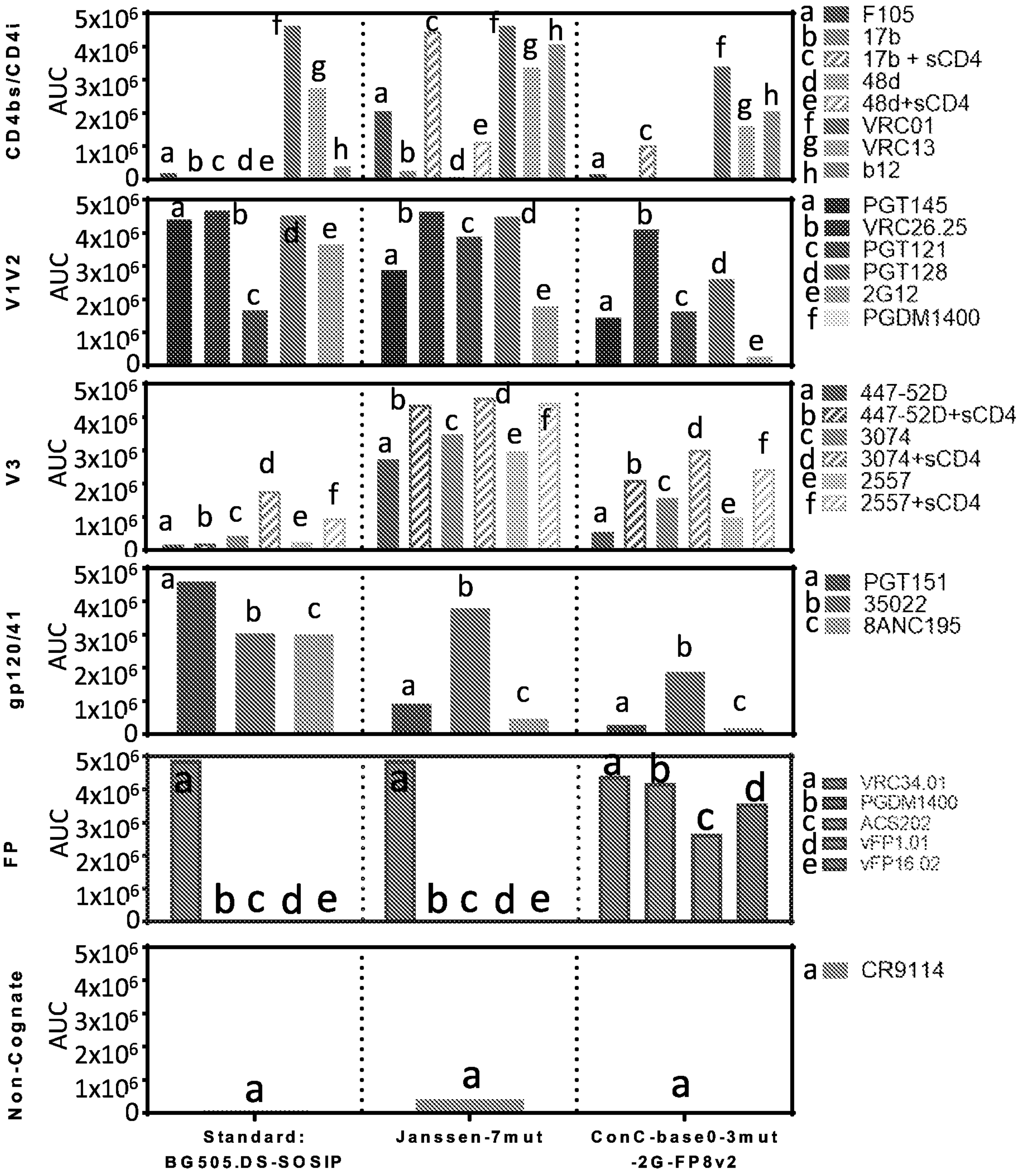

Antigenicity of Cap256-RnS-3mut-2G-FP8v2 and ConC_Base0-3mut-2G-FP8v2 trimers, as well as several other HIV-1 Env trimers, after V3-negative selection was assessed on a panel of CD4-induced antibodies (17b and 48d, with and without soluble CD4), CD4-binding site antibodies (VRC01, VRC13 and b12), V2-apex-directed antibodies (PGT145, CAP256-VRC26.25), glycan-V3 antibodies (PGT121, PGT128 and 2G12), weakly neutralizing V3-directed antibodies (447-52D, 3074 and 2557, with and without soluble CD4), gp41-gp120 interface antibodies (PGT151, 35022 and 8ANC195) and fusion peptide antibody (VRC34.01) FIGS. 9A and 9B).

Figure 10:
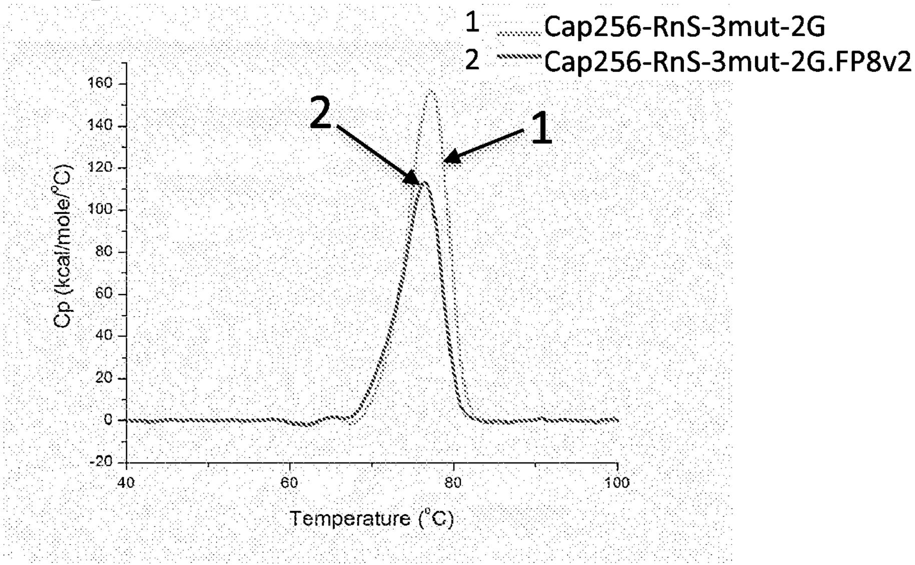
FIG. 10. Thermostability of Cap256-RnS-3mut-2G-FP8v2 and ConC_Base0-3mut-2G-FP8v2.
Figure 10:
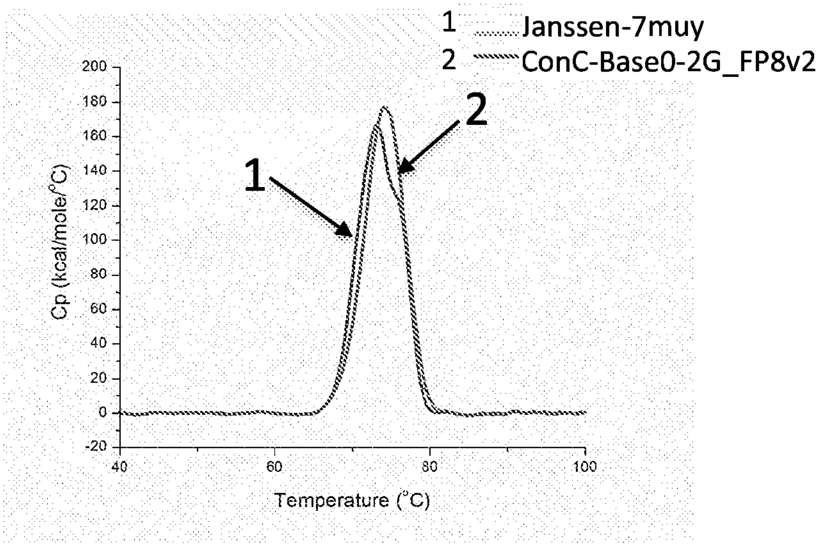

Finally, the thermostability of Cap256-RnS-3mut-2G-FP8v2 and ConC_Base0-3mut-2G-FP8v2 trimers was assessed by differential scanning calorimetry (DSC) (FIG. 10).

It will be apparent that the precise details of the methods or compositions described may be varied or modified without departing from the spirit of the described embodiments. We claim all such modifications and variations that fall within the scope and spirit of the claims below.

It is claimed:

1. A recombinant HIV-1 envelope (Env) ectodomain trimer stabilized in a prefusion closed conformation by amino acid substitutions in protomers of the trimer, the amino acid substitutions comprising:

cysteine substitutions at HIV-1 Env positions 501 and 605 that form a non-natural intra-protomer disulfide bond;
a proline substitution at HIV-1 Env position 559;
a methionine substitution at HIV-1 Env position 302;
a leucine substitution at HIV-1 Env position 320; and
a proline substitution at HIV-1 Env position 329; and
wherein the HIV-1 Env ectodomain trimer elicits an immune response to HIV-1.

2. The recombinant HIV-1 Env ectodomain trimer of claim 1, wherein the protomers of the trimer further comprise cysteine substitutions at HIV-1 Env positions 201 and 433 that form a non-natural intra-protomer disulfide bond.

3. The recombinant HIV-1 Env ectodomain trimer of claim 1, wherein:

the cysteine substitutions at HIV-1 Env positions 201 and 433 are I201C and A433C substitutions;
the cysteine substitutions at HIV-1 Env positions 501 and 605 are A501C and T605C substitutions;
the proline substitution at HIV-1 Env position 559 is a I559P substitution;
the methionine substitution at HIV-1 Env position 302 is a N302M substitution;
the leucine substitution at HIV-1 Env position 320 is a T320L substitution; and/or
the proline substitution at HIV-1 Env position 329 is a A329P substitution.

4. The recombinant HIV-1 Env ectodomain trimer of claim 1, wherein the protomers of the trimer comprise a substitution of any one of RRRRRR (SEQ ID NO: 8), GRRRRRR (SEQ ID NO: 27), GGSGRRRRRR (SEQ ID NO: 28), GRRRRRRRRR (SEQ ID NO: 29), or GNSTHKQLTHHMRRRRRR (SEQ ID NO: 30) for the amino acids of a gp120/gp41 furin cleavage site.

5. The recombinant HIV-1 Env ectodomain trimer of claim 1, wherein the protomers of the recombinant HIV-1 Env ectodomain trimer further comprise one or more amino acid substitutions to introduce an N-linked glycosylation site at position 332 if the N-linked glycosylation site is not already present.

6. The recombinant HIV-1 Env ectodomain trimer of claim 1, wherein the protomers of the recombinant HIV-1 Env ectodomain trimer further comprises one or more additional amino acid substitutions.

7. The recombinant HIV-1 Env ectodomain trimer of claim 1, wherein the recombinant HIV-1 Env ectodomain trimer is selected from one of:

a recombinant Clade A HIV-1 Env ectodomain trimer, a recombinant Clade B HIV-1 Env ectodomain trimer, a recombinant Clade C HIV-1 Env ectodomain trimer, a recombinant Clade D HIV-1 Env ectodomain trimer, or a recombinant Clade F HIV-1 Env ectodomain trimer;
that comprises the amino acid substitutions.

8. The recombinant HIV-1 Env ectodomain trimer of claim 1, wherein the protomers of the recombinant HIV-1 Env ectodomain trimer comprise a gp120 protein comprising or consisting of HIV-1 Env positions 31-507 and a gp41 ectodomain comprising or consisting of HIV-1 Env positions 512-664.

9. The recombinant HIV-1 Env ectodomain trimer of claim 1, wherein the HIV-1 Env ectodomain trimer binds to sCD4 with an affinity of tighter than 350 nM.

10. The recombinant HIV-1 Env ectodomain trimer of claim 1, wherein the protomers of the HIV-1 Env ectodomain trimer comprise an amino acid sequence at least 90% identical to any one of SEQ ID NOs: 3, 5, 19, 21, 23, 24, or 31-32.

11. The recombinant HIV-1 Env ectodomain trimer of claim 1, wherein the protomers of the HIV-1 Env ectodomain trimer comprise the amino acid sequence set forth as any one of SEQ ID NOs: 3, 5, 19, 21, 23, 24, or 31-32.

12. The recombinant HIV-1 Env ectodomain trimer of claim 1, wherein the recombinant HIV-1 Env ectodomain trimer is soluble.

13. The recombinant HIV-1 Env ectodomain trimer of claim 1, wherein the protomers of the recombinant HIV-1 Env ectodomain trimer comprise a C-terminal residue linked to a trimerization domain by a peptide linkers, or directly linked to the trimerization domain.

14. The recombinant HIV-1 Env ectodomain trimer of claim 13, wherein the trimerization domain is a T4 Fibritin trimerization domain.

15. The recombinant HIV-1 Env ectodomain trimer of claim 1, conjugated to a heterologous carrier.

16. The recombinant HIV-1 Env ectodomain trimer of claim 15, wherein the carrier comprises Keyhole Limpet Hemocyanin (KLH), Concholepas Concholepas Hemocyanin (CCH), Ovalbumin (OVA), bovine serum albumin, recombinant *B. anthracis* protective antigen, recombinant *P. aeruginosa* exotoxin A, tetanus toxoid, tetanus toxin heavy chain C fragment, diphtheria toxoid, diphtheria toxin variant CRM197, pertussis toxoid, H influenza protein D (HiD), recombinant *Clostridium difficile* toxin B subunit (rBRU), *C. perfringens* toxoid, or analogs or mimetics of and combinations of two or more thereof.

17. The recombinant HIV-1 Env ectodomain trimer of claim 1, wherein the protomers of the recombinant HIV-1 Env ectodomain trimer comprise a C-terminal residue linked to a transmembrane domain by a peptide linker, or directly linked to the transmembrane domain.

18. The recombinant HIV-1 Env ectodomain trimer of claim 17, wherein the protomers of the recombinant HIV-1 Env ectodomain trimer comprise a full-length gp41 protein.

19. A protein nanoparticle comprising the recombinant HIV-1 Env ectodomain trimer of claim 1, wherein the protomers of the recombinant HIV-1 Env ectodomain trimer are linked to subunits of the protein nanoparticle by a peptide linker, or are directly linked to the protein nanoparticle subunits.

20. The protein nanoparticle of claim 19, wherein the protein nanoparticle is a lumazine synthase nanoparticle and the subunits are lumazine synthase subunits, the protein nanoparticle is a ferritin nanoparticle and the subunits are ferritin subunits or the protein nanoparticle is an encapsulin nanoparticle and the subunits are encapsulin subunits.

21. A virus-like particle comprising the HIV-1 Env ectodomain trimer of claim 1.

22. A nucleic acid molecule encoding a protomer of the recombinant HIV-1 Env ectodomain trimer or the protomer of the HIV-1 Env trimer linked to the protein nanoparticle subunit of claim 1.

23. The isolated nucleic acid molecule of claim 22, encoding a precursor of the protomer of the recombinant HIV-1 Env ectodomain trimer.

24. The isolated nucleic acid molecule of claim 22, comprising a nucleic acid sequence set forth as SEQ ID NO: 17.

25. The nucleic acid molecule of claim 22, operably linked to a promoter.

26. The isolated nucleic acid molecule of claim 22, wherein the nucleic acid molecule is an RNA molecule.

27. A vector comprising the nucleic acid molecule of claim 25.

28. An immunogenic composition for use to elicit an immune response to HIV-1 in a subject, comprising the recombinant HIV-1 Env ectodomain trimer of claim 1, and a pharmaceutically acceptable carrier.

29. The immunogenic composition of claim 28, further comprising an adjuvant.

30. A method of producing a recombinant HIV-1 Env ectodomain trimer, comprising:

expressing the nucleic acid molecule of claim 21 in a host cell; and purifying the recombinant HIV-1 Env ectodomain trimer.

31. A method for eliciting an immune response to HIV-1 in a subject, comprising administering to the subject an effective amount of the recombinant HIV-1 Env ectodomain trimer of claim 1 to elicit the immune response.

32. The method of claim 31, wherein the immune response treats or inhibits HIV-1 infection in the subject.

* * * * *

SEQUENCE LISTING

```
<160> NUMBER OF SEQ ID NOS: 38

<210> SEQ ID NO 1
<211> LENGTH: 856
<212> TYPE: PRT
<213> ORGANISM: human immunodeficiency virus

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300
```

```
Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
```

```
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855


<210> SEQ ID NO 2
<211> LENGTH: 634
<212> TYPE: PRT
<213> ORGANISM: Artificial sequence
<220> FEATURE:
<223> OTHER INFORMATION: Recombinant HIV-1 envelope protein

<400> SEQUENCE: 2

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Cys Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
```

-continued

```
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Cys Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 3

```
<211> LENGTH: 634
<212> TYPE: PRT
<213> ORGANISM: Artificial sequence
<220> FEATURE:
<223> OTHER INFORMATION: Recombinant HIV-1 envelope protein

<400> SEQUENCE: 3

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Cys Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Met
            260                 265                 270

Thr Arg Lys Ser Ile Arg Ile Gly Pro Gly Gln Ala Phe Tyr Ala Leu
        275                 280                 285

Gly Asp Ile Ile Gly Asp Ile Arg Gln Pro His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380
```

Pro Cys Arg Ile Lys Gln Ile Ile Asn Met Trp Gln Arg Ile Gly Gln
385 390 395 400

Cys Met Tyr Ala Pro Pro Ile Gln Gly Val Ile Arg Cys Val Ser Asn
405 410 415

Ile Thr Gly Leu Ile Leu Thr Arg Asp Gly Gly Ser Thr Asn Ser Thr
420 425 430

Thr Glu Thr Phe Arg Pro Gly Gly Gly Asp Met Arg Asp Asn Trp Arg
435 440 445

Ser Glu Leu Tyr Lys Tyr Lys Val Val Lys Ile Glu Pro Leu Gly Val
450 455 460

Ala Pro Thr Arg Cys Lys Arg Arg Val Val Gly Arg Arg Arg Arg Arg
465 470 475 480

Arg Ala Val Gly Ile Gly Ala Val Phe Leu Gly Phe Leu Gly Ala Ala
485 490 495

Gly Ser Thr Met Gly Ala Ala Ser Met Thr Leu Thr Val Gln Ala Arg
500 505 510

Asn Leu Leu Ser Gly Ile Val Gln Gln Gln Ser Asn Leu Leu Arg Ala
515 520 525

Pro Glu Ala Gln Gln His Leu Leu Lys Leu Thr Val Trp Gly Ile Lys
530 535 540

Gln Leu Gln Ala Arg Val Leu Ala Val Glu Arg Tyr Leu Arg Asp Gln
545 550 555 560

Gln Leu Leu Gly Ile Trp Gly Cys Ser Gly Lys Leu Ile Cys Cys Thr
565 570 575

Asn Val Pro Trp Asn Ser Ser Trp Ser Asn Arg Asn Leu Ser Glu Ile
580 585 590

Trp Asp Asn Met Thr Trp Leu Gln Trp Asp Lys Glu Ile Ser Asn Tyr
595 600 605

Thr Gln Ile Ile Tyr Gly Leu Leu Glu Glu Ser Gln Asn Gln Gln Glu
610 615 620

Lys Asn Glu Gln Asp Leu Leu Ala Leu Asp
625 630

<210> SEQ ID NO 4
<211> LENGTH: 662
<212> TYPE: PRT
<213> ORGANISM: Artificial sequence
<220> FEATURE:
<223> OTHER INFORMATION: Recombinant HIV-1 envelope protein

<400> SEQUENCE: 4

Ser Arg Ala Thr Met Pro Met Gly Ser Leu Gln Pro Leu Ala Thr Leu
1 5 10 15

Tyr Leu Leu Gly Met Leu Val Ala Ser Val Leu Ala Ala Glu Asn Leu
20 25 30

Trp Val Thr Val Tyr Tyr Gly Val Pro Val Trp Lys Asp Ala Glu Thr
35 40 45

Thr Leu Phe Cys Ala Ser Asp Ala Lys Ala Tyr Glu Thr Glu Lys His
50 55 60

Asn Val Trp Ala Thr His Ala Cys Val Pro Thr Asp Pro Asn Pro Gln
65 70 75 80

Glu Ile His Leu Glu Asn Val Thr Glu Glu Phe Asn Met Trp Lys Asn
85 90 95

Asn Met Val Glu Gln Met His Thr Asp Ile Ile Ser Leu Trp Asp Gln
100 105 110

-continued

```
Ser Leu Lys Pro Cys Val Lys Leu Thr Pro Leu Cys Val Thr Leu Gln
        115                 120                 125

Cys Thr Asn Val Thr Asn Asn Ile Thr Asp Asp Met Arg Gly Glu Leu
    130                 135                 140

Lys Asn Cys Ser Phe Asn Met Thr Thr Glu Leu Arg Asp Lys Lys Gln
145                 150                 155                 160

Lys Val Tyr Ser Leu Phe Tyr Arg Leu Asp Val Val Gln Ile Asn Glu
                165                 170                 175

Asn Gln Gly Asn Arg Ser Asn Asn Ser Asn Lys Glu Tyr Arg Leu Ile
            180                 185                 190

Asn Cys Asn Thr Ser Ala Cys Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Lys Asp Lys Lys Phe Asn Gly Thr Gly Pro Cys Pro Ser Val
225                 230                 235                 240

Ser Thr Val Gln Cys Thr His Gly Ile Lys Pro Val Val Ser Thr Gln
                245                 250                 255

Leu Leu Leu Asn Gly Ser Leu Ala Glu Glu Glu Val Met Ile Arg Ser
            260                 265                 270

Glu Asn Ile Thr Asn Asn Ala Lys Asn Ile Leu Val Gln Phe Asn Thr
        275                 280                 285

Pro Val Gln Ile Asn Cys Thr Arg Pro Asn Asn Met Thr Arg Lys Ser
    290                 295                 300

Ile Arg Ile Gly Pro Gly Gln Ala Phe Tyr Ala Leu Gly Asp Ile Ile
305                 310                 315                 320

Gly Asp Ile Arg Gln Pro His Cys Asn Val Ser Lys Ala Thr Trp Asn
                325                 330                 335

Glu Thr Leu Gly Lys Val Val Lys Gln Leu Arg Lys His Phe Gly Asn
            340                 345                 350

Asn Thr Ile Ile Arg Phe Ala Asn Ser Ser Gly Gly Asp Leu Glu Val
        355                 360                 365

Thr Thr His Ser Phe Asn Cys Gly Gly Glu Phe Phe Tyr Cys Asn Thr
    370                 375                 380

Ser Gly Leu Phe Asn Ser Thr Trp Ile Ser Asn Thr Ser Val Gln Gly
385                 390                 395                 400

Ser Asn Ser Thr Gly Ser Asn Asp Ser Ile Thr Leu Pro Cys Arg Ile
                405                 410                 415

Lys Gln Ile Ile Asn Met Trp Gln Arg Ile Gly Gln Cys Met Tyr Ala
            420                 425                 430

Pro Pro Ile Gln Gly Val Ile Arg Cys Val Ser Asn Ile Thr Gly Leu
        435                 440                 445

Ile Leu Thr Arg Asp Gly Gly Ser Thr Asn Ser Thr Thr Glu Thr Phe
    450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Arg
                485                 490                 495

Cys Lys Arg Arg Val Val Gly Arg Arg Arg Arg Arg Arg Ala Val Gly
            500                 505                 510

Ile Gly Ala Val Phe Leu Gly Phe Leu Gly Ala Ala Gly Ser Thr Met
        515                 520                 525
```

Gly Ala Ala Ser Met Thr Leu Thr Val Gln Ala Arg Asn Leu Leu Ser
530 535 540

Gly Ile Val Gln Gln Gln Ser Asn Leu Leu Arg Ala Pro Glu Ala Gln
545 550 555 560

Gln His Leu Leu Lys Leu Thr Val Trp Gly Ile Lys Gln Leu Gln Ala
565 570 575

Arg Val Leu Ala Val Glu Arg Tyr Leu Arg Asp Gln Gln Leu Leu Gly
580 585 590

Ile Trp Gly Cys Ser Gly Lys Leu Ile Cys Cys Thr Asn Val Pro Trp
595 600 605

Asn Ser Ser Trp Ser Asn Arg Asn Leu Ser Glu Ile Trp Asp Asn Met
610 615 620

Thr Trp Leu Gln Trp Asp Lys Glu Ile Ser Asn Tyr Thr Gln Ile Ile
625 630 635 640

Tyr Gly Leu Leu Glu Glu Ser Gln Asn Gln Gln Glu Lys Asn Glu Gln
645 650 655

Asp Leu Leu Ala Leu Asp
660

<210> SEQ ID NO 5
<211> LENGTH: 623
<212> TYPE: PRT
<213> ORGANISM: Artificial sequence
<220> FEATURE:
<223> OTHER INFORMATION: Recombinant HIV-1 envelope protein

<400> SEQUENCE: 5

Ala Glu Asn Leu Trp Val Thr Val Tyr Tyr Gly Val Pro Val Trp Lys
1 5 10 15

Glu Ala Lys Thr Thr Leu Phe Cys Ala Ser Asp Ala Lys Ala Tyr Glu
20 25 30

Lys Glu Val His Asn Val Trp Ala Thr His Ala Cys Val Pro Thr Asp
35 40 45

Pro Asn Pro Gln Glu Met Val Leu Lys Asn Val Thr Glu Asn Phe Asn
50 55 60

Met Trp Lys Asn Asp Met Val Asp Gln Met His Glu Asp Val Ile Ser
65 70 75 80

Leu Trp Asp Gln Ser Leu Lys Pro Cys Val Lys Leu Thr Pro Leu Cys
85 90 95

Val Thr Leu Asn Cys Thr Asn Ala Thr Ala Ser Asn Ser Ser Ile Ile
100 105 110

Glu Gly Met Lys Asn Cys Ser Phe Asn Ile Thr Thr Glu Leu Arg Asp
115 120 125

Lys Arg Glu Lys Lys Asn Ala Leu Phe Tyr Lys Leu Asp Ile Val Gln
130 135 140

Leu Asp Gly Asn Ser Ser Gln Tyr Arg Leu Ile Asn Cys Asn Thr Ser
145 150 155 160

Val Cys Thr Gln Ala Cys Pro Lys Val Ser Phe Asp Pro Ile Pro Ile
165 170 175

His Tyr Cys Ala Pro Ala Gly Tyr Ala Ile Leu Lys Cys Asn Asn Lys
180 185 190

Thr Phe Thr Gly Thr Gly Pro Cys Asn Asn Val Ser Thr Val Gln Cys
195 200 205

Thr His Gly Ile Lys Pro Val Val Ser Thr Gln Leu Leu Leu Asn Gly
210 215 220

```
Ser Leu Ala Glu Gly Glu Ile Ile Ile Arg Ser Glu Asn Ile Thr Asn
225                 230                 235                 240

Asn Val Lys Thr Ile Ile Val His Leu Asn Glu Ser Val Lys Ile Glu
                245                 250                 255

Cys Thr Arg Pro Asn Asn Lys Thr Arg Thr Ser Ile Arg Ile Gly Pro
            260                 265                 270

Gly Gln Ala Phe Tyr Ala Thr Gly Gln Val Ile Gly Asp Ile Arg Glu
        275                 280                 285

Ala Tyr Cys Asn Ile Asn Glu Ser Lys Trp Asn Glu Thr Leu Gln Arg
    290                 295                 300

Val Ser Lys Lys Leu Lys Glu Tyr Phe Pro His Lys Asn Ile Thr Phe
305                 310                 315                 320

Gln Pro Ser Ser Gly Gly Asp Leu Glu Ile Thr Thr His Ser Phe Asn
                325                 330                 335

Cys Gly Gly Glu Phe Phe Tyr Cys Asn Thr Ser Ser Leu Phe Asn Arg
            340                 345                 350

Thr Tyr Met Ala Asn Ser Thr Asp Met Ala Asn Ser Thr Glu Thr Asn
        355                 360                 365

Ser Thr Arg Thr Ile Thr Ile His Cys Arg Ile Lys Gln Ile Ile Asn
    370                 375                 380

Met Trp Gln Glu Val Gly Arg Cys Met Tyr Ala Pro Pro Ile Ala Gly
385                 390                 395                 400

Asn Ile Thr Cys Ile Ser Asn Ile Thr Gly Leu Leu Leu Thr Arg Asp
                405                 410                 415

Gly Gly Lys Asn Asn Thr Glu Thr Phe Arg Pro Gly Gly Gly Asn Met
            420                 425                 430

Lys Asp Asn Trp Arg Ser Glu Leu Tyr Lys Tyr Lys Val Val Lys Ile
        435                 440                 445

Glu Pro Leu Gly Val Ala Pro Thr Arg Cys Lys Arg Arg Val Val Gly
    450                 455                 460

Arg Arg Arg Arg Arg Arg Ala Val Gly Ile Gly Ala Val Phe Leu Gly
465                 470                 475                 480

Phe Leu Gly Ala Ala Gly Ser Thr Met Gly Ala Ala Ser Met Thr Leu
                485                 490                 495

Thr Val Gln Ala Arg Asn Leu Leu Ser Gly Ile Val Gln Gln Gln Ser
            500                 505                 510

Asn Leu Leu Arg Ala Pro Glu Ala Gln Gln His Leu Leu Lys Leu Thr
        515                 520                 525

Val Trp Gly Ile Lys Gln Leu Gln Ala Arg Val Leu Ala Val Glu Arg
    530                 535                 540

Tyr Leu Arg Asp Gln Gln Leu Leu Gly Ile Trp Gly Cys Ser Gly Lys
545                 550                 555                 560

Leu Ile Cys Cys Thr Asn Val Pro Trp Asn Ser Ser Trp Ser Asn Arg
                565                 570                 575

Asn Leu Ser Glu Ile Trp Asp Asn Met Thr Trp Leu Gln Trp Asp Lys
            580                 585                 590

Glu Ile Ser Asn Tyr Thr Gln Ile Ile Tyr Gly Leu Leu Glu Glu Ser
        595                 600                 605

Gln Asn Gln Gln Glu Lys Asn Glu Gln Asp Leu Leu Ala Leu Asp
    610                 615                 620
```

```
<210> SEQ ID NO 6
<211> LENGTH: 623
<212> TYPE: PRT
```

<213> ORGANISM: Artificial sequence
<220> FEATURE:
<223> OTHER INFORMATION: Recombinant HIV-1 envelope protein

<400> SEQUENCE: 6

```
Ala Glu Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
        35                  40                  45

Pro Asn Pro Gln Glu Met Val Leu Lys Asn Val Thr Glu Asn Phe Asn
    50                  55                  60

Met Trp Lys Asn Asp Met Val Asp Gln Met His Glu Asp Val Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asn Ala Thr Ala Ser Asn Ser Ser Ile Ile
            100                 105                 110

Glu Gly Met Lys Asn Cys Ser Phe Asn Ile Thr Thr Glu Leu Arg Asp
        115                 120                 125

Lys Arg Glu Lys Lys Asn Ala Leu Phe Tyr Lys Leu Asp Ile Val Gln
    130                 135                 140

Leu Asp Gly Asn Ser Ser Gln Tyr Arg Leu Ile Asn Cys Asn Thr Ser
145                 150                 155                 160

Val Cys Thr Gln Ala Cys Pro Lys Val Ser Phe Asp Pro Ile Pro Ile
                165                 170                 175

His Tyr Cys Ala Pro Ala Gly Tyr Ala Ile Leu Lys Cys Asn Asn Lys
            180                 185                 190

Thr Phe Thr Gly Thr Gly Pro Cys Asn Asn Val Ser Thr Val Gln Cys
        195                 200                 205

Thr His Gly Ile Lys Pro Val Val Ser Thr Gln Leu Leu Leu Asn Gly
    210                 215                 220

Ser Leu Ala Glu Gly Glu Ile Ile Ile Arg Ser Glu Asn Ile Thr Asn
225                 230                 235                 240

Asn Val Lys Thr Ile Ile Val His Leu Asn Glu Ser Val Lys Ile Glu
                245                 250                 255

Cys Thr Arg Pro Asn Asn Met Thr Arg Thr Ser Ile Arg Ile Gly Pro
            260                 265                 270

Gly Gln Ala Phe Tyr Ala Leu Gly Gln Val Ile Gly Asp Ile Arg Glu
        275                 280                 285

Pro Tyr Cys Asn Ile Asn Glu Ser Lys Trp Asn Glu Thr Leu Gln Arg
    290                 295                 300

Val Ser Lys Lys Leu Lys Glu Tyr Phe Pro His Lys Asn Ile Thr Phe
305                 310                 315                 320

Gln Pro Ser Ser Gly Gly Asp Leu Glu Ile Thr Thr His Ser Phe Asn
                325                 330                 335

Cys Gly Gly Glu Phe Phe Tyr Cys Asn Thr Ser Ser Leu Phe Asn Arg
            340                 345                 350

Thr Tyr Met Ala Asn Ser Thr Asp Met Ala Asn Ser Thr Glu Thr Asn
        355                 360                 365

Ser Thr Arg Thr Ile Thr Ile His Cys Arg Ile Lys Gln Ile Ile Asn
    370                 375                 380

Met Trp Gln Glu Val Gly Arg Cys Met Tyr Ala Pro Pro Ile Ala Gly
```

```
385                 390                 395                 400

Asn Ile Thr Cys Ile Ser Asn Ile Thr Gly Leu Leu Leu Thr Arg Asp
                405                 410                 415

Gly Gly Lys Asn Asn Thr Glu Thr Phe Arg Pro Gly Gly Gly Asn Met
            420                 425                 430

Lys Asp Asn Trp Arg Ser Glu Leu Tyr Lys Tyr Lys Val Val Lys Ile
        435                 440                 445

Glu Pro Leu Gly Val Ala Pro Thr Arg Cys Lys Arg Arg Val Val Gly
    450                 455                 460

Arg Arg Arg Arg Arg Arg Ala Val Gly Ile Gly Ala Val Phe Leu Gly
465                 470                 475                 480

Phe Leu Gly Ala Ala Gly Ser Thr Met Gly Ala Ala Ser Met Thr Leu
                485                 490                 495

Thr Val Gln Ala Arg Asn Leu Leu Ser Gly Ile Val Gln Gln Gln Ser
            500                 505                 510

Asn Leu Leu Arg Ala Pro Glu Ala Gln Gln His Leu Leu Lys Leu Thr
        515                 520                 525

Val Trp Gly Ile Lys Gln Leu Gln Ala Arg Val Leu Ala Val Glu Arg
    530                 535                 540

Tyr Leu Arg Asp Gln Gln Leu Leu Gly Ile Trp Gly Cys Ser Gly Lys
545                 550                 555                 560

Leu Ile Cys Cys Thr Asn Val Pro Trp Asn Ser Ser Trp Ser Asn Arg
                565                 570                 575

Asn Leu Ser Glu Ile Trp Asp Asn Met Thr Trp Leu Gln Trp Asp Lys
            580                 585                 590

Glu Ile Ser Asn Tyr Thr Gln Ile Ile Tyr Gly Leu Leu Glu Glu Ser
        595                 600                 605

Gln Asn Gln Gln Glu Lys Asn Glu Gln Asp Leu Leu Ala Leu Asp
    610                 615                 620
```

<210> SEQ ID NO 7
<211> LENGTH: 4
<212> TYPE: PRT
<213> ORGANISM: Artificial sequence
<220> FEATURE:
<223> OTHER INFORMATION: Furin cleavage site

<400> SEQUENCE: 7

```
Arg Glu Lys Arg
1
```

<210> SEQ ID NO 8
<211> LENGTH: 6
<212> TYPE: PRT
<213> ORGANISM: Artificial sequence
<220> FEATURE:
<223> OTHER INFORMATION: Furin cleavage site

<400> SEQUENCE: 8

```
Arg Arg Arg Arg Arg Arg
1               5
```

<210> SEQ ID NO 9
<211> LENGTH: 10
<212> TYPE: PRT
<213> ORGANISM: Artificial sequence
<220> FEATURE:
<223> OTHER INFORMATION: Peptide linker

<400> SEQUENCE: 9

```
Gly Gly Ser Gly Gly Gly Gly Ser Gly Gly
1               5                   10


<210> SEQ ID NO 10
<211> LENGTH: 27
<212> TYPE: PRT
<213> ORGANISM: Artificial sequence
<220> FEATURE:
<223> OTHER INFORMATION: Transmembrane domain

<400> SEQUENCE: 10

Lys Ile Phe Ile Met Ile Val Gly Gly Leu Ile Gly Leu Arg Ile Val
1               5                   10                  15

Phe Ala Val Leu Ser Val Ile His Arg Val Arg
            20                  25


<210> SEQ ID NO 11
<211> LENGTH: 23
<212> TYPE: PRT
<213> ORGANISM: Artificial sequence
<220> FEATURE:
<223> OTHER INFORMATION: Transmembrane domain

<400> SEQUENCE: 11

Ile Leu Ala Ile Tyr Ser Thr Val Ala Ser Ser Leu Val Leu Leu Val
1               5                   10                  15

Ser Leu Gly Ala Ile Ser Phe
            20


<210> SEQ ID NO 12
<211> LENGTH: 29
<212> TYPE: PRT
<213> ORGANISM: Artificial sequence
<220> FEATURE:
<223> OTHER INFORMATION: Transmembrane domain

<400> SEQUENCE: 12

Ile Ile Thr Ile Gly Ser Ile Cys Met Val Val Gly Ile Ile Ser Leu
1               5                   10                  15

Ile Leu Gln Ile Gly Asn Ile Ile Ser Ile Trp Val Ser
            20                  25


<210> SEQ ID NO 13
<211> LENGTH: 26
<212> TYPE: PRT
<213> ORGANISM: Artificial sequence
<220> FEATURE:
<223> OTHER INFORMATION: T4 fibritin domain

<400> SEQUENCE: 13

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25


<210> SEQ ID NO 14
<211> LENGTH: 154
<212> TYPE: PRT
<213> ORGANISM: Artificial sequence
<220> FEATURE:
<223> OTHER INFORMATION: Recombinant protein nanoparticle subunit

<400> SEQUENCE: 14

Met Gln Ile Tyr Glu Gly Lys Leu Thr Ala Glu Gly Leu Arg Phe Gly
```

```
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150


<210> SEQ ID NO 15
<211> LENGTH: 173
<212> TYPE: PRT
<213> ORGANISM: Artificial sequence
<220> FEATURE:
<223> OTHER INFORMATION: Recombinant protein nanoparticle subunit

<400> SEQUENCE: 15

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Cys Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170


<210> SEQ ID NO 16
<211> LENGTH: 265
<212> TYPE: PRT
<213> ORGANISM: Artificial sequence
<220> FEATURE:
<223> OTHER INFORMATION: Recombinant protein nanoparticle subunit
```

<400> SEQUENCE: 16

Met Glu Phe Leu Lys Arg Ser Phe Ala Pro Leu Thr Glu Lys Gln Trp
1 5 10 15

Gln Glu Ile Asp Asn Arg Ala Arg Glu Ile Phe Lys Thr Gln Leu Tyr
20 25 30

Gly Arg Lys Phe Val Asp Val Glu Gly Pro Tyr Gly Trp Glu Tyr Ala
35 40 45

Ala His Pro Leu Gly Glu Val Glu Val Leu Ser Asp Glu Asn Glu Val
50 55 60

Val Lys Trp Gly Leu Arg Lys Ser Leu Pro Leu Ile Glu Leu Arg Ala
65 70 75 80

Thr Phe Thr Leu Asp Leu Trp Glu Leu Asp Asn Leu Glu Arg Gly Lys
85 90 95

Pro Asn Val Asp Leu Ser Ser Leu Glu Glu Thr Val Arg Lys Val Ala
100 105 110

Glu Phe Glu Asp Glu Val Ile Phe Arg Gly Cys Glu Lys Ser Gly Val
115 120 125

Lys Gly Leu Leu Ser Phe Glu Glu Arg Lys Ile Glu Cys Gly Ser Thr
130 135 140

Pro Lys Asp Leu Leu Glu Ala Ile Val Arg Ala Leu Ser Ile Phe Ser
145 150 155 160

Lys Asp Gly Ile Glu Gly Pro Tyr Thr Leu Val Ile Asn Thr Asp Arg
165 170 175

Trp Ile Asn Phe Leu Lys Glu Glu Ala Gly His Tyr Pro Leu Glu Lys
180 185 190

Arg Val Glu Glu Cys Leu Arg Gly Gly Lys Ile Ile Thr Thr Pro Arg
195 200 205

Ile Glu Asp Ala Leu Val Val Ser Glu Arg Gly Gly Asp Phe Lys Leu
210 215 220

Ile Leu Gly Gln Asp Leu Ser Ile Gly Tyr Glu Asp Arg Glu Lys Asp
225 230 235 240

Ala Val Arg Leu Phe Ile Thr Glu Thr Phe Thr Phe Gln Val Val Asn
245 250 255

Pro Glu Ala Leu Ile Leu Leu Lys Phe
260 265

<210> SEQ ID NO 17
<211> LENGTH: 1904
<212> TYPE: DNA
<213> ORGANISM: Artificial sequence
<220> FEATURE:
<223> OTHER INFORMATION: Recombinant HIV-1 envelope protein

<400> SEQUENCE: 17
gccgaaaacc tgtgggtcac cgtgtattat ggagtgcccg tctggaaaga tgctgaaact 60
accctgttct gtgcctctga tgctaaggcc tacgagaccg aaaagcacaa tgtctgggct 120
actcatgcat gcgtgcccac cgacccaaac cccaggaga tccacctgga aaatgtgacc 180
gaggaattca acatgtggaa aaacaatatg gtggagcaga tgcatacaga catcattagc 240
ctgtgggatc agtccctgaa gccctgcgtc aaactgactc ctctgtgcgt gaccctgcag 300
tgtaccaatg tcacaaacaa tatcaccgac gatatgaggg gcgagctgaa gaattgtagc 360
ttcaacatga ccacagaact gagagacaag aaacagaaag tgtactccct gttttatagg 420
ctggatgtgg tccagatcaa tgagaaccag gggaatcgga gcaacaattc caacaaggaa 480

```
tacagactga tcaattgcaa cacttccgcc tgtacccagg cttgtcctaa agtgtctttt    540
gagcctatcc caattcatta ttgcgcccca gctggcttcg ccatcctgaa gtgtaaagat    600
aagaagttca acggaactgg cccctgccct tccgtgtcta cagtccagtg tactcacggg    660
attaagcctg tggtctctac acagctgctg ctgaatggaa gtctggctga ggaagaagtg    720
atgatccgga gcgagaacat taccaacaat gccaagaata tcctggtcca gttcaacaca    780
ccagtgcaga ttaattgcac aagacccaac aatatgactc gaaaatctat ccggattggg    840
ccaggacagg ccttttacgc tctgggggac atcattggag atatcagaca gcctcactgt    900
aatgtgagta aggcaacctg gaacgagaca ctgggcaagg tggtcaaaca gctgaggaaa    960
catttcggga ataacaccat cattcgcttt gccaatagct ccggaggggga cctggaggtc   1020
actacccact ccttcaactg cggaggcgaa ttcttttact gtaacacatc tggcctgttt   1080
aatagtacat ggatctctaa cactagtgtg cagggcagta attcaactgg gtcaaacgat   1140
agcatcaccc tgccatgccg aattaagcag atcattaata tgtggcagcg gatcggccag   1200
tgcatgtatg cccccccctat ccagggggtc attcgctgcg tgagcaatat caccggactg   1260
attctgacac gagacggggg cagcaccaac tctacaactg aaacattccg gcccggcggg   1320
ggagacatga gagataactg gaggtccgag ctgtacaagt ataaagtggt caagatcgaa   1380
cctctgggag tggcaccaac cagatgcaag cgaagagtgg tcggacgaag gaggaggagg   1440
cgagcagtcg gaattggggc cgtgttcctg ggatttctgg gcgccgctgg gagtacaatg   1500
ggagcagcct caatgactct gaccgtgcag gccaggaatc tgctgagcgg catcgtccag   1560
cagcagtcca acctgctgcg cgctcctgaa gcacagcagc acctgctgaa gctgaccgtg   1620
tggggcatca aacagctgca ggctagggtg ctggcagtcg agcggtacct gagagaccag   1680
cagctgctgg gaatctgggg ctgctctggg aagctgattt gttgcacaaa tgtgccttgg   1740
aactctagtt ggtcaaatcg caacctgagc gagatctggg acaatatgac ttggctgcag   1800
tgggataaag aaattagtaa ctacacccag atcatctacg gcctgctgga agagtcacag   1860
aatcagcagg agaagaacga acaggacctg ctggctctgg attg                     1904
```

```
<210> SEQ ID NO 18
<211> LENGTH: 1988
<212> TYPE: DNA
<213> ORGANISM: Artificial sequence
<220> FEATURE:
<223> OTHER INFORMATION: Recombinant HIV-1 envelope protein

<400> SEQUENCE: 18
```

```
tctagagcca ccatgcctat ggggagcctg cagcctctgg caaccctgta tctgctggga     60
atgctggtcg caagtgtcct ggccgccgaa aacctgtggg tcaccgtgta ttatggagtg    120
cccgtctgga aagatgctga aactaccctg ttctgtgcct ctgatgctaa ggcctacgag    180
accgaaaagc acaatgtctg ggctactcat gcatgcgtgc ccaccgaccc aaacccccag    240
gagatccacc tggaaaatgt gaccgaggaa ttcaacatgt ggaaaaacaa tatggtggag    300
cagatgcata cagacatcat tagcctgtgg gatcagtccc tgaagccctg cgtcaaactg    360
actcctctgt gcgtgaccct gcagtgtacc aatgtcacaa acaatatcac cgacgatatg    420
aggggcgagc tgaagaattg tagcttcaac atgaccacag aactgagaga caagaaacag    480
aaagtgtact ccctgtttta taggctggat gtggtccaga tcaatgagaa ccaggggaat    540
cggagcaaca attccaacaa ggaatacaga ctgatcaatt gcaacacttc cgcctgtacc    600
```

-continued

```
caggcttgtc ctaaagtgtc ttttgagcct atcccaattc attattgcgc cccagctggc    660

ttcgccatcc tgaagtgtaa agataagaag ttcaacggaa ctggcccctg cccttccgtg    720

tctacagtcc agtgtactca cgggattaag cctgtggtct ctacacagct gctgctgaat    780

ggaagtctgg ctgaggaaga agtgatgatc cggagcgaga acattaccaa caatgccaag    840

aatatcctgg tccagttcaa cacaccagtg cagattaatt gcacaagacc caacaatatg    900

actcgaaaat ctatccggat tggccagga caggcctttt acgctctggg ggacatcatt    960

ggagatatca gacagcctca ctgtaatgtg agtaaggcaa cctggaacga gacactgggc   1020

aaggtggtca aacagctgag gaaacatttc gggaataaca ccatcattcg ctttgccaat   1080

agctccggag gggacctgga ggtcactacc cactccttca actgcggagg cgaattcttt   1140

tactgtaaca catctggcct gtttaatagt acatggatct ctaacactag tgtgcagggc   1200

agtaattcaa ctgggtcaaa cgatagcatc accctgccat gccgaattaa gcagatcatt   1260

aatatgtggc agcggatcgg ccagtgcatg tatgccccc ctatccaggg ggtcattcgc   1320

tgcgtgagca atatcaccgg actgattctg acacgagacg gggcagcac caactctaca   1380

actgaaacat tccggcccgg cgggggagac atgagagata actggaggtc cgagctgtac   1440

aagtataaag tggtcaagat cgaacctctg ggagtggcac caaccagatg caagcgaaga   1500

gtggtcggac gaaggaggag gaggcgagca gtcggaattg ggccgtgtt cctgggattt   1560

ctgggcgccg ctgggagtac aatgggagca gcctcaatga ctctgaccgt gcaggccagg   1620

aatctgctga gcggcatcgt ccagcagcag tccaacctgc tgcgcgctcc tgaagcacag   1680

cagcacctgc tgaagctgac cgtgtggggc atcaaacagc tgcaggctag ggtgctggca   1740

gtcgagcggt acctgagaga ccagcagctg ctgggaatct ggggctgctc tgggaagctg   1800

atttgttgca caaatgtgcc ttggaactct agttggtcaa atcgcaacct gagcgagatc   1860

tgggacaata tgacttggct gcagtgggat aaagaaatta gtaactacac ccagatcatc   1920

tacggcctgc tggaagagtc acagaatcag caggagaaga acgaacagga cctgctggct   1980

ctggattg                                                            1988
```

```
<210> SEQ ID NO 19
<211> LENGTH: 625
<212> TYPE: PRT
<213> ORGANISM: Artificial sequence
<220> FEATURE:
<223> OTHER INFORMATION: Recombinant HIV-1 envelope protein

<400> SEQUENCE: 19

Ala Gly Leu Trp Val Thr Val Tyr Tyr Gly Val Pro Val Trp Arg Glu
1               5                   10                  15

Ala Lys Thr Thr Leu Phe Cys Ala Ser Asp Ala Lys Ser Tyr Glu Lys
            20                  25                  30

Glu Val His Asn Val Trp Ala Thr His Ala Cys Val Pro Thr Asp Pro
        35                  40                  45

Asn Pro Gln Glu Leu Val Leu Glu Asn Val Thr Glu Asn Phe Asn Met
    50                  55                  60

Trp Lys Asn Asp Met Val Asp Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Asn Cys Ser Asp Ala Lys Val Asn Ala Thr Tyr Lys Gly Thr
            100                 105                 110
```

-continued

```
Arg Glu Glu Ile Lys Asn Cys Ser Phe Asn Ala Thr Thr Glu Leu Arg
        115                 120                 125

Asp Lys Lys Arg Arg Glu Tyr Ala Leu Phe Tyr Arg Leu Asp Ile Val
    130                 135                 140

Pro Leu Ser Gly Glu Gly Asn Asn Asn Ser Glu Tyr Arg Leu Ile Asn
145                 150                 155                 160

Cys Asn Thr Ser Val Ile Thr Gln Ile Cys Pro Lys Val Thr Phe Asp
                165                 170                 175

Pro Ile Pro Ile His Tyr Cys Ala Pro Ala Gly Tyr Ala Ile Leu Lys
            180                 185                 190

Cys Asn Asn Lys Thr Phe Asn Gly Thr Gly Pro Cys Asn Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Glu Ile Ile Ile Arg Ser Glu
225                 230                 235                 240

Asn Leu Thr Asp Asn Val Lys Thr Ile Ile Val His Leu Asn Glu Ser
                245                 250                 255

Val Glu Ile Thr Cys Thr Arg Pro Asn Asn Met Thr Arg Lys Ser Val
            260                 265                 270

Arg Ile Gly Pro Gly Gln Thr Phe Tyr Ala Leu Gly Asp Ile Ile Gly
        275                 280                 285

Asp Ile Arg Gln Pro His Cys Asn Ile Ser Glu Ile Lys Trp Glu Lys
    290                 295                 300

Thr Leu Gln Arg Val Ser Glu Lys Leu Arg Glu His Phe Asn Lys Thr
305                 310                 315                 320

Ile Ile Phe Asn Gln Ser Ser Gly Gly Asp Leu Glu Ile Thr Thr His
                325                 330                 335

Ser Phe Asn Cys Gly Gly Glu Phe Phe Tyr Cys Asn Thr Ser Asp Leu
            340                 345                 350

Phe Phe Asn Lys Thr Phe Asn Glu Thr Tyr Ser Thr Gly Ser Asn Ser
        355                 360                 365

Thr Asn Ser Thr Ile Thr Leu Pro Cys Arg Ile Lys Gln Ile Ile Asn
    370                 375                 380

Met Trp Gln Glu Val Gly Arg Ala Met Tyr Ala Pro Pro Ile Ala Gly
385                 390                 395                 400

Asn Ile Thr Cys Lys Ser Asn Ile Thr Gly Leu Leu Leu Thr Arg Asp
                405                 410                 415

Gly Gly Gly Asn Asn Ser Thr Lys Glu Thr Phe Arg Pro Gly Gly Gly
            420                 425                 430

Asn Met Arg Asp Asn Trp Arg Ser Glu Leu Tyr Lys Tyr Lys Val Val
        435                 440                 445

Glu Val Lys Pro Leu Gly Ile Ala Pro Thr Glu Cys Asn Arg Thr Val
    450                 455                 460

Val Gln Arg Arg Arg Arg Arg Arg Ala Val Gly Leu Gly Ala Val Phe
465                 470                 475                 480

Leu Gly Phe Leu Gly Ala Ala Gly Ser Thr Met Gly Ala Ala Ser Asn
                485                 490                 495

Thr Leu Thr Val Gln Ala Arg Gln Leu Leu Ser Gly Ile Val Gln Gln
            500                 505                 510

Gln Ser Asn Leu Leu Arg Ala Pro Glu Ala Gln Gln His Met Leu Gln
        515                 520                 525

Leu Gly Val Trp Gly Phe Lys Gln Leu Gln Ala Arg Val Leu Ala Ile
```

```
    530                 535                 540

Glu Arg Tyr Leu Glu Val Gln Gln Leu Leu Gly Met Trp Gly Cys Ser
545                 550                 555                 560

Gly Lys Leu Ile Cys Cys Thr Asn Val Pro Trp Asn Ser Ser Trp Ser
                565                 570                 575

Asn Lys Thr Tyr Asn Glu Ile Trp Asp Asn Met Thr Trp Met Gln Trp
            580                 585                 590

Asp Arg Glu Ile Gly Asn Tyr Thr Asp Thr Ile Tyr Lys Leu Leu Glu
        595                 600                 605

Val Ser Gln Phe Gln Gln Glu Ile Asn Glu Lys Asp Asn Leu Thr Leu
    610                 615                 620

Asp
625


<210> SEQ ID NO 20
<211> LENGTH: 654
<212> TYPE: PRT
<213> ORGANISM: Artificial sequence
<220> FEATURE:
<223> OTHER INFORMATION: Recombinant HIV-1 envelope protein

<400> SEQUENCE: 20

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Gly Leu
            20                  25                  30

Trp Val Thr Val Tyr Tyr Gly Val Pro Val Trp Arg Glu Ala Lys Thr
        35                  40                  45

Thr Leu Phe Cys Ala Ser Asp Ala Lys Ser Tyr Glu Lys Glu Val His
    50                  55                  60

Asn Val Trp Ala Thr His Ala Cys Val Pro Thr Asp Pro Asn Pro Gln
65                  70                  75                  80

Glu Leu Val Leu Glu Asn Val Thr Glu Asn Phe Asn Met Trp Lys Asn
                85                  90                  95

Asp Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Ser Asp Ala Lys Val Asn Ala Thr Tyr Lys Gly Thr Arg Glu Glu
    130                 135                 140

Ile Lys Asn Cys Ser Phe Asn Ala Thr Thr Glu Leu Arg Asp Lys Lys
145                 150                 155                 160

Arg Arg Glu Tyr Ala Leu Phe Tyr Arg Leu Asp Ile Val Pro Leu Ser
                165                 170                 175

Gly Glu Gly Asn Asn Asn Ser Glu Tyr Arg Leu Ile Asn Cys Asn Thr
            180                 185                 190

Ser Val Ile Thr Gln Ile Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Ile Ile Ile Arg Ser Glu Asn Leu Thr
```

```
            260                 265                 270

Asp Asn Val Lys Thr Ile Ile Val His Leu Asn Glu Ser Val Glu Ile
        275                 280                 285

Thr Cys Thr Arg Pro Asn Asn Met Thr Arg Lys Ser Val Arg Ile Gly
    290                 295                 300

Pro Gly Gln Thr Phe Tyr Ala Leu Gly Asp Ile Ile Gly Asp Ile Arg
305                 310                 315                 320

Gln Pro His Cys Asn Ile Ser Glu Ile Lys Trp Glu Lys Thr Leu Gln
                325                 330                 335

Arg Val Ser Glu Lys Leu Arg Glu His Phe Asn Lys Thr Ile Ile Phe
            340                 345                 350

Asn Gln Ser Ser Gly Gly Asp Leu Glu Ile Thr Thr His Ser Phe Asn
        355                 360                 365

Cys Gly Gly Glu Phe Phe Tyr Cys Asn Thr Ser Asp Leu Phe Phe Asn
    370                 375                 380

Lys Thr Phe Asn Glu Thr Tyr Ser Thr Gly Ser Asn Ser Thr Asn Ser
385                 390                 395                 400

Thr Ile Thr Leu Pro Cys Arg Ile Lys Gln Ile Ile Asn Met Trp Gln
                405                 410                 415

Glu Val Gly Arg Ala Met Tyr Ala Pro Pro Ile Ala Gly Asn Ile Thr
            420                 425                 430

Cys Lys Ser Asn Ile Thr Gly Leu Leu Leu Thr Arg Asp Gly Gly Gly
        435                 440                 445

Asn Asn Ser Thr Lys Glu Thr Phe Arg Pro Gly Gly Gly Asn Met Arg
    450                 455                 460

Asp Asn Trp Arg Ser Glu Leu Tyr Lys Tyr Lys Val Val Glu Val Lys
465                 470                 475                 480

Pro Leu Gly Ile Ala Pro Thr Glu Cys Asn Arg Thr Val Val Gln Arg
                485                 490                 495

Arg Arg Arg Arg Arg Ala Val Gly Leu Gly Ala Val Phe Leu Gly Phe
            500                 505                 510

Leu Gly Ala Ala Gly Ser Thr Met Gly Ala Ala Ser Asn Thr Leu Thr
        515                 520                 525

Val Gln Ala Arg Gln Leu Leu Ser Gly Ile Val Gln Gln Gln Ser Asn
    530                 535                 540

Leu Leu Arg Ala Pro Glu Ala Gln Gln His Met Leu Gln Leu Gly Val
545                 550                 555                 560

Trp Gly Phe Lys Gln Leu Gln Ala Arg Val Leu Ala Ile Glu Arg Tyr
                565                 570                 575

Leu Glu Val Gln Gln Leu Leu Gly Met Trp Gly Cys Ser Gly Lys Leu
            580                 585                 590

Ile Cys Cys Thr Asn Val Pro Trp Asn Ser Ser Trp Ser Asn Lys Thr
        595                 600                 605

Tyr Asn Glu Ile Trp Asp Asn Met Thr Trp Met Gln Trp Asp Arg Glu
    610                 615                 620

Ile Gly Asn Tyr Thr Asp Thr Ile Tyr Lys Leu Leu Glu Val Ser Gln
625                 630                 635                 640

Phe Gln Gln Glu Ile Asn Glu Lys Asp Asn Leu Thr Leu Asp
                645                 650
```

<210> SEQ ID NO 21
<211> LENGTH: 617
<212> TYPE: PRT
<213> ORGANISM: Artificial sequence -continued
<220> FEATURE:
<223> OTHER INFORMATION: Recombinant HIV-1 envelope protein

<400> SEQUENCE: 21

```
Ala Asn Leu Trp Val Thr Val Tyr Tyr Gly Val Pro Val Trp Lys Glu
1               5                   10                  15

Ala Lys Thr Thr Leu Phe Cys Ala Ser Asp Ala Lys Ala Tyr Glu Lys
            20                  25                  30

Glu Val His Asn Val Trp Ala Thr His Ala Cys Val Pro Thr Asp Pro
        35                  40                  45

Asn Pro Gln Glu Met Val Leu Glu Asn Val Thr Glu Asn Phe Asn Met
    50                  55                  60

Trp Lys Asn Asp Met Val Asp Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Asn Cys Thr Asn Val Asn Val Thr Asn Thr Asn Asn Asn Asn
            100                 105                 110

Met Lys Glu Glu Met Lys Asn Cys Ser Phe Asn Thr Thr Thr Glu Ile
        115                 120                 125

Arg Asp Lys Lys Gln Lys Glu Tyr Ala Leu Phe Tyr Arg Leu Asp Ile
    130                 135                 140

Val Pro Leu Asn Glu Asn Ser Ser Glu Tyr Arg Leu Ile Asn Cys Asn
145                 150                 155                 160

Thr Ser Thr Ile Thr Gln Ile Cys Pro Lys Val Ser Phe Asp Pro Ile
                165                 170                 175

Pro Ile His Tyr Cys Ala Pro Ala Gly Tyr Ala Ile Leu Lys Cys Asn
            180                 185                 190

Asn Lys Thr Phe Asn Gly Thr Gly Pro Cys Asn Asn Val Ser Thr Val
        195                 200                 205

Gln Cys Thr His Gly Ile Lys Pro Val Val Ser Thr Gln Leu Leu Leu
    210                 215                 220

Asn Gly Ser Leu Ala Glu Glu Glu Ile Ile Ile Arg Ser Glu Asn Leu
225                 230                 235                 240

Thr Asp Asn Ala Lys Thr Ile Ile Val His Leu Asn Glu Ser Val Glu
                245                 250                 255

Ile Asn Cys Thr Arg Pro Asn Asn Met Thr Arg Lys Ser Ile Arg Ile
            260                 265                 270

Gly Pro Gly Gln Thr Phe Tyr Ala Leu Gly Asp Ile Ile Gly Asp Ile
        275                 280                 285

Arg Gln Pro His Cys Asn Ile Ser Glu Ala Lys Trp Asn Lys Thr Leu
    290                 295                 300

Gln Arg Val Lys Lys Lys Leu Lys Glu His Phe Pro Asn Lys Thr Ile
305                 310                 315                 320

Lys Phe Ala Pro Ser Ser Gly Gly Asp Leu Glu Ile Thr Thr His Ser
                325                 330                 335

Phe Asn Cys Arg Gly Glu Phe Phe Tyr Cys Asn Thr Ser Lys Leu Phe
            340                 345                 350

Asn Ser Thr Tyr Asn Asn Thr Thr Ser Asn Ser Thr Ile Thr Leu Pro
        355                 360                 365

Cys Arg Ile Lys Gln Ile Ile Asn Met Trp Gln Glu Val Gly Arg Ala
    370                 375                 380

Met Tyr Ala Pro Pro Ile Ala Gly Asn Ile Thr Cys Lys Ser Asn Ile
385                 390                 395                 400
```

```
Thr Gly Leu Leu Leu Thr Arg Asp Gly Gly Asn Asn Asn Asn Asn Thr
                405                 410                 415

Glu Thr Phe Arg Pro Gly Gly Gly Asp Met Arg Asp Asn Trp Arg Ser
            420                 425                 430

Glu Leu Tyr Lys Tyr Lys Val Val Glu Ile Lys Pro Leu Gly Ile Ala
        435                 440                 445

Pro Thr Lys Cys Lys Arg Arg Val Val Glu Arg Arg Arg Arg Arg Arg
    450                 455                 460

Ala Val Gly Leu Gly Ala Val Phe Leu Gly Phe Leu Gly Ala Ala Gly
465                 470                 475                 480

Ser Thr Met Gly Ala Ala Ser Asn Thr Leu Thr Val Gln Ala Arg Gln
                485                 490                 495

Leu Leu Ser Gly Ile Val Gln Gln Gln Ser Asn Leu Leu Arg Ala Pro
            500                 505                 510

Glu Ala Gln Gln His Met Leu Gln Leu Gly Val Trp Gly Phe Lys Gln
        515                 520                 525

Leu Gln Ala Arg Val Leu Ala Ile Glu Arg Tyr Leu Glu Val Gln Gln
    530                 535                 540

Leu Leu Gly Ile Trp Gly Cys Ser Gly Lys Leu Ile Cys Cys Thr Ala
545                 550                 555                 560

Val Pro Trp Asn Ser Ser Trp Ser Asn Lys Ser Gln Glu Asp Ile Trp
                565                 570                 575

Asp Asn Met Thr Trp Met Gln Trp Asp Arg Glu Ile Gly Asn Tyr Thr
            580                 585                 590

Asp Thr Ile Tyr Arg Leu Leu Glu Glu Ser Gln Phe Gln Gln Glu Ile
        595                 600                 605

Asn Glu Lys Asp Leu Leu Ala Leu Asp
    610                 615
```

<210> SEQ ID NO 22
<211> LENGTH: 646
<212> TYPE: PRT
<213> ORGANISM: Artificial sequence
<220> FEATURE:
<223> OTHER INFORMATION: Recombinant HIV-1 envelope protein

<400> SEQUENCE: 22

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Asn Leu
            20                  25                  30

Trp Val Thr Val Tyr Tyr Gly Val Pro Val Trp Lys Glu Ala Lys Thr
        35                  40                  45

Thr Leu Phe Cys Ala Ser Asp Ala Lys Ala Tyr Glu Lys Glu Val His
    50                  55                  60

Asn Val Trp Ala Thr His Ala Cys Val Pro Thr Asp Pro Asn Pro Gln
65                  70                  75                  80

Glu Met Val Leu Glu Asn Val Thr Glu Asn Phe Asn Met Trp Lys Asn
                85                  90                  95

Asp Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asn Val Asn Val Thr Asn Thr Asn Asn Asn Asn Met Lys Glu
    130                 135                 140
```

```
Glu Met Lys Asn Cys Ser Phe Asn Thr Thr Thr Glu Ile Arg Asp Lys
145                 150                 155                 160

Lys Gln Lys Glu Tyr Ala Leu Phe Tyr Arg Leu Asp Ile Val Pro Leu
                165                 170                 175

Asn Glu Asn Ser Ser Glu Tyr Arg Leu Ile Asn Cys Asn Thr Ser Thr
            180                 185                 190

Ile Thr Gln Ile Cys Pro Lys Val Ser Phe Asp Pro Ile Pro Ile His
        195                 200                 205

Tyr Cys Ala Pro Ala Gly Tyr Ala Ile Leu Lys Cys Asn Asn Lys Thr
    210                 215                 220

Phe Asn Gly Thr Gly Pro Cys Asn Asn Val Ser Thr Val Gln Cys Thr
225                 230                 235                 240

His Gly Ile Lys Pro Val Val Ser Thr Gln Leu Leu Leu Asn Gly Ser
                245                 250                 255

Leu Ala Glu Glu Glu Ile Ile Ile Arg Ser Glu Asn Leu Thr Asp Asn
            260                 265                 270

Ala Lys Thr Ile Ile Val His Leu Asn Glu Ser Val Glu Ile Asn Cys
        275                 280                 285

Thr Arg Pro Asn Asn Met Thr Arg Lys Ser Ile Arg Ile Gly Pro Gly
    290                 295                 300

Gln Thr Phe Tyr Ala Leu Gly Asp Ile Ile Gly Asp Ile Arg Gln Pro
305                 310                 315                 320

His Cys Asn Ile Ser Glu Ala Lys Trp Asn Lys Thr Leu Gln Arg Val
                325                 330                 335

Lys Lys Lys Leu Lys Glu His Phe Pro Asn Lys Thr Ile Lys Phe Ala
            340                 345                 350

Pro Ser Ser Gly Gly Asp Leu Glu Ile Thr Thr His Ser Phe Asn Cys
        355                 360                 365

Arg Gly Glu Phe Phe Tyr Cys Asn Thr Ser Lys Leu Phe Asn Ser Thr
    370                 375                 380

Tyr Asn Asn Thr Thr Ser Asn Ser Thr Ile Thr Leu Pro Cys Arg Ile
385                 390                 395                 400

Lys Gln Ile Ile Asn Met Trp Gln Glu Val Gly Arg Ala Met Tyr Ala
                405                 410                 415

Pro Pro Ile Ala Gly Asn Ile Thr Cys Lys Ser Asn Ile Thr Gly Leu
            420                 425                 430

Leu Leu Thr Arg Asp Gly Gly Asn Asn Asn Asn Asn Thr Glu Thr Phe
        435                 440                 445

Arg Pro Gly Gly Gly Asp Met Arg Asp Asn Trp Arg Ser Glu Leu Tyr
    450                 455                 460

Lys Tyr Lys Val Val Glu Ile Lys Pro Leu Gly Ile Ala Pro Thr Lys
465                 470                 475                 480

Cys Lys Arg Arg Val Val Glu Arg Arg Arg Arg Arg Arg Ala Val Gly
                485                 490                 495

Leu Gly Ala Val Phe Leu Gly Phe Leu Gly Ala Ala Gly Ser Thr Met
            500                 505                 510

Gly Ala Ala Ser Asn Thr Leu Thr Val Gln Ala Arg Gln Leu Leu Ser
        515                 520                 525

Gly Ile Val Gln Gln Gln Ser Asn Leu Leu Arg Ala Pro Glu Ala Gln
    530                 535                 540

Gln His Met Leu Gln Leu Gly Val Trp Gly Phe Lys Gln Leu Gln Ala
545                 550                 555                 560
```

```
Arg Val Leu Ala Ile Glu Arg Tyr Leu Glu Val Gln Gln Leu Leu Gly
                565                 570                 575

Ile Trp Gly Cys Ser Gly Lys Leu Ile Cys Cys Thr Ala Val Pro Trp
            580                 585                 590

Asn Ser Ser Trp Ser Asn Lys Ser Gln Glu Asp Ile Trp Asp Asn Met
        595                 600                 605

Thr Trp Met Gln Trp Asp Arg Glu Ile Gly Asn Tyr Thr Asp Thr Ile
    610                 615                 620

Tyr Arg Leu Leu Glu Glu Ser Gln Phe Gln Gln Glu Ile Asn Glu Lys
625                 630                 635                 640

Asp Leu Leu Ala Leu Asp
                645
```

<210> SEQ ID NO 23
<211> LENGTH: 625
<212> TYPE: PRT
<213> ORGANISM: Artificial sequence
<220> FEATURE:
<223> OTHER INFORMATION: Recombinant HIV-1 envelope protein

<400> SEQUENCE: 23

```
Ala Gly Leu Trp Val Thr Val Tyr Tyr Gly Val Pro Val Trp Arg Glu
1               5                   10                  15

Ala Lys Thr Thr Leu Phe Cys Ala Ser Asp Ala Lys Ser Tyr Glu Lys
            20                  25                  30

Glu Val His Asn Val Trp Ala Thr His Ala Cys Val Pro Thr Asp Pro
        35                  40                  45

Asn Pro Gln Glu Leu Val Leu Glu Asn Val Thr Glu Asn Phe Asn Met
    50                  55                  60

Trp Lys Asn Asp Met Val Asp Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Asn Cys Ser Asp Ala Lys Val Asn Ala Thr Tyr Lys Gly Thr
            100                 105                 110

Arg Glu Glu Ile Lys Asn Cys Ser Phe Asn Ala Thr Thr Glu Leu Arg
        115                 120                 125

Asp Lys Lys Arg Arg Glu Tyr Ala Leu Phe Tyr Arg Leu Asp Ile Val
    130                 135                 140

Pro Leu Ser Gly Glu Gly Asn Asn Asn Ser Glu Tyr Arg Leu Ile Asn
145                 150                 155                 160

Cys Asn Thr Ser Val Cys Thr Gln Ile Cys Pro Lys Val Thr Phe Asp
                165                 170                 175

Pro Ile Pro Ile His Tyr Cys Ala Pro Ala Gly Tyr Ala Ile Leu Lys
            180                 185                 190

Cys Asn Asn Lys Thr Phe Asn Gly Thr Gly Pro Cys Asn Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Glu Ile Ile Ile Arg Ser Glu
225                 230                 235                 240

Asn Leu Thr Asp Asn Val Lys Thr Ile Ile Val His Leu Asn Glu Ser
                245                 250                 255

Val Glu Ile Thr Cys Thr Arg Pro Asn Asn Met Thr Arg Lys Ser Val
            260                 265                 270
```

-continued

```
Arg Ile Gly Pro Gly Gln Thr Phe Tyr Ala Leu Gly Asp Ile Ile Gly
        275                 280                 285

Asp Ile Arg Gln Pro His Cys Asn Ile Ser Glu Ile Lys Trp Glu Lys
    290                 295                 300

Thr Leu Gln Arg Val Ser Glu Lys Leu Arg Glu His Phe Asn Lys Thr
305                 310                 315                 320

Ile Ile Phe Asn Gln Ser Ser Gly Gly Asp Leu Glu Ile Thr Thr His
                325                 330                 335

Ser Phe Asn Cys Gly Gly Glu Phe Phe Tyr Cys Asn Thr Ser Asp Leu
            340                 345                 350

Phe Phe Asn Lys Thr Phe Asn Glu Thr Tyr Ser Thr Gly Ser Asn Ser
        355                 360                 365

Thr Asn Ser Thr Ile Thr Leu Pro Cys Arg Ile Lys Gln Ile Ile Asn
    370                 375                 380

Met Trp Gln Glu Val Gly Arg Cys Met Tyr Ala Pro Pro Ile Ala Gly
385                 390                 395                 400

Asn Ile Thr Cys Lys Ser Asn Ile Thr Gly Leu Leu Leu Thr Arg Asp
                405                 410                 415

Gly Gly Gly Asn Asn Ser Thr Lys Glu Thr Phe Arg Pro Gly Gly Gly
            420                 425                 430

Asn Met Arg Asp Asn Trp Arg Ser Glu Leu Tyr Lys Tyr Lys Val Val
        435                 440                 445

Glu Val Lys Pro Leu Gly Ile Ala Pro Thr Glu Cys Asn Arg Thr Val
    450                 455                 460

Val Gln Arg Arg Arg Arg Arg Arg Ala Val Gly Leu Gly Ala Val Phe
465                 470                 475                 480

Leu Gly Phe Leu Gly Ala Ala Gly Ser Thr Met Gly Ala Ala Ser Asn
                485                 490                 495

Thr Leu Thr Val Gln Ala Arg Gln Leu Leu Ser Gly Ile Val Gln Gln
            500                 505                 510

Gln Ser Asn Leu Leu Arg Ala Pro Glu Ala Gln Gln His Met Leu Gln
        515                 520                 525

Leu Gly Val Trp Gly Phe Lys Gln Leu Gln Ala Arg Val Leu Ala Ile
    530                 535                 540

Glu Arg Tyr Leu Glu Val Gln Gln Leu Leu Gly Met Trp Gly Cys Ser
545                 550                 555                 560

Gly Lys Leu Ile Cys Cys Thr Asn Val Pro Trp Asn Ser Ser Trp Ser
                565                 570                 575

Asn Lys Thr Tyr Asn Glu Ile Trp Asp Asn Met Thr Trp Met Gln Trp
            580                 585                 590

Asp Arg Glu Ile Gly Asn Tyr Thr Asp Thr Ile Tyr Lys Leu Leu Glu
        595                 600                 605

Val Ser Gln Phe Gln Gln Glu Ile Asn Glu Lys Asp Asn Leu Thr Leu
    610                 615                 620

Asp
625


<210> SEQ ID NO 24
<211> LENGTH: 617
<212> TYPE: PRT
<213> ORGANISM: Artificial sequence
<220> FEATURE:
<223> OTHER INFORMATION: Recombinant HIV-1 envelope protein

<400> SEQUENCE: 24
```

-continued

```
Ala Asn Leu Trp Val Thr Val Tyr Tyr Gly Val Pro Val Trp Lys Glu
1               5                   10                  15

Ala Lys Thr Thr Leu Phe Cys Ala Ser Asp Ala Lys Ala Tyr Glu Lys
            20                  25                  30

Glu Val His Asn Val Trp Ala Thr His Ala Cys Val Pro Thr Asp Pro
        35                  40                  45

Asn Pro Gln Glu Met Val Leu Glu Asn Val Thr Glu Asn Phe Asn Met
    50                  55                  60

Trp Lys Asn Asp Met Val Asp Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Asn Cys Thr Asn Val Asn Val Thr Asn Thr Asn Asn Asn Asn
            100                 105                 110

Met Lys Glu Glu Met Lys Asn Cys Ser Phe Asn Thr Thr Thr Glu Ile
        115                 120                 125

Arg Asp Lys Lys Gln Lys Glu Tyr Ala Leu Phe Tyr Arg Leu Asp Ile
    130                 135                 140

Val Pro Leu Asn Glu Asn Ser Ser Glu Tyr Arg Leu Ile Asn Cys Asn
145                 150                 155                 160

Thr Ser Thr Cys Thr Gln Ile Cys Pro Lys Val Ser Phe Asp Pro Ile
                165                 170                 175

Pro Ile His Tyr Cys Ala Pro Ala Gly Tyr Ala Ile Leu Lys Cys Asn
            180                 185                 190

Asn Lys Thr Phe Asn Gly Thr Gly Pro Cys Asn Asn Val Ser Thr Val
        195                 200                 205

Gln Cys Thr His Gly Ile Lys Pro Val Val Ser Thr Gln Leu Leu Leu
    210                 215                 220

Asn Gly Ser Leu Ala Glu Glu Glu Ile Ile Ile Arg Ser Glu Asn Leu
225                 230                 235                 240

Thr Asp Asn Ala Lys Thr Ile Ile Val His Leu Asn Glu Ser Val Glu
                245                 250                 255

Ile Asn Cys Thr Arg Pro Asn Asn Met Thr Arg Lys Ser Ile Arg Ile
            260                 265                 270

Gly Pro Gly Gln Thr Phe Tyr Ala Leu Gly Asp Ile Ile Gly Asp Ile
        275                 280                 285

Arg Gln Pro His Cys Asn Ile Ser Glu Ala Lys Trp Asn Lys Thr Leu
    290                 295                 300

Gln Arg Val Lys Lys Lys Leu Lys Glu His Phe Pro Asn Lys Thr Ile
305                 310                 315                 320

Lys Phe Ala Pro Ser Ser Gly Gly Asp Leu Glu Ile Thr Thr His Ser
                325                 330                 335

Phe Asn Cys Arg Gly Glu Phe Phe Tyr Cys Asn Thr Ser Lys Leu Phe
            340                 345                 350

Asn Ser Thr Tyr Asn Asn Thr Thr Ser Asn Ser Thr Ile Thr Leu Pro
        355                 360                 365

Cys Arg Ile Lys Gln Ile Ile Asn Met Trp Gln Glu Val Gly Arg Cys
    370                 375                 380

Met Tyr Ala Pro Pro Ile Ala Gly Asn Ile Thr Cys Lys Ser Asn Ile
385                 390                 395                 400

Thr Gly Leu Leu Leu Thr Arg Asp Gly Gly Asn Asn Asn Asn Asn Thr
                405                 410                 415

Glu Thr Phe Arg Pro Gly Gly Gly Asp Met Arg Asp Asn Trp Arg Ser
```

```
            420                 425                 430

Glu Leu Tyr Lys Tyr Lys Val Val Glu Ile Lys Pro Leu Gly Ile Ala
        435                 440                 445

Pro Thr Lys Cys Lys Arg Arg Val Val Glu Arg Arg Arg Arg Arg Arg
    450                 455                 460

Ala Val Gly Leu Gly Ala Val Phe Leu Gly Phe Leu Gly Ala Ala Gly
465                 470                 475                 480

Ser Thr Met Gly Ala Ala Ser Asn Thr Leu Thr Val Gln Ala Arg Gln
                485                 490                 495

Leu Leu Ser Gly Ile Val Gln Gln Gln Ser Asn Leu Leu Arg Ala Pro
            500                 505                 510

Glu Ala Gln Gln His Met Leu Gln Leu Gly Val Trp Gly Phe Lys Gln
        515                 520                 525

Leu Gln Ala Arg Val Leu Ala Ile Glu Arg Tyr Leu Glu Val Gln Gln
    530                 535                 540

Leu Leu Gly Ile Trp Gly Cys Ser Gly Lys Leu Ile Cys Cys Thr Ala
545                 550                 555                 560

Val Pro Trp Asn Ser Ser Trp Ser Asn Lys Ser Gln Glu Asp Ile Trp
                565                 570                 575

Asp Asn Met Thr Trp Met Gln Trp Asp Arg Glu Ile Gly Asn Tyr Thr
            580                 585                 590

Asp Thr Ile Tyr Arg Leu Leu Glu Glu Ser Gln Phe Gln Gln Glu Ile
        595                 600                 605

Asn Glu Lys Asp Leu Leu Ala Leu Asp
    610                 615


<210> SEQ ID NO 25
<211> LENGTH: 654
<212> TYPE: PRT
<213> ORGANISM: Artificial sequence
<220> FEATURE:
<223> OTHER INFORMATION: Recombinant HIV-1 envelope protein

<400> SEQUENCE: 25

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Gly Leu
            20                  25                  30

Trp Val Thr Val Tyr Tyr Gly Val Pro Val Trp Arg Glu Ala Lys Thr
        35                  40                  45

Thr Leu Phe Cys Ala Ser Asp Ala Lys Ser Tyr Glu Lys Glu Val His
    50                  55                  60

Asn Val Trp Ala Thr His Ala Cys Val Pro Thr Asp Pro Asn Pro Gln
65                  70                  75                  80

Glu Leu Val Leu Glu Asn Val Thr Glu Asn Phe Asn Met Trp Lys Asn
                85                  90                  95

Asp Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Ser Asp Ala Lys Val Asn Ala Thr Tyr Lys Gly Thr Arg Glu Glu
    130                 135                 140

Ile Lys Asn Cys Ser Phe Asn Ala Thr Thr Glu Leu Arg Asp Lys Lys
145                 150                 155                 160

Arg Arg Glu Tyr Ala Leu Phe Tyr Arg Leu Asp Ile Val Pro Leu Ser
```

-continued

```
                165                 170                 175

Gly Glu Gly Asn Asn Asn Ser Glu Tyr Arg Leu Ile Asn Cys Asn Thr
            180                 185                 190

Ser Val Cys Thr Gln Ile Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Ile Ile Ile Arg Ser Glu Asn Leu Thr
            260                 265                 270

Asp Asn Val Lys Thr Ile Ile Val His Leu Asn Glu Ser Val Glu Ile
        275                 280                 285

Thr Cys Thr Arg Pro Asn Asn Met Thr Arg Lys Ser Val Arg Ile Gly
    290                 295                 300

Pro Gly Gln Thr Phe Tyr Ala Leu Gly Asp Ile Ile Gly Asp Ile Arg
305                 310                 315                 320

Gln Pro His Cys Asn Ile Ser Glu Ile Lys Trp Glu Lys Thr Leu Gln
                325                 330                 335

Arg Val Ser Glu Lys Leu Arg Glu His Phe Asn Lys Thr Ile Ile Phe
            340                 345                 350

Asn Gln Ser Ser Gly Gly Asp Leu Glu Ile Thr Thr His Ser Phe Asn
        355                 360                 365

Cys Gly Gly Glu Phe Phe Tyr Cys Asn Thr Ser Asp Leu Phe Phe Asn
    370                 375                 380

Lys Thr Phe Asn Glu Thr Tyr Ser Thr Gly Ser Asn Ser Thr Asn Ser
385                 390                 395                 400

Thr Ile Thr Leu Pro Cys Arg Ile Lys Gln Ile Ile Asn Met Trp Gln
                405                 410                 415

Glu Val Gly Arg Cys Met Tyr Ala Pro Pro Ile Ala Gly Asn Ile Thr
            420                 425                 430

Cys Lys Ser Asn Ile Thr Gly Leu Leu Leu Thr Arg Asp Gly Gly Gly
        435                 440                 445

Asn Asn Ser Thr Lys Glu Thr Phe Arg Pro Gly Gly Gly Asn Met Arg
    450                 455                 460

Asp Asn Trp Arg Ser Glu Leu Tyr Lys Tyr Lys Val Val Glu Val Lys
465                 470                 475                 480

Pro Leu Gly Ile Ala Pro Thr Glu Cys Asn Arg Thr Val Val Gln Arg
                485                 490                 495

Arg Arg Arg Arg Arg Ala Val Gly Leu Gly Ala Val Phe Leu Gly Phe
            500                 505                 510

Leu Gly Ala Ala Gly Ser Thr Met Gly Ala Ala Ser Asn Thr Leu Thr
        515                 520                 525

Val Gln Ala Arg Gln Leu Leu Ser Gly Ile Val Gln Gln Gln Ser Asn
    530                 535                 540

Leu Leu Arg Ala Pro Glu Ala Gln Gln His Met Leu Gln Leu Gly Val
545                 550                 555                 560

Trp Gly Phe Lys Gln Leu Gln Ala Arg Val Leu Ala Ile Glu Arg Tyr
                565                 570                 575

Leu Glu Val Gln Gln Leu Leu Gly Met Trp Gly Cys Ser Gly Lys Leu
            580                 585                 590
```

```
Ile Cys Cys Thr Asn Val Pro Trp Asn Ser Ser Trp Ser Asn Lys Thr
        595                 600                 605

Tyr Asn Glu Ile Trp Asp Asn Met Thr Trp Met Gln Trp Asp Arg Glu
    610                 615                 620

Ile Gly Asn Tyr Thr Asp Thr Ile Tyr Lys Leu Leu Glu Val Ser Gln
625                 630                 635                 640

Phe Gln Gln Glu Ile Asn Glu Lys Asp Asn Leu Thr Leu Asp
                645                 650


<210> SEQ ID NO 26
<211> LENGTH: 646
<212> TYPE: PRT
<213> ORGANISM: Artificial sequence
<220> FEATURE:
<223> OTHER INFORMATION: Recombinant HIV-1 envelope protein

<400> SEQUENCE: 26

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Asn Leu
            20                  25                  30

Trp Val Thr Val Tyr Tyr Gly Val Pro Val Trp Lys Glu Ala Lys Thr
        35                  40                  45

Thr Leu Phe Cys Ala Ser Asp Ala Lys Ala Tyr Glu Lys Glu Val His
    50                  55                  60

Asn Val Trp Ala Thr His Ala Cys Val Pro Thr Asp Pro Asn Pro Gln
65                  70                  75                  80

Glu Met Val Leu Glu Asn Val Thr Glu Asn Phe Asn Met Trp Lys Asn
                85                  90                  95

Asp Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asn Val Asn Val Thr Asn Thr Asn Asn Asn Asn Met Lys Glu
    130                 135                 140

Glu Met Lys Asn Cys Ser Phe Asn Thr Thr Thr Glu Ile Arg Asp Lys
145                 150                 155                 160

Lys Gln Lys Glu Tyr Ala Leu Phe Tyr Arg Leu Asp Ile Val Pro Leu
                165                 170                 175

Asn Glu Asn Ser Ser Glu Tyr Arg Leu Ile Asn Cys Asn Thr Ser Thr
            180                 185                 190

Cys Thr Gln Ile Cys Pro Lys Val Ser Phe Asp Pro Ile Pro Ile His
        195                 200                 205

Tyr Cys Ala Pro Ala Gly Tyr Ala Ile Leu Lys Cys Asn Asn Lys Thr
    210                 215                 220

Phe Asn Gly Thr Gly Pro Cys Asn Asn Val Ser Thr Val Gln Cys Thr
225                 230                 235                 240

His Gly Ile Lys Pro Val Val Ser Thr Gln Leu Leu Leu Asn Gly Ser
                245                 250                 255

Leu Ala Glu Glu Glu Ile Ile Ile Arg Ser Glu Asn Leu Thr Asp Asn
            260                 265                 270

Ala Lys Thr Ile Ile Val His Leu Asn Glu Ser Val Glu Ile Asn Cys
        275                 280                 285

Thr Arg Pro Asn Asn Met Thr Arg Lys Ser Ile Arg Ile Gly Pro Gly
    290                 295                 300
```

Gln Thr Phe Tyr Ala Leu Gly Asp Ile Ile Gly Asp Ile Arg Gln Pro
305 310 315 320

His Cys Asn Ile Ser Glu Ala Lys Trp Asn Lys Thr Leu Gln Arg Val
325 330 335

Lys Lys Lys Leu Lys Glu His Phe Pro Asn Lys Thr Ile Lys Phe Ala
340 345 350

Pro Ser Ser Gly Gly Asp Leu Glu Ile Thr Thr His Ser Phe Asn Cys
355 360 365

Arg Gly Glu Phe Phe Tyr Cys Asn Thr Ser Lys Leu Phe Asn Ser Thr
370 375 380

Tyr Asn Asn Thr Thr Ser Asn Ser Thr Ile Thr Leu Pro Cys Arg Ile
385 390 395 400

Lys Gln Ile Ile Asn Met Trp Gln Glu Val Gly Arg Cys Met Tyr Ala
405 410 415

Pro Pro Ile Ala Gly Asn Ile Thr Cys Lys Ser Asn Ile Thr Gly Leu
420 425 430

Leu Leu Thr Arg Asp Gly Gly Asn Asn Asn Asn Asn Thr Glu Thr Phe
435 440 445

Arg Pro Gly Gly Gly Asp Met Arg Asp Asn Trp Arg Ser Glu Leu Tyr
450 455 460

Lys Tyr Lys Val Val Glu Ile Lys Pro Leu Gly Ile Ala Pro Thr Lys
465 470 475 480

Cys Lys Arg Arg Val Val Glu Arg Arg Arg Arg Arg Arg Ala Val Gly
485 490 495

Leu Gly Ala Val Phe Leu Gly Phe Leu Gly Ala Ala Gly Ser Thr Met
500 505 510

Gly Ala Ala Ser Asn Thr Leu Thr Val Gln Ala Arg Gln Leu Leu Ser
515 520 525

Gly Ile Val Gln Gln Gln Ser Asn Leu Leu Arg Ala Pro Glu Ala Gln
530 535 540

Gln His Met Leu Gln Leu Gly Val Trp Gly Phe Lys Gln Leu Gln Ala
545 550 555 560

Arg Val Leu Ala Ile Glu Arg Tyr Leu Glu Val Gln Gln Leu Leu Gly
565 570 575

Ile Trp Gly Cys Ser Gly Lys Leu Ile Cys Cys Thr Ala Val Pro Trp
580 585 590

Asn Ser Ser Trp Ser Asn Lys Ser Gln Glu Asp Ile Trp Asp Asn Met
595 600 605

Thr Trp Met Gln Trp Asp Arg Glu Ile Gly Asn Tyr Thr Asp Thr Ile
610 615 620

Tyr Arg Leu Leu Glu Glu Ser Gln Phe Gln Gln Glu Ile Asn Glu Lys
625 630 635 640

Asp Leu Leu Ala Leu Asp
645

<210> SEQ ID NO 27
<211> LENGTH: 7
<212> TYPE: PRT
<213> ORGANISM: Artificial sequence
<220> FEATURE:
<223> OTHER INFORMATION: Recombinant furin cleavage site

<400> SEQUENCE: 27

Gly Arg Arg Arg Arg Arg Arg
1 5

<210> SEQ ID NO 28
<211> LENGTH: 10
<212> TYPE: PRT
<213> ORGANISM: Artificial sequence
<220> FEATURE:
<223> OTHER INFORMATION: Recombinant furin cleavage site

<400> SEQUENCE: 28

Gly Gly Ser Gly Arg Arg Arg Arg Arg Arg
1               5                   10

<210> SEQ ID NO 29
<211> LENGTH: 10
<212> TYPE: PRT
<213> ORGANISM: Artificial sequence
<220> FEATURE:
<223> OTHER INFORMATION: Recombinant furin cleavage site

<400> SEQUENCE: 29

Gly Arg Arg Arg Arg Arg Arg Arg Arg Arg
1               5                   10

<210> SEQ ID NO 30
<211> LENGTH: 18
<212> TYPE: PRT
<213> ORGANISM: Artificial sequence
<220> FEATURE:
<223> OTHER INFORMATION: Recombinant furin cleavage site

<400> SEQUENCE: 30

Gly Asn Ser Thr His Lys Gln Leu Thr His His Met Arg Arg Arg Arg
1               5                   10                  15

Arg Arg

<210> SEQ ID NO 31
<211> LENGTH: 625
<212> TYPE: PRT
<213> ORGANISM: Artificial sequence
<220> FEATURE:
<223> OTHER INFORMATION: Recombinant HIV-1 Env sequence

<400> SEQUENCE: 31

Ala Val Glu Lys Leu Trp Val Thr Val Tyr Tyr Gly Val Pro Val Trp
1               5                   10                  15

Lys Asp Ala Lys Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Met Leu Leu Asp Asn Val Thr Glu Asn Phe
    50                  55                  60

Asn Met Trp Lys Asn Asp Met Val Asp Gln Met His Glu Asp Val Ile
65                  70                  75                  80

Ser Leu Trp Asp Gln Ser Leu Lys Pro Cys Val Lys Leu Thr Pro Leu
                85                  90                  95

Cys Val Thr Leu Glu Cys Thr Asp Ser Ser Asn Gln Thr His Tyr Asn
            100                 105                 110

Glu Ser Met Gln Glu Ile Lys Asn Cys Thr Phe Asn Val Thr Thr Glu
        115                 120                 125

Ile Arg Asp Arg Lys Gln Arg Val Gln Ala Leu Phe Tyr Lys Leu Asp
    130                 135                 140

```
Ile Val Ser Leu Glu Lys Asn Ser Ser Thr Tyr Arg Leu Ile Asn Cys
145                 150                 155                 160

Asn Thr Ser Ala Cys Thr Gln Ala Cys Pro Lys Val Thr Phe Asp Pro
                165                 170                 175

Ile Pro Ile His Tyr Cys Thr Pro Ala Gly Tyr Ala Ile Leu Lys Cys
            180                 185                 190

Asn Asn Glu Thr Phe Asn Gly Thr Gly Pro Cys Arg Asn Val Ser Thr
        195                 200                 205

Val Gln Cys Thr His Gly Ile Lys Pro Val Val Ser Thr Gln Leu Leu
    210                 215                 220

Leu Asn Gly Ser Leu Ala Glu Lys Asp Ile Met Ile Arg Ser Glu Asn
225                 230                 235                 240

Leu Thr Asp Asn Ala Lys Thr Ile Ile Val His Leu Asn Gln Thr Val
                245                 250                 255

Glu Ile Val Cys Ile Arg Pro Asn Asn Met Thr Arg Gln Ser Ile Arg
            260                 265                 270

Ile Gly Pro Gly Gln Val Phe Tyr Ala Leu Gly Asp Ile Ile Gly Asp
        275                 280                 285

Ile Arg Gln Pro Tyr Cys Thr Ile Asn Thr Thr Ala Trp Asn Glu Thr
    290                 295                 300

Leu Gln Arg Val Ser Lys Lys Leu Ala Glu His Phe Pro Asn Lys Thr
305                 310                 315                 320

Ile Arg Phe Ala Pro Ser Ser Gly Gly Asp Leu Glu Ile Thr Thr His
                325                 330                 335

Ser Phe Asn Cys Arg Gly Glu Phe Phe Tyr Cys Asn Thr Ser Gly Leu
            340                 345                 350

Phe Asn Ser Thr Tyr Met Thr Asn Gly Thr Phe Thr Tyr Lys Leu Asn
        355                 360                 365

Asp Thr Asn Ile Thr Ile Pro Cys Arg Ile Lys Gln Ile Ile Asn Met
    370                 375                 380

Trp Gln Glu Val Gly Arg Cys Met Tyr Ala Pro Pro Ile Ala Gly Asn
385                 390                 395                 400

Ile Thr Cys Lys Ser Asn Ile Thr Gly Met Leu Leu Val Arg Asp Gly
                405                 410                 415

Gly Lys Asn Glu Asn Ser Thr Glu Glu Thr Phe Arg Pro Gly Gly Gly
            420                 425                 430

Asn Met Arg Asp Asn Trp Arg Ser Glu Leu Tyr Lys Tyr Lys Val Val
        435                 440                 445

Glu Ile Lys Pro Leu Gly Val Ala Pro Thr Lys Cys Lys Arg Arg Val
    450                 455                 460

Val Gly Arg Arg Arg Arg Arg Arg Ala Val Gly Ile Gly Ala Val Phe
465                 470                 475                 480

Leu Gly Phe Leu Gly Ala Ala Gly Ser Thr Met Gly Ala Ala Ser Met
                485                 490                 495

Thr Leu Thr Val Gln Ala Arg Asn Leu Leu Ser Gly Ile Val Gln Gln
            500                 505                 510

Gln Ser Asn Leu Leu Arg Ala Pro Glu Ala Gln Gln His Leu Leu Lys
        515                 520                 525

Leu Thr Val Trp Gly Ile Lys Gln Leu Gln Ala Arg Val Leu Ala Val
    530                 535                 540

Glu Arg Tyr Leu Arg Asp Gln Gln Leu Leu Gly Ile Trp Gly Cys Ser
545                 550                 555                 560

Gly Lys Leu Ile Cys Cys Thr Asn Val Pro Trp Asn Ser Ser Trp Ser
```

```
                565                 570                 575

Asn Arg Asn Leu Ser Glu Ile Trp Asp Asn Met Thr Trp Leu Gln Trp
            580                 585                 590

Asp Lys Glu Ile Ser Asn Tyr Thr Gln Ile Ile Tyr Gly Leu Leu Glu
        595                 600                 605

Glu Ser Gln Asn Gln Gln Glu Lys Asn Glu Gln Asp Leu Leu Ala Leu
    610                 615                 620

Asp
625


<210> SEQ ID NO 32
<211> LENGTH: 645
<212> TYPE: PRT
<213> ORGANISM: Artificial sequence
<220> FEATURE:
<223> OTHER INFORMATION: Recombinant HIV-1 Env sequence

<400> SEQUENCE: 32

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Cys Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Met
            260                 265                 270

Thr Arg Lys Ser Ile Arg Ile Gly Pro Gly Gln Ala Phe Tyr Ala Leu
        275                 280                 285

Gly Asp Ile Ile Gly Asp Ile Arg Gln Pro His Cys Asn Val Ser Lys
```

```
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Cys Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Asn Ser Thr His Lys
465                 470                 475                 480

Gln Leu Thr His His Met Arg Arg Arg Arg Arg Arg Ala Val Gly Ile
                485                 490                 495

Gly Ala Val Phe Leu Gly Phe Leu Gly Ala Ala Gly Ser Thr Met Gly
            500                 505                 510

Ala Ala Ser Met Thr Leu Thr Val Gln Ala Arg Asn Leu Leu Ser Gly
        515                 520                 525

Ile Val Gln Gln Gln Ser Asn Leu Leu Arg Ala Pro Glu Ala Gln Gln
    530                 535                 540

His Leu Leu Lys Leu Thr Val Trp Gly Ile Lys Gln Leu Gln Ala Arg
545                 550                 555                 560

Val Leu Ala Val Glu Arg Tyr Leu Arg Asp Gln Gln Leu Leu Gly Ile
                565                 570                 575

Trp Gly Cys Ser Gly Lys Leu Ile Cys Cys Thr Asn Val Pro Trp Asn
            580                 585                 590

Ser Ser Trp Ser Asn Arg Asn Leu Ser Glu Ile Trp Asp Asn Met Thr
        595                 600                 605

Trp Leu Gln Trp Asp Lys Glu Ile Ser Asn Tyr Thr Gln Ile Ile Tyr
    610                 615                 620

Gly Leu Leu Glu Glu Ser Gln Asn Gln Gln Glu Lys Asn Glu Gln Asp
625                 630                 635                 640

Leu Leu Ala Leu Asp
                645


<210> SEQ ID NO 33
<211> LENGTH: 625
<212> TYPE: PRT
<213> ORGANISM: Artificial Sequence
<220> FEATURE:
<223> OTHER INFORMATION: Recombinant HIV-1 Env sequence

<400> SEQUENCE: 33

Ala Val Glu Lys Leu Trp Val Thr Val Tyr Tyr Gly Val Pro Val Trp
```

-continued

```
1               5                   10                  15

Lys Asp Ala Lys Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Met Leu Leu Asp Asn Val Thr Glu Asn Phe
    50                  55                  60

Asn Met Trp Lys Asn Asp Met Val Asp Gln Met His Glu Asp Val Ile
65                  70                  75                  80

Ser Leu Trp Asp Gln Ser Leu Lys Pro Cys Val Lys Leu Thr Pro Leu
                85                  90                  95

Cys Val Thr Leu Glu Cys Thr Asp Ser Ser Asn Gln Thr His Tyr Asn
            100                 105                 110

Glu Ser Met Gln Glu Ile Lys Asn Cys Thr Phe Asn Val Thr Thr Glu
        115                 120                 125

Ile Arg Asp Arg Lys Gln Arg Val Gln Ala Leu Phe Tyr Lys Leu Asp
    130                 135                 140

Ile Val Ser Leu Glu Lys Asn Ser Ser Thr Tyr Arg Leu Ile Asn Cys
145                 150                 155                 160

Asn Thr Ser Ala Cys Thr Gln Ala Cys Pro Lys Val Thr Phe Asp Pro
                165                 170                 175

Ile Pro Ile His Tyr Cys Thr Pro Ala Gly Tyr Ala Ile Leu Lys Cys
            180                 185                 190

Asn Asn Glu Thr Phe Asn Gly Thr Gly Pro Cys Arg Asn Val Ser Thr
        195                 200                 205

Val Gln Cys Thr His Gly Ile Lys Pro Val Val Ser Thr Gln Leu Leu
    210                 215                 220

Leu Asn Gly Ser Leu Ala Glu Lys Asp Ile Met Ile Arg Ser Glu Asn
225                 230                 235                 240

Leu Thr Asp Asn Ala Lys Thr Ile Ile Val His Leu Asn Gln Thr Val
                245                 250                 255

Glu Ile Val Cys Ile Arg Pro Asn Asn Asn Thr Arg Gln Ser Ile Arg
            260                 265                 270

Ile Gly Pro Gly Gln Val Phe Tyr Ala Thr Gly Asp Ile Ile Gly Asp
        275                 280                 285

Ile Arg Gln Ala Tyr Cys Thr Ile Asn Thr Thr Ala Trp Asn Glu Thr
    290                 295                 300

Leu Gln Arg Val Ser Lys Lys Leu Ala Glu His Phe Pro Asn Lys Thr
305                 310                 315                 320

Ile Arg Phe Ala Pro Ser Ser Gly Gly Asp Leu Glu Ile Thr Thr His
                325                 330                 335

Ser Phe Asn Cys Arg Gly Glu Phe Phe Tyr Cys Asn Thr Ser Gly Leu
            340                 345                 350

Phe Asn Ser Thr Tyr Met Thr Asn Gly Thr Phe Thr Tyr Lys Leu Asn
        355                 360                 365

Asp Thr Asn Ile Thr Ile Pro Cys Arg Ile Lys Gln Ile Ile Asn Met
    370                 375                 380

Trp Gln Glu Val Gly Arg Cys Met Tyr Ala Pro Pro Ile Ala Gly Asn
385                 390                 395                 400

Ile Thr Cys Lys Ser Asn Ile Thr Gly Met Leu Leu Val Arg Asp Gly
                405                 410                 415

Gly Lys Asn Glu Asn Ser Thr Glu Glu Thr Phe Arg Pro Gly Gly Gly
            420                 425                 430
```

```
Asn Met Arg Asp Asn Trp Arg Ser Glu Leu Tyr Lys Tyr Lys Val Val
        435                 440                 445

Glu Ile Lys Pro Leu Gly Val Ala Pro Thr Lys Cys Lys Arg Arg Val
    450                 455                 460

Val Gly Arg Arg Arg Arg Arg Arg Ala Val Gly Ile Gly Ala Val Phe
465                 470                 475                 480

Leu Gly Phe Leu Gly Ala Ala Gly Ser Thr Met Gly Ala Ala Ser Met
                485                 490                 495

Thr Leu Thr Val Gln Ala Arg Asn Leu Leu Ser Gly Ile Val Gln Gln
            500                 505                 510

Gln Ser Asn Leu Leu Arg Ala Pro Glu Ala Gln Gln His Leu Leu Lys
        515                 520                 525

Leu Thr Val Trp Gly Ile Lys Gln Leu Gln Ala Arg Val Leu Ala Val
    530                 535                 540

Glu Arg Tyr Leu Arg Asp Gln Gln Leu Leu Gly Ile Trp Gly Cys Ser
545                 550                 555                 560

Gly Lys Leu Ile Cys Cys Thr Asn Val Pro Trp Asn Ser Ser Trp Ser
                565                 570                 575

Asn Arg Asn Leu Ser Glu Ile Trp Asp Asn Met Thr Trp Leu Gln Trp
            580                 585                 590

Asp Lys Glu Ile Ser Asn Tyr Thr Gln Ile Ile Tyr Gly Leu Leu Glu
        595                 600                 605

Glu Ser Gln Asn Gln Gln Glu Lys Asn Glu Gln Asp Leu Leu Ala Leu
    610                 615                 620

Asp
625


<210> SEQ ID NO 34
<211> LENGTH: 645
<212> TYPE: PRT
<213> ORGANISM: Artificial Sequence
<220> FEATURE:
<223> OTHER INFORMATION: Recombinant HIV-1 Env sequence

<400> SEQUENCE: 34

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160
```

-continued

```
Tyr Arg Leu Ile Asn Cys Asn Thr Ser Ala Cys Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Cys Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Asn Ser Thr His Lys
465                 470                 475                 480

Gln Leu Thr His His Met Arg Arg Arg Arg Arg Arg Ala Val Gly Ile
                485                 490                 495

Gly Ala Val Phe Leu Gly Phe Leu Gly Ala Ala Gly Ser Thr Met Gly
            500                 505                 510

Ala Ala Ser Met Thr Leu Thr Val Gln Ala Arg Asn Leu Leu Ser Gly
        515                 520                 525

Ile Val Gln Gln Gln Ser Asn Leu Leu Arg Ala Pro Glu Ala Gln Gln
    530                 535                 540

His Leu Leu Lys Leu Thr Val Trp Gly Ile Lys Gln Leu Gln Ala Arg
545                 550                 555                 560

Val Leu Ala Val Glu Arg Tyr Leu Arg Asp Gln Gln Leu Leu Gly Ile
                565                 570                 575
```

```
Trp Gly Cys Ser Gly Lys Leu Ile Cys Cys Thr Asn Val Pro Trp Asn
            580                 585                 590

Ser Ser Trp Ser Asn Arg Asn Leu Ser Glu Ile Trp Asp Asn Met Thr
        595                 600                 605

Trp Leu Gln Trp Asp Lys Glu Ile Ser Asn Tyr Thr Gln Ile Ile Tyr
    610                 615                 620

Gly Leu Leu Glu Glu Ser Gln Asn Gln Gln Glu Lys Asn Glu Gln Asp
625                 630                 635                 640

Leu Leu Ala Leu Asp
                645


<210> SEQ ID NO 35
<211> LENGTH: 655
<212> TYPE: PRT
<213> ORGANISM: Artificial Sequence
<220> FEATURE:
<223> OTHER INFORMATION: Recombinant HIV-1 Env sequence

<400> SEQUENCE: 35

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ala Val
            20                  25                  30

Glu Lys Leu Trp Val Thr Val Tyr Tyr Gly Val Pro Val Trp Lys Asp
        35                  40                  45

Ala Lys Thr Thr Leu Phe Cys Ala Ser Asp Ala Lys Ala Tyr Asp Thr
    50                  55                  60

Glu Val His Asn Val Trp Ala Thr His Ala Cys Val Pro Thr Asp Pro
65                  70                  75                  80

Asn Pro Gln Glu Met Leu Leu Asp Asn Val Thr Glu Asn Phe Asn Met
                85                  90                  95

Trp Lys Asn Asp Met Val Asp Gln Met His Glu Asp Val Ile Ser Leu
            100                 105                 110

Trp Asp Gln Ser Leu Lys Pro Cys Val Lys Leu Thr Pro Leu Cys Val
        115                 120                 125

Thr Leu Glu Cys Thr Asp Ser Ser Asn Gln Thr His Tyr Asn Glu Ser
    130                 135                 140

Met Gln Glu Ile Lys Asn Cys Thr Phe Asn Val Thr Thr Glu Ile Arg
145                 150                 155                 160

Asp Arg Lys Gln Arg Val Gln Ala Leu Phe Tyr Lys Leu Asp Ile Val
                165                 170                 175

Ser Leu Glu Lys Asn Ser Ser Thr Tyr Arg Leu Ile Asn Cys Asn Thr
            180                 185                 190

Ser Ala Cys Thr Gln Ala Cys Pro Lys Val Thr Phe Asp Pro Ile Pro
        195                 200                 205

Ile His Tyr Cys Thr Pro Ala Gly Tyr Ala Ile Leu Lys Cys Asn Asn
    210                 215                 220

Glu Thr Phe Asn Gly Thr Gly Pro Cys Arg Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Lys Asp Ile Met Ile Arg Ser Glu Asn Leu Thr
            260                 265                 270

Asp Asn Ala Lys Thr Ile Ile Val His Leu Asn Gln Thr Val Glu Ile
        275                 280                 285
```

-continued

```
Val Cys Ile Arg Pro Asn Asn Met Thr Arg Gln Ser Ile Arg Ile Gly
    290                 295                 300

Pro Gly Gln Val Phe Tyr Ala Leu Gly Asp Ile Ile Gly Asp Ile Arg
305                 310                 315                 320

Gln Pro Tyr Cys Thr Ile Asn Thr Thr Ala Trp Asn Glu Thr Leu Gln
                325                 330                 335

Arg Val Ser Lys Lys Leu Ala Glu His Phe Pro Asn Lys Thr Ile Arg
            340                 345                 350

Phe Ala Pro Ser Ser Gly Gly Asp Leu Glu Ile Thr Thr His Ser Phe
        355                 360                 365

Asn Cys Arg Gly Glu Phe Phe Tyr Cys Asn Thr Ser Gly Leu Phe Asn
    370                 375                 380

Ser Thr Tyr Met Thr Asn Gly Thr Phe Thr Tyr Lys Leu Asn Asp Thr
385                 390                 395                 400

Asn Ile Thr Ile Pro Cys Arg Ile Lys Gln Ile Ile Asn Met Trp Gln
                405                 410                 415

Glu Val Gly Arg Cys Met Tyr Ala Pro Pro Ile Ala Gly Asn Ile Thr
            420                 425                 430

Cys Lys Ser Asn Ile Thr Gly Met Leu Leu Val Arg Asp Gly Gly Lys
        435                 440                 445

Asn Glu Asn Ser Thr Glu Glu Thr Phe Arg Pro Gly Gly Gly Asn Met
    450                 455                 460

Arg Asp Asn Trp Arg Ser Glu Leu Tyr Lys Tyr Lys Val Val Glu Ile
465                 470                 475                 480

Lys Pro Leu Gly Val Ala Pro Thr Lys Cys Lys Arg Arg Val Val Gly
                485                 490                 495

Arg Arg Arg Arg Arg Arg Ala Val Gly Ile Gly Ala Val Phe Leu Gly
            500                 505                 510

Phe Leu Gly Ala Ala Gly Ser Thr Met Gly Ala Ala Ser Met Thr Leu
        515                 520                 525

Thr Val Gln Ala Arg Asn Leu Leu Ser Gly Ile Val Gln Gln Gln Ser
    530                 535                 540

Asn Leu Leu Arg Ala Pro Glu Ala Gln Gln His Leu Leu Lys Leu Thr
545                 550                 555                 560

Val Trp Gly Ile Lys Gln Leu Gln Ala Arg Val Leu Ala Val Glu Arg
                565                 570                 575

Tyr Leu Arg Asp Gln Gln Leu Leu Gly Ile Trp Gly Cys Ser Gly Lys
            580                 585                 590

Leu Ile Cys Cys Thr Asn Val Pro Trp Asn Ser Ser Trp Ser Asn Arg
        595                 600                 605

Asn Leu Ser Glu Ile Trp Asp Asn Met Thr Trp Leu Gln Trp Asp Lys
    610                 615                 620

Glu Ile Ser Asn Tyr Thr Gln Ile Ile Tyr Gly Leu Leu Glu Glu Ser
625                 630                 635                 640

Gln Asn Gln Gln Glu Lys Asn Glu Gln Asp Leu Leu Ala Leu Asp
                645                 650                 655
```

<210> SEQ ID NO 36
<211> LENGTH: 675
<212> TYPE: PRT
<213> ORGANISM: Artificial Sequence
<220> FEATURE:
<223> OTHER INFORMATION: Recombinant HIV-1 Env sequence

<400> SEQUENCE: 36

-continued

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ala Glu
            20                  25                  30

Asn Leu Trp Val Thr Val Tyr Tyr Gly Val Pro Val Trp Lys Asp Ala
        35                  40                  45

Glu Thr Thr Leu Phe Cys Ala Ser Asp Ala Lys Ala Tyr Glu Thr Glu
    50                  55                  60

Lys His Asn Val Trp Ala Thr His Ala Cys Val Pro Thr Asp Pro Asn
65                  70                  75                  80

Pro Gln Glu Ile His Leu Glu Asn Val Thr Glu Glu Phe Asn Met Trp
                85                  90                  95

Lys Asn Asn Met Val Glu Gln Met His Thr Asp Ile Ile Ser Leu Trp
            100                 105                 110

Asp Gln Ser Leu Lys Pro Cys Val Lys Leu Thr Pro Leu Cys Val Thr
        115                 120                 125

Leu Gln Cys Thr Asn Val Thr Asn Asn Ile Thr Asp Asp Met Arg Gly
    130                 135                 140

Glu Leu Lys Asn Cys Ser Phe Asn Met Thr Thr Glu Leu Arg Asp Lys
145                 150                 155                 160

Lys Gln Lys Val Tyr Ser Leu Phe Tyr Arg Leu Asp Val Val Gln Ile
                165                 170                 175

Asn Glu Asn Gln Gly Asn Arg Ser Asn Asn Ser Asn Lys Glu Tyr Arg
            180                 185                 190

Leu Ile Asn Cys Asn Thr Ser Ala Cys Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Lys Asp Lys Lys Phe Asn Gly Thr Gly Pro Cys Pro
225                 230                 235                 240

Ser Val Ser Thr Val Gln Cys Thr His Gly Ile Lys Pro Val Val Ser
                245                 250                 255

Thr Gln Leu Leu Leu Asn Gly Ser Leu Ala Glu Glu Glu Val Met Ile
            260                 265                 270

Arg Ser Glu Asn Ile Thr Asn Asn Ala Lys Asn Ile Leu Val Gln Phe
        275                 280                 285

Asn Thr Pro Val Gln Ile Asn Cys Thr Arg Pro Asn Asn Met Thr Arg
    290                 295                 300

Lys Ser Ile Arg Ile Gly Pro Gly Gln Ala Phe Tyr Ala Leu Gly Asp
305                 310                 315                 320

Ile Ile Gly Asp Ile Arg Gln Pro His Cys Asn Val Ser Lys Ala Thr
                325                 330                 335

Trp Asn Glu Thr Leu Gly Lys Val Val Lys Gln Leu Arg Lys His Phe
            340                 345                 350

Gly Asn Asn Thr Ile Ile Arg Phe Ala Asn Ser Ser Gly Gly Asp Leu
        355                 360                 365

Glu Val Thr Thr His Ser Phe Asn Cys Gly Gly Glu Phe Phe Tyr Cys
    370                 375                 380

Asn Thr Ser Gly Leu Phe Asn Ser Thr Trp Ile Ser Asn Thr Ser Val
385                 390                 395                 400

Gln Gly Ser Asn Ser Thr Gly Ser Asn Asp Ser Ile Thr Leu Pro Cys
                405                 410                 415

Arg Ile Lys Gln Ile Ile Asn Met Trp Gln Arg Ile Gly Gln Cys Met
```

```
            420                 425                 430

Tyr Ala Pro Pro Ile Gln Gly Val Ile Arg Cys Val Ser Asn Ile Thr
        435                 440                 445

Gly Leu Ile Leu Thr Arg Asp Gly Gly Ser Thr Asn Ser Thr Thr Glu
    450                 455                 460

Thr Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Arg Cys Lys Arg Arg Val Val Gly Asn Ser Thr His Lys Gln Leu
            500                 505                 510

Thr His His Met Arg Arg Arg Arg Arg Arg Ala Val Gly Ile Gly Ala
        515                 520                 525

Val Phe Leu Gly Phe Leu Gly Ala Ala Gly Ser Thr Met Gly Ala Ala
    530                 535                 540

Ser Met Thr Leu Thr Val Gln Ala Arg Asn Leu Leu Ser Gly Ile Val
545                 550                 555                 560

Gln Gln Gln Ser Asn Leu Leu Arg Ala Pro Glu Ala Gln Gln His Leu
                565                 570                 575

Leu Lys Leu Thr Val Trp Gly Ile Lys Gln Leu Gln Ala Arg Val Leu
            580                 585                 590

Ala Val Glu Arg Tyr Leu Arg Asp Gln Gln Leu Leu Gly Ile Trp Gly
        595                 600                 605

Cys Ser Gly Lys Leu Ile Cys Cys Thr Asn Val Pro Trp Asn Ser Ser
    610                 615                 620

Trp Ser Asn Arg Asn Leu Ser Glu Ile Trp Asp Asn Met Thr Trp Leu
625                 630                 635                 640

Gln Trp Asp Lys Glu Ile Ser Asn Tyr Thr Gln Ile Ile Tyr Gly Leu
                645                 650                 655

Leu Glu Glu Ser Gln Asn Gln Gln Glu Lys Asn Glu Gln Asp Leu Leu
            660                 665                 670

Ala Leu Asp
        675


<210> SEQ ID NO 37
<211> LENGTH: 654
<212> TYPE: PRT
<213> ORGANISM: Artificial Sequence
<220> FEATURE:
<223> OTHER INFORMATION: Recombinant HIV-1 Env sequence

<400> SEQUENCE: 37

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ala Val
            20                  25                  30

Glu Lys Leu Trp Val Thr Val Tyr Tyr Gly Val Pro Val Trp Lys Asp
        35                  40                  45

Ala Lys Thr Thr Leu Phe Cys Ala Ser Asp Ala Lys Ala Tyr Asp Thr
    50                  55                  60

Glu Val His Asn Val Trp Ala Thr His Ala Cys Val Pro Thr Asp Pro
65                  70                  75                  80

Asn Pro Gln Glu Met Leu Leu Asp Asn Val Thr Glu Asn Phe Asn Met
                85                  90                  95

Trp Lys Asn Asp Met Val Asp Gln Met His Glu Asp Val Ile Ser Leu
```

```
            100                 105                 110

Trp Asp Gln Ser Leu Lys Pro Cys Val Lys Leu Thr Pro Leu Cys Val
        115                 120                 125

Thr Leu Glu Cys Thr Asp Ser Ser Asn Gln Thr His Tyr Asn Glu Ser
    130                 135                 140

Met Gln Glu Ile Lys Asn Cys Thr Phe Asn Val Thr Thr Glu Ile Arg
145                 150                 155                 160

Asp Arg Lys Gln Arg Val Gln Ala Leu Phe Tyr Lys Leu Asp Ile Val
                165                 170                 175

Ser Leu Glu Lys Asn Ser Ser Thr Tyr Arg Leu Ile Asn Cys Asn Thr
            180                 185                 190

Ser Ala Cys Thr Gln Ala Cys Pro Lys Val Thr Phe Asp Pro Ile Pro
        195                 200                 205

Ile His Tyr Cys Thr Pro Ala Gly Tyr Ala Ile Leu Lys Cys Asn Asn
    210                 215                 220

Glu Thr Phe Asn Gly Thr Gly Pro Cys Arg Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Lys Asp Ile Met Ile Arg Ser Glu Asn Leu Thr
            260                 265                 270

Asp Asn Ala Lys Thr Ile Ile Val His Leu Asn Gln Thr Val Glu Ile
        275                 280                 285

Val Cys Ile Arg Pro Asn Asn Asn Thr Arg Gln Ser Ile Arg Ile Gly
    290                 295                 300

Pro Gly Gln Val Phe Tyr Ala Thr Gly Asp Ile Ile Gly Asp Ile Arg
305                 310                 315                 320

Gln Ala Tyr Cys Thr Ile Asn Thr Thr Ala Trp Asn Glu Thr Leu Gln
                325                 330                 335

Arg Val Ser Lys Lys Leu Ala Glu His Phe Pro Asn Lys Thr Ile Arg
            340                 345                 350

Phe Ala Pro Ser Ser Gly Gly Asp Leu Glu Ile Thr Thr His Ser Phe
        355                 360                 365

Asn Cys Arg Gly Glu Phe Phe Tyr Cys Asn Thr Ser Gly Leu Phe Asn
    370                 375                 380

Ser Thr Tyr Met Thr Asn Gly Thr Phe Thr Tyr Lys Leu Asn Asp Thr
385                 390                 395                 400

Asn Ile Thr Ile Pro Cys Arg Ile Lys Gln Ile Ile Asn Met Trp Gln
                405                 410                 415

Glu Val Gly Arg Cys Met Tyr Ala Pro Pro Ile Ala Gly Asn Ile Thr
            420                 425                 430

Cys Lys Ser Asn Ile Thr Gly Met Leu Leu Val Arg Asp Gly Gly Lys
        435                 440                 445

Asn Glu Asn Ser Thr Glu Glu Thr Phe Arg Pro Gly Gly Gly Asn Met
    450                 455                 460

Arg Asp Asn Trp Arg Ser Glu Leu Tyr Lys Tyr Lys Val Val Glu Ile
465                 470                 475                 480

Lys Pro Leu Gly Val Ala Pro Thr Lys Cys Lys Arg Arg Val Val Gly
                485                 490                 495

Arg Arg Arg Arg Arg Arg Ala Val Gly Ile Gly Ala Val Phe Leu Gly
            500                 505                 510

Phe Leu Gly Ala Ala Gly Ser Thr Met Gly Ala Ala Ser Met Thr Leu
        515                 520                 525
```

```
Thr Val Gln Ala Arg Asn Leu Leu Ser Gly Ile Val Gln Gln Gln Ser
    530                 535                 540

Asn Leu Leu Arg Ala Pro Glu Ala Gln Gln His Leu Leu Lys Leu Thr
545                 550                 555                 560

Val Trp Gly Ile Lys Gln Leu Gln Ala Arg Val Leu Ala Val Glu Arg
                565                 570                 575

Tyr Leu Arg Asp Gln Gln Leu Leu Gly Ile Trp Gly Cys Ser Gly Lys
            580                 585                 590

Leu Ile Cys Cys Thr Asn Val Pro Trp Asn Ser Ser Trp Ser Asn Arg
        595                 600                 605

Asn Leu Ser Glu Ile Trp Asp Asn Met Thr Trp Leu Gln Trp Asp Lys
    610                 615                 620

Glu Ile Ser Asn Tyr Thr Gln Ile Ile Tyr Gly Leu Leu Glu Glu Ser
625                 630                 635                 640

Gln Asn Gln Gln Glu Lys Asn Glu Gln Asp Leu Leu Ala Leu
                645                 650


<210> SEQ ID NO 38
<211> LENGTH: 675
<212> TYPE: PRT
<213> ORGANISM: Artificial Sequence
<220> FEATURE:
<223> OTHER INFORMATION: Recombinant HIV-1 Env sequence

<400> SEQUENCE: 38

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ala Glu
            20                  25                  30

Asn Leu Trp Val Thr Val Tyr Tyr Gly Val Pro Val Trp Lys Asp Ala
        35                  40                  45

Glu Thr Thr Leu Phe Cys Ala Ser Asp Ala Lys Ala Tyr Glu Thr Glu
    50                  55                  60

Lys His Asn Val Trp Ala Thr His Ala Cys Val Pro Thr Asp Pro Asn
65                  70                  75                  80

Pro Gln Glu Ile His Leu Glu Asn Val Thr Glu Glu Phe Asn Met Trp
                85                  90                  95

Lys Asn Asn Met Val Glu Gln Met His Thr Asp Ile Ile Ser Leu Trp
            100                 105                 110

Asp Gln Ser Leu Lys Pro Cys Val Lys Leu Thr Pro Leu Cys Val Thr
        115                 120                 125

Leu Gln Cys Thr Asn Val Thr Asn Asn Ile Thr Asp Asp Met Arg Gly
    130                 135                 140

Glu Leu Lys Asn Cys Ser Phe Asn Met Thr Thr Glu Leu Arg Asp Lys
145                 150                 155                 160

Lys Gln Lys Val Tyr Ser Leu Phe Tyr Arg Leu Asp Val Val Gln Ile
                165                 170                 175

Asn Glu Asn Gln Gly Asn Arg Ser Asn Asn Ser Asn Lys Glu Tyr Arg
            180                 185                 190

Leu Ile Asn Cys Asn Thr Ser Ala Cys Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Lys Asp Lys Lys Phe Asn Gly Thr Gly Pro Cys Pro
225                 230                 235                 240
```

-continued

```
Ser Val Ser Thr Val Gln Cys Thr His Gly Ile Lys Pro Val Val Ser
                245                 250                 255

Thr Gln Leu Leu Leu Asn Gly Ser Leu Ala Glu Glu Glu Val Met Ile
            260                 265                 270

Arg Ser Glu Asn Ile Thr Asn Asn Ala Lys Asn Ile Leu Val Gln Phe
        275                 280                 285

Asn Thr Pro Val Gln Ile Asn Cys Thr Arg Pro Asn Asn Asn Thr Arg
    290                 295                 300

Lys Ser Ile Arg Ile Gly Pro Gly Gln Ala Phe Tyr Ala Thr Gly Asp
305                 310                 315                 320

Ile Ile Gly Asp Ile Arg Gln Ala His Cys Asn Val Ser Lys Ala Thr
                325                 330                 335

Trp Asn Glu Thr Leu Gly Lys Val Val Lys Gln Leu Arg Lys His Phe
            340                 345                 350

Gly Asn Asn Thr Ile Ile Arg Phe Ala Asn Ser Ser Gly Gly Asp Leu
        355                 360                 365

Glu Val Thr Thr His Ser Phe Asn Cys Gly Gly Glu Phe Phe Tyr Cys
    370                 375                 380

Asn Thr Ser Gly Leu Phe Asn Ser Thr Trp Ile Ser Asn Thr Ser Val
385                 390                 395                 400

Gln Gly Ser Asn Ser Thr Gly Ser Asn Asp Ser Ile Thr Leu Pro Cys
                405                 410                 415

Arg Ile Lys Gln Ile Ile Asn Met Trp Gln Arg Ile Gly Gln Cys Met
            420                 425                 430

Tyr Ala Pro Pro Ile Gln Gly Val Ile Arg Cys Val Ser Asn Ile Thr
        435                 440                 445

Gly Leu Ile Leu Thr Arg Asp Gly Gly Ser Thr Asn Ser Thr Thr Glu
    450                 455                 460

Thr Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Arg Cys Lys Arg Arg Val Val Gly Asn Ser Thr His Lys Gln Leu
            500                 505                 510

Thr His His Met Arg Arg Arg Arg Arg Arg Ala Val Gly Ile Gly Ala
        515                 520                 525

Val Phe Leu Gly Phe Leu Gly Ala Ala Gly Ser Thr Met Gly Ala Ala
    530                 535                 540

Ser Met Thr Leu Thr Val Gln Ala Arg Asn Leu Leu Ser Gly Ile Val
545                 550                 555                 560

Gln Gln Gln Ser Asn Leu Leu Arg Ala Pro Glu Ala Gln Gln His Leu
                565                 570                 575

Leu Lys Leu Thr Val Trp Gly Ile Lys Gln Leu Gln Ala Arg Val Leu
            580                 585                 590

Ala Val Glu Arg Tyr Leu Arg Asp Gln Gln Leu Leu Gly Ile Trp Gly
        595                 600                 605

Cys Ser Gly Lys Leu Ile Cys Cys Thr Asn Val Pro Trp Asn Ser Ser
    610                 615                 620

Trp Ser Asn Arg Asn Leu Ser Glu Ile Trp Asp Asn Met Thr Trp Leu
625                 630                 635                 640

Gln Trp Asp Lys Glu Ile Ser Asn Tyr Thr Gln Ile Ile Tyr Gly Leu
                645                 650                 655
```

-continued

```
Leu Glu Glu Ser Gln Asn Gln Gln Glu Lys Asn Glu Gln Asp Leu Leu
        660                 665                 670

Ala Leu Asp
        675
```